US008278421B2

(12) United States Patent
Masat et al.

(10) Patent No.: US 8,278,421 B2
(45) Date of Patent: Oct. 2, 2012

(54) HUMAN ANTIBODIES SPECIFIC FOR GASTRIN MATERIALS AND METHODS

(75) Inventors: Linda Masat, Walnut Creek, CA (US); Marina Roell, Concord, CA (US)

(73) Assignee: Xoma Techolology Ltd., Berkeley, CA (US)

( * ) Notice: Subject to any disclaimer, the term of this patent is extended or adjusted under 35 U.S.C. 154(b) by 500 days.

(21) Appl. No.: 12/293,890

(22) PCT Filed: Dec. 13, 2006

(86) PCT No.: PCT/US2006/047840
§ 371 (c)(1),
(2), (4) Date: Jun. 3, 2009

(87) PCT Pub. No.: WO2007/111661
PCT Pub. Date: Oct. 4, 2007

(65) Prior Publication Data
US 2009/0311257 A1     Dec. 17, 2009

Related U.S. Application Data

(60) Provisional application No. 60/784,501, filed on Mar. 20, 2006.

(51) Int. Cl.
C07K 16/00    (2006.01)
C12P 21/08    (2006.01)
A61K 39/395   (2006.01)
A61K 39/00    (2006.01)

(52) U.S. Cl. ............... 530/387.1; 530/387.3; 530/388.1; 530/388.85; 530/391.1; 424/130.1; 424/133.1; 424/141.1; 424/178.1

(58) Field of Classification Search .................. None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,391,904 A | 7/1983 | Litman et al. |
| 4,419,446 A | 12/1983 | Howley et al. |
| 4,495,285 A | 1/1985 | Shimizu et al. |
| 4,496,689 A | 1/1985 | Mitra |
| 4,560,655 A | 12/1985 | Baker |
| 4,601,978 A | 7/1986 | Karin |
| 4,609,546 A | 9/1986 | Hiratani et al. |
| 4,640,835 A | 2/1987 | Shimizu et al. |
| 4,657,866 A | 4/1987 | Kumar |
| 4,670,417 A | 6/1987 | Iwasaki et al. |
| 4,676,980 A | 6/1987 | Segal et al. |
| 4,766,106 A | 8/1988 | Katre et al. |
| 4,767,704 A | 8/1988 | Cleveland et al. |
| 4,791,192 A | 12/1988 | Nakagawa et al. |
| 4,927,762 A | 5/1990 | Darfler |
| 4,965,199 A | 10/1990 | Capon et al. |
| 4,975,278 A | 12/1990 | Senter et al. |
| 5,057,313 A | 10/1991 | Shih et al. |
| 5,122,469 A | 6/1992 | Mather et al. |
| 5,223,409 A | 6/1993 | Ladner et al. |
| 5,229,275 A | 7/1993 | Goroff |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,589,369 A | 12/1996 | Seidman et al. |
| 5,591,669 A | 1/1997 | Krimpenfort et al. |
| 5,624,821 A | 4/1997 | Winter et al. |
| 5,643,768 A | 7/1997 | Kawasaki |
| 5,658,754 A | 8/1997 | Kawasaki |
| 5,688,506 A | 11/1997 | Grimes et al. |
| 5,766,886 A | 6/1998 | Studnicka et al. |
| 5,770,429 A | 6/1998 | Lonberg et al. |
| 5,877,293 A | 3/1999 | Adair et al. |
| 5,939,598 A | 8/1999 | Kucherlapati et al. |
| 5,969,108 A | 10/1999 | McCafferty et al. |
| 6,054,287 A | 4/2000 | Gao et al. |
| 6,091,001 A | 7/2000 | Jakobovits et al. |
| 6,114,598 A | 9/2000 | Kucherlapati et al. |
| 6,194,551 B1 | 2/2001 | Idusogie et al. |
| 6,306,393 B1 | 10/2001 | Goldenberg |
| 6,489,145 B1 | 12/2002 | Short |
| 6,605,449 B1 | 8/2003 | Short |
| 6,657,103 B1 | 12/2003 | Kucherlapati et al. |
| 6,699,658 B1 | 3/2004 | Wittrup et al. |
| 6,737,056 B1 | 5/2004 | Presta |
| 6,833,268 B1 | 12/2004 | Green et al. |
| 6,861,510 B1 | 3/2005 | Gevas et al. |

(Continued)

FOREIGN PATENT DOCUMENTS

EP    0073657    3/1983

(Continued)

OTHER PUBLICATIONS

Rudikoff, Giusti, Cook, and Scharff. Single amino acid substitution altering antigen binding specificity. Proceedings of the National Academy of Sciences, 1982. vol. 79, pp. 1979-1983.*

Mac Callum, Martin, and Thornton. Antibody-antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

(Continued)

*Primary Examiner* — Anne M. Gussow
(74) *Attorney, Agent, or Firm* — Marshall, Gerstein & Borun LLP

(57) ABSTRACT

The present invention relates to materials and methods for human antibodies specific for the peptide hormone gastrin and uses of these antibodies in the treatment of subjects having cancer and other conditions or disorders related to gastrin expression.

23 Claims, 7 Drawing Sheets

U.S. PATENT DOCUMENTS

| | | | |
|---|---|---|---|
| 2002/0004215 | A1 | 1/2002 | Osbourn et al. |
| 2002/0199213 | A1 | 12/2002 | Tomizuka et al. |
| 2003/0028071 | A1 | 2/2003 | Handy et al. |
| 2003/0032995 | A1 | 2/2003 | Handy et al. |
| 2003/0044772 | A1 | 3/2003 | Watkins et al. |
| 2003/0068326 | A1 | 4/2003 | Gevas et al. |
| 2003/0092125 | A1 | 5/2003 | Davis et al. |
| 2003/0118592 | A1 | 6/2003 | Ledbetter et al. |
| 2003/0124129 | A1 | 7/2003 | Oliner |
| 2003/0133939 | A1 | 7/2003 | Ledbetter et al. |
| 2003/0190317 | A1 | 10/2003 | Baca et al. |
| 2003/0194404 | A1 | 10/2003 | Greenfeder et al. |
| 2005/0037421 | A1 | 2/2005 | Honda et al. |
| 2005/0136049 | A1 | 6/2005 | Ledbetter et al. |
| 2006/0020119 | A1 | 1/2006 | Grimes et al. |

FOREIGN PATENT DOCUMENTS

| | | |
|---|---|---|
| EP | 315 456 | 5/1989 |
| EP | 404097 | 12/1990 |
| WO | WO-81/01145 | 4/1981 |
| WO | WO-87/05330 | 9/1987 |
| WO | WO-88/07378 | 10/1988 |
| WO | WO-90/13646 | 11/1990 |
| WO | WO-91/00906 | 1/1991 |
| WO | WO-91/17271 | 11/1991 |
| WO | WO-92/01047 | 1/1992 |
| WO | WO-92/09690 | 6/1992 |
| WO | WO-92/15679 | 9/1992 |
| WO | WO-92/18619 | 10/1992 |
| WO | WO-92/20791 | 11/1992 |
| WO | WO-93/01288 | 1/1993 |
| WO | WO-93/11161 | 6/1993 |
| WO | WO-93/19172 | 9/1993 |
| WO | WO-94/02602 | 2/1994 |
| WO | WO-94/11026 | 5/1994 |
| WO | WO-95/15388 | 6/1995 |
| WO | WO-96/11953 | 4/1996 |
| WO | WO-96/27011 | 9/1996 |
| WO | WO-96/30498 | 10/1996 |
| WO | WO-96/32478 | 10/1996 |
| WO | WO-96/33735 | 10/1996 |
| WO | WO-96/34096 | 10/1996 |
| WO | WO-97/34631 | 9/1997 |
| WO | WO-98/24893 | 6/1998 |
| WO | WO-99/10494 | 3/1999 |
| WO | WO-99/58572 | 11/1999 |
| WO | WO-02/092780 | 11/2002 |
| WO | WO-03/041600 | 5/2003 |
| WO | WO-2004/033693 | 4/2004 |
| WO | WO-2005/095459 A2 | 10/2005 |

OTHER PUBLICATIONS

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Fishwild et al. High-avidity human IgGκ monoclonal antibodies from a novel strain of minilocus transgenic mice. *Nat. Biotechnol.* 14: 845-51 (1996).

Fix, Strategies for delivery of peptides utilizing absorption-enhancing agents. *J. Pharm. Sci.* 85: 1282-5 (1996).

Fleer et al, Stable multicopy vectors for high-level secretion of recombinant human serum albumin by Kluyveromyces yeasts. *Bio/Technology.* 9: 968-75 (1991).

Fominaya et al., Target cell-specific DNA transfer mediated by a chimeric multidomain protein. Novel non-viral gene delivery system. *J. Biol. Chem.* 271: 10560-8 (1996).

Friedman et al., Antitumor activity of the single-chain immunotoxin BR96 sFv-PE40 against established breast and lung tumor xenografts. *J. Immunol.* 150: 3054-61 (1993).

Friedmann, Progress toward human gene therapy. *Science.* 244: 1275-81 (1989).

Fuchs et al., Targeting recombinant antibodies to the surface of *Escherichia coli*: fusion to a peptidoglycan associated lipoprotein. *Bio/Technology.* 9: 1369-72 (1991).

Garrad et al., Fab assembly and enrichment in a monovalent phage display system. *Bio/Technology.* 9: 1373-7 (1991).

Gibril et al., Advances in evaluation and management of gastrinoma in patients with Zollinger-Ellison syndrome. *Curr. Gastroenterol. Rep.* 7: 114-21 (2005).

Gilliam et al., G17DT: An antigastrin immunogen for the treatment of gastrointestinal malignancy. *Exp. Opin. Biol. Ther.* 7: 397-404 (2007).

Gleeson et al., Organ-specific autoimmunity induced by lymphopenia. *Immunol. Rev.* 149: 97-125 (1996).

Goding, Conjugation of antibodies with fluorochromes: modifications to the standard methods. *J. Immunol. Methods.* 13: 215-26 (1976).

Goldenberg, New developments in monoclonal antibodies for cancer detection and therapy. *CA Cancer J. Clin..* 44: 43-64 (1994).

Graham et al., Characteristics of a human cell line transformed by DNA from human adenovirus type 5. *J. Gen. Virol.* 36: 59 (1977).

Gram et al., In vitro selection and affinity maturation of antibodies from a naive combinatorial immunoglobulin library. *Proc. Natl. Acad. Sci. USA.* 89: 3576-80 (1992).

Greenberg et al., A new antigen receptor gene family that undergoes rearrangement and extensive somatic diversification in sharks. *Nature.* 374: 168-73 (1995).

Griffiths et al. Human anti-self antibodies with high specificity from phage display libraries. *EMBO J.* 12: 725-34 (1993).

Gruber et al., Efficient tumor cell lysis mediated by a bispecific single chain antibody expressed in *Escherichia coli. J. Immunol.* 152: 5368 (1994).

Guss et al., Structure of the IgG-binding regions of streptococcal protein G. *EMBO J.* 5: 1567-75 (1986).

Sojar et al., A chemical method for the deglycosylation of proteins. *Arch. Biochem. Biophys.* 259: 52-7 (1987).

Ham et al., Media and growth requirements. *Methods Enzymol.* 58: 44-93 (1979).

Hamers-Casterman et al., Naturally occurring antibodies devoid of light chains. *Nature.* 363: 446-8 (1993).

Hanes et al., In vitro selection and evolution of functional proteins by using ribosome display. *Proc. Natl. Acad. Sci. USA.* 94: 4937-42 (1997).

Chothia et al., Conformations of immunoglobulin hypervariable regions. *Nature.* 342: 877-83 (1989).

Chowdhury, Targeting random mutations to hotspots in antibody variable domains for affinity improvement. *Methods Mol. Biol.* 178: 269-85 (2002).

Clackson et al., Making antibody fragments using phase display libraries. *Nature.* 352: 624-8 (1991).

Clackson et al., In vitro selection from protein and peptide libraries. *TIBTECH.* 12: 173-84 (1994).

Co et al., Humanized antibodies for antiviral therapy. *J. Immunol.* 152: 2968-76 (1994).

Colby et al., Potent inhibition of huntingtin aggregation and cytotoxicity by a disulfide bond-free single-domain intracellular antibody. *Proc. Natl. Acad. Sci. USA.* 101: 17616-21 (2004).

Colucci et al., Gastrin promotes human colon cancer cell growth via CCK-2 receptor-mediated cyclooxygenase-2 induction and prostaglandin E2 production. *Br. J. Pharmacol.* 144: 338-48 (2005).

Conrath et al., β-Lactamase inhibitors derived from single-domain antibody fragments elicited in the Camelidae. *Antimicrob. Agents Chemother.* 45: 2807-12 (2001).

Cortez-Retamozo et al., Efficient cancer therapy with a nanobody-based conjugate. *Cancer Res.* 64: 2853-57 (2004).

Cunningham et al., High-resolution epitope mapping of hGH-receptor interactions by alanine-scanning mutagenesis. *Science.* 244: 1081-5 (1989).

Daugherty et al., Quantitative analysis of the effect of the mutation freguency on the affinity maturation of single chain Fv antibodies. *Proc Natl Acad Sci U S A*. 97: 2029-34 (2000).

Day et al., Characterization of virulence factors of mouse-adapted Helicobacter pylori strain SS1 and effects on gastric hydrophobicity. *Dig. Dis. Sci*. 46: 1943-51 (2001).

Delle Fave et al., Progression of gastric enterochromaffin-like cells growth in Zollinger-Ellison syndrome and atrophic body gastritis patients. *Dig. Liver. Dis*. 34: 270-8 (2002).

Desmyter et al., Antigen specificity and high affinity binding provided by one single loop of a camel single-domain antibody. *J. Biol. Chem*. 276: 26285-90 (2001).

Dohlsten et al.,Monoclonal antibody-superantigen fusion proteins: Tumor-specific agents for T-cell-based tumor therapy. *Proc. Natl. Acad. Sci. USA*. 91: 8945-9 (1994).

Edge et al., Deglycosylation of glycoproteins by trifluoromethanesulfonic acid. *Anal. Biochem*. 118: 131 (1981).

Engvall et al., Enzyme-linked immunosorbent assay, ELSA. *J. Immunol*. 109: 129-35 (1972).

Evan et al., Isolation of monoclonal antibodies specific for human c-*mys*.proto-oncogene product. *Mol. Cell. Biol*. 5: 3610-16 (1985).

Ewert et al., Biophysical properties of camelid $V_{HH}$ domains compared to those of human $V_H3$ domains. *Biochemistry*. 41: 3628-36 (2002).

Ferrara et al., Modulation of therapeutic antibody effector functions by glycosylation engineering: Influence of golgi enzyme localization domain and co-expression of heterologous β1, 4-N-acetylglucosaminyltransferase III and golgi α-mannosidase II. *Biotechnol. Bioeng*.. 93: 851-61 (2006).

Field et al., Purificiation of a RAS-responsive adenylyl cyclase complex from *Saccharmyces cerevisiae* by use of an epitope addition method. *Mol. Cell. Biol*. 8: 2159-65 (1988).

Finley et al., Expression of the gastrin gene in the normal human colon and colorectal adenocarcinoma. *Cancer Res*. 53: 2919-26 (1993).

Becker et al., An antibody-interleukin 2 fusion protein overcomes tumor heterogeneity by induction of a cellular immune response. *Proc. Natl. Acad. Sci. USA*. 93: 7826-31 (1996).

Berlin et al., Phase III study of gemcitabine in combination with fluorouracil versus gemcitabine alone in patients with advanced pancreatic carcinoma: Eastern Cooperative Oncology Group Trial E2297. *J. Clin. Oncol*. 20: 3270-5 (2002).

Better et al. *Escherichia coli* secretion of an active chimeric antibody fragment. *Science*. 240: 1041-43 (1988).

Better et al., Potent anti-CD5 ricin A chain immunoconjugates from bacterially produced Fab' and F(ab')$_2$. *Proc. Natl. Acad. Sci. USA*. 90: 457-61 (1993).

Biocca, et al., Expression and targeting of intracellular antibodies in mammalian cells. *EMBO J*. 9: 101-8 (1990).

Bird et al., Single-chain antigen-binding proteins.*Science*. 242: 423-6 (1988).

Boleti et al., Construction, expression and characterization of a cingle chain anti-tumour antibody (scFv)-IL-2 protein.*Ann. Oncol*. 6: 945-7 (1995).

Boulianne et al, Production of functional chimaeric mouse/human antibody. *Nature*. 312: 643-6 (1984).

Brennan et al., Preparation of biospecific antibodies by chemical recombination of monoclonal immunoglobulin G1 fragments. *Science*. 229: 81-3 (1985).

Brett et al., Phase II study of anti-gastrin-17 antibodies, raised to G17DT, in advanced pancreatic cancer. *J. Clin. Oncol*. 20: 4225-31 (2002).

Brinkmann et al., B3(Fv)-PE38KDEL, a single-chain immunotoxin that causes complete regression of a human carcinoma in mice. *Proc. Natl. Acad. Sci. USA*. 88: 8616-20 (1991).

Bruggerrmann et al., Designer mice: The production of human antibody repertoires in transgenic animals. *Year in Immunol*. 7: 33-40 (1993).

Burmester, et al., Selection, characterization and X-ray structure of anti-ampicillin single chain Fv fragments from phage-displayed murine antibody libraries. *J. Mol. Biol.*, 309 671-685 (2001).

Burton et al., Human antibodies from combinatorial libraries. *Adv. Immunol*. 57: 191-280 (1994).

Caplin et al., Expression and processing of gastrin in pancreatic adenocarcinoma. *Br. J. Surg*. 87: 1035-40 (2000).

Caron et al., Engineered humanized dimeric forms of IgG are more effective antibodies. *J. Exp. Med*. 176: 1191-5 (1992).

Carter et al., High level *Escherichia coli* expression and production of a bivalent humanized antibody fragment. *Bio/Technology*. 10: 163-7 (1992).

Caton et al., Influenza virus hemagglutinin-specific antibodies isolated from a combinatorial expression library are closely related to the immune response of the donor. *Proc. Natl. Acad. Sci. USA*. 87: 6450-54 (1990).

Chappel et al. Identification of the Fcγ receptor class I binding site in human IgG through the use of recombinant IgG1/IgG2 hybrid and point-mutated antibodies. *Proc. Natl. Acad. Sci. U S A*. 88: 9036-40 (1991).

Chaudhary et al., A recombinant immunotoxin consisting of two antibody variable domains fused to *Pseudomonas* exotoxin. *Nature*. 339: 394-7 (1989).

Chen et al., Altered control of gastric acid secretion in gastrin-cholecystokinin double mutant mice. *Gastroenterology*. 126: 476-87 (2004).

Chothia et al., Canonical structures for the hypervariable regionsof immunoglobulins. *J. Mol. Biol*. 196: 901-17 (1987).

Ahmed et al., High and low affinity receptors mediate growth effects of gastrin and gastrin-Gly on DLD-1 human colonic carcinoma cells. *FEBS Lett*. 556:199-203 (2004).

Aihara et al., Pharmacological control of gastric acid secretion for the treatment of acid-related peptic disease: Past, present, and future. *Pharmacol. Ther*. 98: 109-27 (2003).

Alderuccio et al., Spontaneous autoimmune gastritis in C3H/He mice: a new mouse model for gastric autoimmunity. *Am. J. Pathol*. 153:1311-8 (1998).

Alderuccio et al., Expression of the gastric H/K-ATPase alpha-subunit in the thymus may explain the dominant role of the beta-subunit in the pathogenesis of autoimmune gastritis. *Autoimmunity*. 25:167-75 (1997).

Anderson, Human gene therapy. *Nature*. 392: Suppl. 6679: 20-25 (1998).

Angal et al. A single amino acid substitution abolishes the heterogeneity of chimeric mouse/human (IgG4) antibody. *Mol. Immunol*. 30:105-8 (1993).

Aplin et al., Preparation, properties, and applications of carbohydrate conjugated of proteins and lipids. *CRC Crit. Rev. Biochem*. 259-306 (1981).

Armour et al. Differential binding to human FcγRIIa and FcγRIIb receptors by human IgG wildtype and mutant antibodies. *Mol. Immunol*. 40: 585-93 (2003).

Baldwin et al., Gastrin, gastrin receptors and colorectal carcinoma. *Gut*. 42: 581-4 (1998).

Barbas et al. Assembly of combinatorial antibody libraries on phage surfaces: the gene III site. *Proc. Natl. Acad. Sci. USA*. 88: 7978-82 (1991).

Barnes et al., Methods for growth of cultured cells in serum-free medium. *Anal. Biochem*. 102: 255-70 (1980).

Barrett et al., Organ-specific autoimmunity induced by adult thymectomy and cyclophosphamide-induced lymphopenia. *Eur. J. Immunol*. 25: 238-44 (1995).

Batra et al., Recombinant anti-erbB2 immunotoxins containing *Pseudomonas* exotoxin. *Proc. Natl. Acad. Sci. USA*. 89: 5867-71 (1992).

Bayer et al., The avidin-biotin complex in affinity cytochemistry. *Meth. Enzymol*. 62: 308-15 (1979).

Hank et al., Activation of human effector cells by a tumor reactive recombinant anti-ganglioside GD2 interleukin-2 fusion protein (ch14.18-IL2). *Clin. Cancer Res*. 2: 1951 (1996).

Hawkins et al., Selection of phage antibodies by binding affinity. Mimicking affinity maturation. *J. Mol. Biol*. 226: 889-96 (1992).

Hay et al. Bacteriophage cloning and *Escherichia coli* expression of a human IgM Fab. *Hum. Antibodies Hybridomas*. 3: 81-5 (1992).

Heng et al., Making cell-permeable antibodies (Transbody) through fusion of protein transduction domains (PTD) with single chain variable fragment (scFv) antibodies: potential advantages over antibodies expressed within the intracellular environment (Intrabody). *Med. Hypotheses.* 64: 1105-8 (2005).

Henwood et al., Expression of gastrin in developing gastric adenocarcinoma. *Br. J. Surg.* 88: 564-8 (2001).

Hirst et al., Comparison of effect of peptide length and sulphation on acid secretory potency of gastrin in the cat in vivo and in vitro. *J. Physiol.* 357: 441-52 (1984).

Holliger et al., "Diabodies": small bivalent and bispecific antibody fragments. *Proc. Natl. Acad. Sci. USA.* 90: 6444-8 (1993).

Hoogenboom et al. Multi-subunit proteins on the surface of filamentous phage: methodologies for displaying antibody (Fab) heavy and light chains. *Nucl. Acids Res.* 19: 4133-7 (1991).

Hoogenboom et al., By-passing immunisation. Human antibodies from synthetic repertoires of germline VH gene segments rearranged in vitro. *J. Mol. Biol.* 227: 381-8 (1991).

Hou et al., Gastric secretion. *Curr. Opin. Gastroenterol.* 22: 583-98 (2006).

Hu et al., A chimeric Lym-1/interleukin 2 fusion protein for increasing tumor vascular permeability and enhancing antibody uptake. *Cancer Res.* 56: 4998-5004 (1996).

Huls et al. Tumor cell killing by in vitro affinity-matured recombinant human monoclonal antibodies. *Cancer Immunol. Immunother.* 50: 163-71 (2001).

Huse et al. Generation of a large combinatorial library of the immunoglobulin repertoire in phage lambda. *Science.* 246: 1275-81(1989).

Huston et al., Protein engineering of antibody binding sites: recovery of specific activity in an anti-digoxin single-chain Fv analogue produced in *Escherichia coli. Proc. Natl. Acad. Sci. USA.* 85: 5879-83 (1988).

Isaacs et al., Therapy with monoclonal antibodies. II. The contribution of Fc gamma receptor binding and the influence of C(H)1 and C(H)3 domains on in vivo effector function. *J. Immunol.* 161: 3862-9 (1998).

Ishida et al. Production of human monoclonal and polyclonal antibodies in TransChromo animals. *Cloning Stem Cells.* 4: 91-102 (2002).

Jakobovits et al., Germ-line transmission and expression of a human-derived yeast artificial chromosome. *Nature.* 362: 255-8 (1993).

Jakobovits et al., Analysis of homozygous mutant chimeric mice: deletion of the immunoglobulin heavy-chain joining region blocks B-cell development and antibody production. *Proc. Natl. Acad. Sci. USA.* 90: 2551-5 (1993).

Jespers et al., Guiding the selection of human antibodies from phage display repertoires to a single epitope of an antigen. *Bio/Technology.* 12: 899-903 (1994).

Jones et al., Replacing the complementarity-determining regions in a human antibody with those from a mouse. *Nature.* 321: 522-5 (1986).

Kanda et al., Involvement of cyclooxygenase-2 in gastric mucosal hypertrophy in gastrin transgenic mice. *Am. J. Physiol. .Gastrointest. Liver Physiol.* 290: G519-27 (2006).

Kettleborough et al., Humanization of a mouse monoclonal antibody by CDR-grafting: the importance of framework residues on loop conformation. *Protein Eng.* 4: 773-83 (1991).

Kohler et al., Continuous cultures of fused cells secreting antibody of predefined specificity. *Nature.* 256: 495-7 (1975).

Kostelny et al., Formation of a bispecific antibody by the use of leucine zippers. *J. Immunol.* 148: 1547-53 (1992).

Kozbor et al., A human hybrid myeloma for production of human monoclonal antibodies. *J. Immunol.* 133: 3001-5 (1984).

Krantis et al., Effects of compound U74500A in animal models of gastric and duodenal ulceration. *Dig. Dis. Sci.* 38: 722-9 (1993).

Kreitman et al., Cytotoxic activities of recombinant immunotoxins composed of Pseudomonas toxin or diphtheria toxin toward lymphocytes from patients with adult T-cell leukemia. *Leukemia.* 7:553-62 (1993).

Kuan et al., Recombinant immunotoxin containing a disulfide-stabilized Fv directed at erbB2 that does not require proteolytic activation. *Biochemistry.* 35: 2872-7 (1996).

Lefranc et al., IMGT, the international ImMunoGeneTics database. Nucl. Acids Res. 27: 209-12 (1999).

Leung et al., Screening for gastric cancer in Asia: Current evidence and practice. *Lancet Oncol.* 9: 279-87 (2008).

Linardou et al., Deoxyribonuclease I (DNAse I). A novel approach for targeted cancer therapy. *Cell Biophys.* 243: 24-25 (1994).

Lindmark et al., Binding of immunoglobulins to protein A and immunoglobulin levels in mammalian sera. *J. Immunol. Meth.* 62: 1-13 (1983).

Low et al., Mimicking somatic hypermutation: affinity maturation of antibodies displayed on bacteriophage using a bacterial mutator strain. *J. Mol. Biol.* 260: 359-68 (1996).

Mahler et al., Experimental Helicobacter pylori infection induces antral-predominant, chronic active gastritis in hispid cotton rats (*Sigmodon hispidus*). *Helicobacter.* 10: 332-44 (2005).

Marks et al, By-passing immunization: building high affinity human antibodies by chain shuffling. *Bio/Technology.* 10: 779-83 (1992).

Marks et al., By-passing immunization. Human antibodies from V-gene libraries displayed on phage. *J. Mol. Biol.* 222: 581-97 (1991).

Marks et al., Selection of human antibodies from phage display libraries. *Methods Mol Biol.* 248: 161-76 (2004).

Massey, Catalytic antibodies catching on. *Nature.* 328: 457-8 (1987).

Mather et al., Culture of testicular cells in hormone-supplemented serum-free medium. *Ann. N.Y. Acad. Sci.* 383: 44-68 (1982).

Mather, Establishment and characterization of two distinct mouse testicular epithelial cell lines. *Biol. Reprod.* 23: 243-51 (1980).

McCafferty et al., Phage antibodies: filamentous phage displaying antibody variable domains. *Nature.* 348: 552-4 (1990).

Mhashilkar et al., Inhibition of HIV-1 Tat-mediated LTR transactivation and HIV-1 infection by anti-Tat single chain intrabodies. *EMBO J.* 14: 1542-51 (1995).

Miller, Human gene therapy comes of age. *Nature.* 357: 455-60 (1992).

Modlin et al., Edkins and a century of acid suppression. *Digestion.* 72: 129-45 (2005).

Morrison et al., Genetically engineered antibody molecules. *Immunol.* 44: 65-92 (1988).

Morrison et al., Chimeric human antibody molecules: Mouse antigen-binding domains with human constant region domains. *Proc. Natl. Acad. Sci., USA.* 81: 6851-5 (1984).

Mulholland et al., Physiology and pathophysiology of gastrin: a review. *Surgery.* 103: 135-47 (1988).

Munson et al., LIGAND: A versatile computerized approach for characterization of ligand-binding systems. *Anal. Biochem.* 107: 220-39 (1980).

Neri et al., High-affinity antigen binding by chelating recombinant antibodies (CRAbs) *J. Mol. Biol.* 246: 367-73 (1995).

Neuberger et al., Recombinant antibodies possessing novel effector functions. *Nature.* 312: 604-8 (1984).

Nguyen et al., The specific variable domain of camel heavy-chain antibodies is encoded in the germline. *J. Mol. Biol.* 275: 413-8 (1998).

Nicholls et al., Characterization of single-chain antibodies (sFv)-toxin fusion proteins produce in vitro in rabbit reticulocyte lysate. *J. Biol. Chem.* 268: 5302-8 (1993).

Nicolet et al., Expression of a tumor-reactive antibody-interleukin 2 fusion protein after in vivo particle-mediated gene delivery. *Cancer Gene Ther.* 2: 161-70 (1995).

Nishimiya et al., Thermodynamic consequences of grafting enhanced affinity toward the mutated antigen onto an antibody. The case of anti-lysozyme antibody, HyHEL-10. *J. Biol. Chem.* 275: 12813-20 (2000).

Noble et al., Stimulation of gastrin-$CCK_B$ receptor promotes migration of gastric AGS cells via multiple paracrine pathways. *Am. J. Physiol. Gastrointest. Liver Physiol.* 284: G75-84 (2003).

Novak et al., Improved sensitivity in flow cytometric intracellular ionized calcium measurement using fluo-3/Fura Red fluorescence ratios. *Cytometry.* 17: 135-41 (1994).

Nuttall et al., Isolation of the new antigen receptor from wobbegong sharks, and use as a scaffold for the display of protein loop libraries. *Mol. Immunol.* 38: 313-26 (2001).

Olafsen et al., Characterization of engineered anti-p185HER-2 (scFv-CH3)2 antibody fragments (minibodies) for tumor targeting. *Protein Eng. Des. Sel.* 17: 315-23 (2004).

Oliyai et al., Prodrugs of peptides and proteins for improved formulation and delivery. *Ann. Rev. Pharmacol. Toxicol.* 32: 521-44 (1993).
Paborsky et al., Mammalian cell transient expression of tissue factor for the production of antigen. *Protein Eng.* 3: 547-53 (1990).
Padlan, Anatomy of the antibody molecule. *Molec. Immunol.* 31: 169-217 (1994).
Palnaes et al., Metabolism and acid secretory effect of sulfated and nonsulfated gastrin-6 in humans. *Am. J. Physiol. Gastrointest. Liver Physiol.* 279: G903-9 (2000).
Pastan et al., Immunotoxins. *Cell.* 47:641-8 (1986).
Paterson et al., Identity and regulation of stored and secreted progastrin-derived peptides in sheep. *Endocrinology.* 145: 5129-40 (2004).
Piontek et al., Differential mode of action of high- and low-affinity CCK/gastrin receptor antagonists in growth inhibition of gastrin— responsive human gastric adenocarcinoma cells in vitro. *Anticancer Res.* 13: 715-20 (1993).
Poljak et al., Production and structure of diabodies. *Structure.* 2: 1121-3 (1994).
Presta et al., Engineering therapeutic antibodies for improved function. *Biochem. Soc. Trans.* 30: 487-90 (2001).
Rajpal et al., A general method for greatly improving the affinity of antibodies by using combinational libraries. *Proc. Natl. Acad. Sci. U S A.* 102: 8466-71 (2005).
Reichman et al., Single domain antibodies: Comparison of camel VH and camelised human VH domains. *J. Immunol. Meth.* 231: 25-38 (1999).
Reubi, Peptide receptors as molecular targets for cancer diagnosis and therapy. *Endocrine Rev.* 24: 389-427 (2003).
Reyes et al., Expression of human beta-interferon cDNA under the control of a thymidine kinase promoter from herpes simplex virus. *Nature.* 297: 598-601 (1982).
Riechmann et al., Reshaping human antibodies for therapy. *Nature.* 332: 323-27 (1988).
Rocha Lima et al., Irinotecan plus gemcitabine induces both radiographic and CA 19-9 tumor marker responses in patients with previously untreated advanced pancreatic cancer. *J. Clin. Oncol.* 20: 1182-91 (2002).
Ross et al., Helicobacter pylori. Its role in the pathogenesis of peptic ulcer disease in a new animal model. *Am. J. Pathol.* 141: 721-7 (1992).
Rothman et al., Antibody-dependent cytotoxicity mediated by natural killer cells is enhanced by castanospermine-induced alterations of IgG glycosylation. *Mol. Immunol.* 26: 1113-23 (1989).
Rozengurt et al., Gastrin, CCK, signaling, and cancer. *Annu. Rev. Physiol.* 63: 49-76 (2001).
Sachs et al., Biological basis of omeprazole therapy. *J. Gastroenterol. Hepatol.* Suppl. 2: 7-18 (1989).
Samuelson et al., Insights into the regulation of gastric acid secretion through analysis of genetically engineered mice. *Annu. Rev. Physiol.* 65: 383-400 (2003).
Sanger et al. DNA sequencing with chain-terminating inhibitors. *Proc. Natl. Acad. Sci. USA.* 74: 5463-7 (1977).
Sarmay et al., Mapping and comparison of the interaction sites on the Fc region of IgG responsible for triggering antibody dependent cellular cytotoxicity (ADCC) through different types of human Fcγ receptor. *Molec. Immunol.* 29: 633-9 (1992).
Sawada et al., Comparison of pathologic changes in Helicobacter pylori-infected Mongolian gerbils and humans. *J. Gastroenterol.* 34: Suppl. 11: 55-60 (1999).
Scarff et al., Immunization with gastric H+/K(+)-ATPase induces a reversible autoimmune gastritis. *Immunology.* 92: 91-98 (1997).
Scatchard et al., The attraction of proteins for small molecules and ions. *Ann. N.Y. Acad. Sci.,* 51: 660 (1949).
Schmidt et al., A bivalent single-chain antibody-toxin specific for ErbB-2 and the EGF receptor. *Int. J. Can.* 65: 538-46 (1996).
Schmitz et al., CCK-B/gastrin receptors in human colorectal cancer. *Eur. J. Clin. Invest.* 31: 812-20 (2001).
Schoonjans et al., Fab chains as an efficient heterodimerization scaffold for the procuction of recomhinant bispecific and trispecific antibody derivatives. *J. Immunol.* 165: 7050-57 (2000).
Schubert et al., Control of acid secretion. *Peptide Ulcer Disease.* 19: 1-25 (1990).
Schubert, Gastric secretion. *Curr. Opin. Gastroenterol.* 19: 519-25 (2003).
Schubert, Gastric secretion. *Curr. Opin. Gastroenterol.* 20: 519-25 (2004).
Schubert, Gastric secretion. *Curr. Opin. Gastroenterol.* 21: 636-43 (2005).
Schuurman et al., The inter-heavy chain disulfide bonds of IgG4 are in equilibrium with intra-chain disulfide bonds. *Mol. Immunol.* 38: 1-8 (2001).
Shalaby et al., Development of humanized bispecific antibodies reactive with cytotoxic lymphocytes and tumor cells overexpressing the HER2 protooncogene. *J. Exp. Med.* 175: 217-25 (1992).
Shamburek et al., Pharmacology of gastric acid inhibition. Baillieres Clinical Gastroenterology. Chapter 2: 23-54 (1993).
Shamburek et al., Control of gastric acid secretion. *Gastrointestinal Pharmacology.* 21: 527-50 (1992).
Shields et al., High resolution mapping of the binding site on human IgG1 for Fc gamma RI, Fc gamma RII, Fc gamma RIII, and FcRn and design of IgG1 variants with improved binding to the Fc gamma R. *J. Biol. Chem.* 276: 6591-604 (2001).
Shields et al., Lack of fucose on human IgG1 N-linked oligosaccharide improves binding to human Fcgamma RIII and antibody-dependent cellular toxicity. *J. Biol. Chem.* 277: 26733-40 (2002).
Shih et al., Site-specific linkage of methotrexate to monoclonal antibodies using an intermediate carrier. *Int. J. Cancer.* 41: 832-9 (1988).
Shinkawa et al., The absence of fucose but not the presence of galactose or bisecting N-acetylglucosamine of human IgG1 complex-type oligosaccharides shows the critical role of enhancing antibody-dependent cellular cytotoxicity. *J. Biol. Chem.* 278: 3466-73 (2003).
Shopes, A genetically engineered human IgG mutant with enhanced cytolytic activity. *J. Immunol.* 148: 2918-22 (1992).
Smith et al., Gastrin and gastrin receptor activation: An early event in the adenoma-carcinoma sequence. *Gut.* 47: 820-24 (2000).
Smith et al., Review article: Gastrin and colorectal cancer. *Aliment Pharmacol. Ther.* 14: 1231-47 (2000).
Smith et al., Gastrimmuno-induced antigastrin-17 antibodies inhibit acid secretion in a rat fistula modal. *Aliment Pharmacol. Ther.* 15: 1981-8 (2001).
Smith et al., Identification of gastrin as a growth peptide in human pancreatic cancer. *Am. J. Physiol.* 268 (1 Pt 2): R135-41 (1995).
Smith et al., Phase I/II study of G17-DT, and anti-gastrin immunogen, in advanced colorectal cancer. *Clin. Cancer Res.* 6: 4719-24 (2000).
Stemmer, DNA shuffling by random fragmentation and reassembly: In vitro recombination for molecular evolution. *Proc. Natl. Acad. Sci. USA.* 91:10747-51 (1994).
Stepan et al., Glycine-extended gastrin exerts growth-promoting effects on human colon cancer cells. *Mol. Med.* 5: 147-59 (1999).
Steplewski et al., Biological activity of human-mouse IgG1, IgG2, IgG3, and IgG4 chimeric monoclonal antibodies with antitumor specificity. *Proc. Natl. Acad. Sci. U S A.* 85: 4852-56 (1998).
Sternberger et al., The unlabeled antibody enzyme method of immunohistochemistry: preparation and properties of soluble antigen-antibody complex (horseradish peroxidase-antihorseradish peroxidase) and its use in identification of spirochetes. *J. Histochem. Cytochem.* 18: 315-33 (1970).
Stevenson et al., A chimeric antibody with dual Fc regions (bisFabFc) prepared by manipulations at the IgG hinge. *Anticancer Drug Design.* 3: 219-30 (1989).
Watson et al., A comparison of the therapeutic effectiveness of gastrin neutralization in two human gastric cancer models: Relation to endocrine and autocrine/paracrine gastrin mediated growth. *Gut.* 45: 812-7 (1999).
Watson et al., Anti-gastrin antibodies raised by gastrimmune inhibit growth of the human colorectal tumour AP5. *Int. J. Cancer.* 61: 233-40 (1995).
Watson et al., Gastrin—active participant or bystander in gastric carcinogenesis? *Nat. Rev. Cancer.* 6: 936-46 (2006).
Weinberg et al., Cholecystokin A and B receptors are differentially expressed in normal pancreas and pancreatic adenocarcinoma. *J. Clin. Invest.* 100: 597-603 (1997).

Weinberg et al., Cholecystokinin and gastrin levels are not elevated in human pancreatic adenocarcinoma. *Cancer Epidemiol. Biomark. Prev.* 10: 721-2 (2001).

Wels et al., EGF receptor and p185$^{erbB-2}$-specific single-chain antibody toxins differ in their cell-killing activity on tumor cells expressing both receptor proteins. *Int. J. Cancer*. 60: 137-44 (1995).

Wheeler et al. Intrabody-based strategies for inhibition of vascular endothelial growth factor receptor-2: Effect on apoptosis, cell growth, and angiogenesis. *FASEB J*. 17: 1733-5 (2003).

Willems et al. Optimizing expression and purification from cell culture medium of trispecific recombinant antibody derivatives. *J. Chromatogr. B Analyt. Technol. Biomed. Life Sci.* 786: 161-76 (2003).

Winter et al., Making antibodies by phage display technology. *Annu. Rev. Immunol*. 12: 433-55 (1994).

Wolff et al., Monoclonal antibody homodimers: Enhanced antitumor activity in nude mice. *Cancer Res*. 53: 2560-5 (1993).

Xu et al. Residue at position 331 in the IgG1 and IgG4 CH2 domains contributes to their differential ability to bind and activate complement. *J. Biol. Chem*. 269: 3469-74 (1994).

Yamane-Ohnuki et al., Establishment of FUT8 knockout Chinese hamster ovary cells: An ideal host cell line for producing completely defucosylated antibodies with enhanced antibody-dependent cellular cytotoxicity. *Biotechnol. Bioeng*. 87: 614-22 (2004).

Yang et al., A genetically engineered fusion protein M4/TNF with increased bifunctional activity refolded in the presence of protein disulfide isomerase. *Hum. Antibodies Hybridomas*. 6:129-36 (1995).

Yaniv, Enhancing elements for activation of eukaryotic promoters. *Nature*. 297:17-8 (1982).

Yassin, Signaling pathways mediating gastrin's growth-promoting effects. *Peptides*. 20: 885-98 (1999).

Yu et al., Peptide-antibody conjugated for tumour therapy : A MHC-Class-II-Restricted tetanus toxin peptide coupled to an anti-Ig light chain antibody can induce cytotoxic lysis of a human B-cell lymphoma by specific CD4 T cells. *Int. J. Cancer*. 56: 244-8 (1994).

Zaccolo et al., The effect of high frequency random mutagenesis on in vitro protein evolution: A study of TEM-1 β-lactamase. *J. Mol. Biol*. 285: 775-83 (1999).

Harris et al., The biological and therapeutic importance or gastrin gene expression in pancreatic adenocarcinomas. *Cancer Res*. 64(16): 5624-31 2004.

Hsu et al., Development of XPA067.06, a potent high affinity human anti-gastrin monoclonal antibody. *Biochem. Pharmacol.*, 76(3): 340-52 (2008).

Supplementary European Search Report and Written Opinion, EP 06 84 7668, dated Jul. 29, 2009.

* cited by examiner

FIGURE 1

XPA.061_VH (SEQ ID NO: 1)
QVQLVQSGAEVKKPGSSVKVSCKVSGGTFSSHAIGWVRQAPGQGLEWIGRIIPSLDLDNSAPKFQDRVTITADKFTNTAYMELRNLRPEDTAFYYCTGDPLYNWTGAHWGRGTMVTVSS

XPA.063_VH (SEQ ID NO: 3)
EVQLVQSGAEVKKPGSSVTVSCKASGGTFDKYAIGWVRQAPGQGLEWMGRIIPSLDLDNSAQKFQDRVTITADKFTTTVYMKLSNLRPEDTAMYYCTRDPLYNWSGSYWGRGTMVTVSS

XPA.065_VH (SEQ ID NO: 5)
EVQLVQSGAEVKKPGSSVTVSCKASGGTFDKYAIGWVRQAPGQGLEWMGRIIPSLDLDNSAQKFQDRVTITADKFTTTVYMELINLRPEDTAMYYCTRDPLYNWSGSYWGRGTMVTVSS

XPA.067_VH (SEQ ID NO: 7)
EVQLVQSGAEVKKPGSSVTVSCKASGGTFDKYAIGWVRQAPGQGLEWMGRIIPTLDLANSAQKFQDRVTITADKFTTTVYMELINLRPEDTAMYYCTRDPLYNWSGSYWGRGTMVTVSS

XPA.081_VH (SEQ ID NO: 9)
EVQLVQSGAEVKKPGSSVTVSCKASGGTFDKYAIGWVRQAPGQGLEWMGRIIPSLDLDNSAQKFQDRVTITADKFTTTVYMKLSNLRPEDTAIYYCTRDPLYQWSGSYWGKGTLVTVSS

CONSENSUS (SEQ ID NO: 11)
EVQLVQSGAEVKKPGSSVTVSCKASGGTFDKYAIGWVRQAPGQGLEWMGRIIPSLDLDNSAQKFQDRVTITADKFTTTVYMELSNLRPEDTAMYYCTRDPLYNWSGSYWGRGTMVTVSS
1234567890123456789012345678901234567890123456789012abc34567890123456789012345678901234567890ab12345678901234567890123

FIGURE 2

XPA.061_VL (SEQ ID NO: 2)
QAVLTQPSSLSASPGASASLTCTLRSDINVGTYRIYWYQQKSGSPPQYLLRYRSDSDKQQGSGVPSRFSGSKDASANAGILLISGLQSEDEADYYCMIWHSSAWVFGGGTKVTVL

XPA.063_VL (SEQ ID NO: 4)
QAVLTQPSSLSASPGASASLTCTLRSGINVGTYRIYWYQQKPGSPPQYLLRYKSDSDKQQGSGVPSRFSGSKDASANAGILLISGLQSEDEADYYCMIWHSSAWVFGGGTKLTVL

XPA.065_VL (SEQ ID NO: 6)
QAVLTQPSSLSASPGTSASLTCTLRSGINVGSYRIYWYQQRPGSPPQYLLRYKSDSDKQQGSGVPSRFSGSKDASANAGVLFISGLQSDDEADYYCMIWHNSAWVFGGGTKLTVL

XPA.067_VL (SEQ ID NO: 8)
QAVLTQPSSLSASPGASASLTCTLRSGINVGTYRIYWYQQKPGSPPQYLLRYKSDSDKQQGSGVPSRFSGSKDASANAGILLISGLQSEDEADYYCMIWHSSAWVFGGGTKLTVL

XPA.081_VL (SEQ ID NO: 10)
QAVLTQPSSLSASPGASASLTCTLRSDINVGTYRIYWYQQKPGSPPQYLLRYKSDSDKQQGSGVPSRFSGSKDASANAGILLISGLQSGDGADYYCMIWHSSAWVFGGGTKLTVL

CONSENSUS (SEQ ID NO: 12)
QAVLTQPSSLSASPGASASLTCTLRSGINVGTYRIYWYQQKPGSPPQYLLRYKSDSDKQQGSGVPSRFSGSKDASANAGILLISGLQSEDEADYYCMIWHSSAWVFGGGTKLTVL
1234567890123456789012345678901abcd234567890123456789012345678ab9012345678901234567890123456789012345678901234567

Figure 3

>XPA.067_VH_AA (PARENT)
EVQLVQSGAEVKKPGSSVTVSCKASGGTFDKYAIGWVRQAPGQGLEWMGRIIPTLDLANSAQKFQDRVTITADKFTTTVYMELTNLRPEDTAMYYCTRDPLYNWSGSYWGRGTMVTVSS

Affinity matured Ab heavy chains:

>XPA.067.6_VH_AA   (SEQ ID NO: 23)
EVQLVQSGAEVKKPGSSVTVSCKASGGTFDKYAIGWVRQAPGQGLEWMGTIIPSLDRAISAQKFQDRVTITADKFTTTVYMELTNLRPEDTAMYYCTRDPLYNWSGSYWGRGTMVTVSS

>XPA.067.9_VH_AA   (SEQ ID NO: 24)
EVQLVQSGAEVKKPGSSVTVSCKASGGTFDKYAIGWVRQAPGQGLEWMGTIIPSLDRAVSAQKFQDRVTITADKFTTTVYMELTNLRPEDTAMYYCTRDPLYNWSGSYWGRGTMVTVSS

>XPA.067.11_VH_AA  (SEQ ID NO: 25)
EVQLVQSGAEVKKPGSSVTVSCKASGGTFDKYAIGWVRQAPGQGLEWMGTIIPDEDRAISAQKFQDRVTITADKFTTTVYMELTNLRPEDTAMYYCTRDPLYNWSGSYWGRGTMVTVSS

>XPA.067.12_VH_AA  (SEQ ID NO: 26)
EVQLVQSGAEVKKPGSSVTVSCKASGGTFDKYAIGWVRQAPGQGLEWMGSINPSADRAISAQKFQDRVTITADKFTTTVYMELTNLRPEDTAMYYCTRDPLYNWSGSYWGRGTMVTVSS

>XPA.067.13_VH_AA  (SEQ ID NO: 27)
EVQLVQSGAEVKKPGSSVTVSCKASGGTFDKYAIGWVRQAPGQGLEWMGTIIPELDRAISAQKFQDRVTITADKFTTTVYMELTNLRPEDTAMYYCTRDPLYNWSGSYWGRGTMVTVSS

>XPA.067.15_VH_AA  (SEQ ID NO: 28)
EVQLVQSGAEVKKPGSSVTVSCKASGGTFDKYAIGWVRQAPGQGLEWMGAINPSEDQAISAQKFQDRVTITADKFTTTVYMELTNLRPEDTAMYYCTRDPLYNWSGSYWGRGTMVTVSS

>XPA.067.18_VH_AA  (SEQ ID NO: 29)
EVQLVQSGAEVKKPGSSVTVSCKASGGTFDKYAIGWVRQAPGQGLEWMGTIMPSLDRAISAQKFQDRVTITADKFTTTVYMELTNLRPEDTAMYYCTRDPLYNWSGSYWGRGTMVTVSS

>XPA.067.19_VH_AA  (SEQ ID NO: 30)
EVQLVQSGAEVKKPGSSVTVSCKASGGTFDKYAIGWVRQAPGQGLEWMGAINPAVDLARSAQKFQDRVTITADKFTTTVYMELTNLRPEDTAMYYCTRDPLYNWSGSYWGRGTMVTVSS

>XPA.067.20_VH_AA  (SEQ ID NO: 31)
EVQLVQSGAEVKKPGSSVTVSCKASGGTFDKYAIGWVRQAPGQGLEWMGMIIPSLDRAKSAQKFQDRVTITADKFTTTVYMELTNLRPEDTAMYYCTRDPLYNWSGSYWGRGTMVTVSS

>XPA.067.21_VH_AA  (SEQ ID NO: 32)
EVQLVQSGAEVKKPGSSVTVSCKASGGTFDKYAIGWVRQAPGQGLEWMGRIIPTLDLANSAQKFQDRVTITADKFTTTVYMELTNLRPEDTAMYYCTRDGPVGMSGSYWGRGTMVTVSS

>XPA.067.25_VH_AA  (SEQ ID NO: 33)
EVQLVQSGAEVKKPGSSVTVSCKASGGTFDKYAIGWVRQAPGQGLEWMGRIIPTLDLANSAQKFQDRVTITADKFTTTVYMELTNLRPEDTAMYYCTRDGPTIESGSYWGRGTMVTVSS

FIGURE 4

| | CDR1 | CDR2 | CDR3 |
|---|---|---|---|
| (Originating) XPA067 VH | KYAIG | RIIPTLDLANSAQKFQD | DPLYNWSGSY |
| M 067.18 | KYAIG | TIMPSLDRAISAQKFQD | DPLYNWSGSY |
| A 067.6 | KYAIG | TIIPSLDRAISAQKFQD | DPLYNWSGSY |
| T 067.9 | KYAIG | TIIPSLDRAVSAQKFQD | DPLYNWSGSY |
| U 067.11 | KYAIG | TIIPDEDRAISAQKFQD | DPLYNWSGSY |
| R 067.12 | KYAIG | SINPSADRAISAQKFQD | DPLYNWSGSY |
| E 067.13 | KYAIG | TIIPELDRAISAQKFQD | DPLYNWSGSY |
| D 067.15 | KYAIG | AINPSEDQAISAQKFQD | DPLYNWSGSY |
| 067.19 | KYAIG | AINPAVDLARSAQKFQD | DPLYNWSGSY |
| A 067.20 | KYAIG | AINPAVDLARSAQKFQD | DPLYNWSGSY |
| B 067.21 | KYAIG | RIIPTLDLANSAQKFQD | DGPVGMSGSY |
| 067.25 | KYAIG | RIIPTLDLANSAQKFQD | DGPTIESGSY |

SEQUENCE LISTING

```
<160> NUMBER OF SEQ ID NOS: 37

<210> SEQ ID NO 1
<211> LENGTH: 119
<212> TYPE: PRT
<213> ORGANISM: Artificial sequence
<220> FEATURE:
<223> OTHER INFORMATION: Synthetic peptide

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ile Ser Gly Gly Thr Phe Ser Ser His
            20                  25                  30

Ala Ile Gly Trp Val Arg Gln Ala Pro Gly Gln Gly Leu Glu Trp Ile
        35                  40                  45

Gly Arg Ile Ile Pro Ser Leu Asp Leu Asp Asn Ser Ala Pro Lys Phe
    50                  55                  60

Gln Asp Arg Val Thr Ile Thr Ala Asp Lys Phe Thr Asn Thr Ala Tyr
65                  70                  75                  80

Met Glu Leu Arg Asn Leu Arg Pro Glu Asp Thr Ala Phe Tyr Tyr Cys
                85                  90                  95

Thr Gly Asp Pro Leu Tyr Asn Trp Thr Gly Ala His Trp Gly Arg Gly
            100                 105                 110

Thr Met Val Thr Val Ser Ser
        115

<210> SEQ ID NO 2
<211> LENGTH: 115
<212> TYPE: PRT
<213> ORGANISM: Artificial sequence
<220> FEATURE:
<223> OTHER INFORMATION: Synthetic peptide

<400> SEQUENCE: 2

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Asp Ile Asn Val Gly Thr
            20                  25                  30

Tyr Arg Ile Tyr Trp Tyr Gln Gln Lys Ser Gly Ser Pro Pro Gln Tyr
        35                  40                  45

Leu Leu Arg Tyr Arg Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Trp Val Phe Gly Gly Gly Thr Lys Val
            100                 105                 110

Thr Val Leu
        115
```

```
<210> SEQ ID NO 3
<211> LENGTH: 119
<212> TYPE: PRT
<213> ORGANISM: Artificial sequence
<220> FEATURE:
<223> OTHER INFORMATION: Synthetic peptide

<400> SEQUENCE: 3

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Arg Ile Ile Pro Ser Leu Asp Leu Asp Asn Ser Ala Gln Lys Phe
    50                  55                  60

Gln Asp Arg Val Thr Ile Thr Ala Asp Lys Phe Thr Thr Thr Val Tyr
65                  70                  75                  80

Met Lys Leu Ser Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
        115

<210> SEQ ID NO 4
<211> LENGTH: 115
<212> TYPE: PRT
<213> ORGANISM: Artificial sequence
<220> FEATURE:
<223> OTHER INFORMATION: Synthetic peptide

<400> SEQUENCE: 4

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Trp Val Phe Gly Gly Thr Lys Leu
            100                 105                 110

Thr Val Leu
        115

<210> SEQ ID NO 5
<211> LENGTH: 119
<212> TYPE: PRT
<213> ORGANISM: Artificial sequence
<220> FEATURE:
<223> OTHER INFORMATION: Synthetic peptide

<400> SEQUENCE: 5

Glu Val Gln Leu Val Gln Ser Gly Ala Glu Val Lys Lys Pro Gly Ser
1               5                   10                  15
```

```
Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Arg Ile Ile Pro Thr Leu Asp Leu Ala Asn Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
                100                 105                 110

Thr Met Val Thr Val Ser Ser
            115
```

<210> SEQ ID NO 6
<211> LENGTH: 115
<212> TYPE: PRT
<213> ORGANISM: Artificial sequence
<220> FEATURE:
<223> OTHER INFORMATION: Synthetic peptide

<400> SEQUENCE: 6

```
Gln Ala Val Leu Thr Gln Pro Ser Ser Leu Ser Ala Ser Pro Gly Thr
1               5                   10                  15

Ser Ala Ser Leu Thr Cys Thr Leu Arg Ser Gly Ile Asn Val Gly Ser
            20                  25                  30

Tyr Arg Ile Tyr Trp Tyr Gln Gln Arg Pro Gly Ser Pro Pro Gln Tyr
        35                  40                  45

Leu Leu Arg Tyr Lys Ser Asp Ser Asp Lys Gln Gly Ser Gly Val
    50                  55                  60

Pro Ser Arg Phe Ser Gly Ser Lys Asp Ala Ser Ala Asn Ala Gly Val
65                  70                  75                  80

Leu Phe Ile Ser Gly Leu Gln Ser Asp Asp Glu Ala Asp Tyr Tyr Cys
                85                  90                  95

Met Ile Trp His Asn Ser Ala Trp Val Phe Gly Gly Thr Lys Leu
                100                 105                 110

Thr Val Leu
        115
```

<210> SEQ ID NO 7
<211> LENGTH: 119
<212> TYPE: PRT
<213> ORGANISM: Artificial sequence
<220> FEATURE:
<223> OTHER INFORMATION: Synthetic peptide

<400> SEQUENCE: 7

```
Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Arg Ile Ile Pro Thr Leu Asp Leu Ala Asn Ser Ala Gln Lys Phe
    50                  55                  60

Gln Asp Arg Val Thr Ile Thr Ala Asp Lys Phe Thr Thr Thr Val Tyr
65                  70                  75                  80
```

```
Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
            115

<210> SEQ ID NO 8
<211> LENGTH: 115
<212> TYPE: PRT
<213> ORGANISM: Artificial sequence
<220> FEATURE:
<223> OTHER INFORMATION: Synthetic peptide

<400> SEQUENCE: 8

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Trp Val Phe Gly Gly Gly Thr Lys Leu
            100                 105                 110

Thr Val Leu
        115

<210> SEQ ID NO 9
<211> LENGTH: 119
<212> TYPE: PRT
<213> ORGANISM: Artificial sequence
<220> FEATURE:
<223> OTHER INFORMATION: Synthetic peptide

<400> SEQUENCE: 9

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Arg Ile Ile Pro Ser Leu Asp Leu Asp Asn Ser Ala Gln Lys Phe
    50                  55                  60

Gln Asp Arg Val Thr Ile Thr Ala Asp Lys Phe Thr Thr Thr Val Tyr
65                  70                  75                  80

Met Lys Leu Ser Asn Leu Arg Pro Glu Asp Thr Ala Ile Tyr Tyr Cys
                85                  90                  95

Thr Arg Asp Pro Leu Tyr Gln Trp Ser Gly Tyr Trp Gly Lys Gly
            100                 105                 110

Thr Leu Val Thr Val Ser Ser
            115

<210> SEQ ID NO 10
<211> LENGTH: 115
```

```
<212> TYPE: PRT
<213> ORGANISM: Artificial sequence
<220> FEATURE:
<223> OTHER INFORMATION: Synthetic peptide

<400> SEQUENCE: 10

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Asp Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Gly Asp Gly Ala Asp Tyr Tyr Cys
                85                  90                  95

Met Ile Trp His Ser Ser Ala Trp Val Phe Gly Gly Gly Thr Lys Leu
            100                 105                 110

Thr Val Leu
    115

<210> SEQ ID NO 11
<211> LENGTH: 119
<212> TYPE: PRT
<213> ORGANISM: Artificial sequence
<220> FEATURE:
<223> OTHER INFORMATION: Synthetic peptide

<400> SEQUENCE: 11

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Arg Ile Ile Pro Ser Leu Asp Leu Asp Asn Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Ser Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
    115

<210> SEQ ID NO 12
<211> LENGTH: 115
<212> TYPE: PRT
<213> ORGANISM: Artificial sequence
<220> FEATURE:
<223> OTHER INFORMATION: Synthetic peptide

<400> SEQUENCE: 12

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30
```

Tyr Arg Ile Tyr Trp Tyr Gln Gln Lys Pro Gly Ser Pro Pro Gln Tyr
            35                  40                  45

Leu Leu Arg Tyr Lys Ser Asp Ser Asp Lys Gln Gln Gly Ser Gly Val
 50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp His Ser Ser Ala Trp Val Phe Gly Gly Gly Thr Lys Leu
             100                 105                 110

Thr Val Leu
        115

<210> SEQ ID NO 13
<211> LENGTH: 357
<212> TYPE: DNA
<213> ORGANISM: Artificial sequence
<220> FEATURE:
<223> OTHER INFORMATION: Synthetic peptide

<400> SEQUENCE: 13
caggtccagc tggtgcagtc tggggctgag gtgaagaagc ctgggtcctc ggtgaaggtc      60
tcctgcaaaa tttctggagg caccttcagc agtcatgcta tcggctgggt gcgacaggcc     120
cctggacaag gcttgagtg gataggtagg atcatcccga gccttgatct cgataactcc      180
gcaccgaagt tccaggacag agtcacgatt accgcggaca aattcacgaa cacagcctac     240
atggagctga ggaacctgag acctgaggac acggccttct attactgtac gggagacccc     300
ctctataatt ggactgggc ccactggggc cggggacaa tggtcaccgt ctcgagt         357

<210> SEQ ID NO 14
<211> LENGTH: 346
<212> TYPE: DNA
<213> ORGANISM: Artificial sequence
<220> FEATURE:
<223> OTHER INFORMATION: Synthetic peptide

<400> SEQUENCE: 14
ccaggctgtg ctgactcagc cgtcttccct ctctgcatct cctggagcat cagccagtct      60
cacctgcacc ttgcgcagtg acatcaatgt tggtacctac aggatatact ggtaccagca     120
gaagtcaggg agtcctcccc agtatctcct gagatacaga tcagactcag ataagcagca     180
gggctctgga gtcccccagcc gcttctctgg atccaaagat gcttcggcca atgcagggat     240
tttactcatc tctgggctcc agtctgagga tgaggctgac tattactgta tgatttggca     300
cagcagcgct tgggtgttcg gcggagggac caaggtcacc gtccta                    346

<210> SEQ ID NO 15
<211> LENGTH: 357
<212> TYPE: DNA
<213> ORGANISM: Artificial sequence
<220> FEATURE:
<223> OTHER INFORMATION: Synthetic peptide

<400> SEQUENCE: 15
gaagtgcagc tggtgcagtc tggggctgag gtgaagaagc ctgggtcctc ggtgacggtc      60
tcctgcaagg cctctggagg cacgttcgac aagtatgcta tcggctgggt gcgacaggcc     120
cctggacaag gcttgagtg gatgggaagg atcatcccta gccttgattt agacaactcc      180
gcacagaagt tccaggacag agtcacgatt accgcggaca aatttacgac cacagtctac     240

```
atgaagctga gcaacctgag acctgaggac acggccatgt actactgtac gcgagacccc    300
ctctataact ggagtgggtc ctactggggc agagggacaa tggtcaccgt ctcgagt       357
```

<210> SEQ ID NO 16
<211> LENGTH: 345
<212> TYPE: DNA
<213> ORGANISM: Artificial sequence
<220> FEATURE:
<223> OTHER INFORMATION: Synthetic peptide

<400> SEQUENCE: 16

```
caggctgtgc tgactcagcc gtcttccctc tctgcatctc ctggagcatc agccagtctc     60
acctgcacct tgcgcagtgg catcaatgtt ggtacctaca ggatatactg gtaccagcag    120
aagccaggga gtcctcccca gtatctcctg aggtacaaat cagactcaga taagcagcag    180
ggctctggag tccccagccg cttctctgga tccaaagatg cttcggccaa tgcaggg att   240 ttactcatct ctgggctcca gtctgaggat gaggctgact attactgtat gatttggcac    300
agcagcgcgt gggtgttcgg cggagggacc aagctgaccg tccta                    345
```

<210> SEQ ID NO 17
<211> LENGTH: 357
<212> TYPE: DNA
<213> ORGANISM: Artificial sequence
<220> FEATURE:
<223> OTHER INFORMATION: Synthetic peptide

<400> SEQUENCE: 17

```
gaggtccagc tggtacagtc tggagctgag gtgaagaagc ctgggtcctc ggtgacggtc     60
tcctgcaagg cctctggagg caccttcgac aagtatgcta tcggctgggt gcggcaggcc    120
cctggacaag gcttgagtg gatgggaagg atcatcccta cccttgattt agcaaactcc     180
gcacagaagt tccaggacag agtcacgatt accgcggaca aattcacgac cacagtctac    240
atggagctga ccaacctgag acctgaggac acggccatgt actactgtac gagagacccc    300
ctctataact ggagtgggtc ctactggggc cgagggacaa tggtcaccgt ctcgagt       357
```

<210> SEQ ID NO 18
<211> LENGTH: 345
<212> TYPE: DNA
<213> ORGANISM: Artificial sequence
<220> FEATURE:
<223> OTHER INFORMATION: Synthetic peptide

<400> SEQUENCE: 18

```
caggctgtgc tgactcagcc gtcttccctc tctgcatctc ctggaacgtc agccagtctc     60
acctgcacct tgcgcagtgg catcaatgtc ggtagttaca ggatatactg gtaccagcag    120
aggccaggga gtcctcccca gtatctcctg aggtataaat cagattcaga taagcagcag    180
ggttctggag tccccagccg cttctctgga tccaaagatg cttcggccaa tgcagggg tt   240 ttattcatct ctgggctcca gtctgacgat gaggctgact attactgtat gatttggcac    300
aacagcgctt gggtgttcgg cggagggacc aagctgaccg tccta                    345
```

<210> SEQ ID NO 19
<211> LENGTH: 357
<212> TYPE: DNA
<213> ORGANISM: Artificial sequence
<220> FEATURE:
<223> OTHER INFORMATION: Synthetic peptide

<400> SEQUENCE: 19

```
gaggtccagc tggtacagtc tggggctgag gtgaagaagc ctgggtcctc ggtgacggtc      60
tcctgcaagg cctctggagg caccttcgac aagtatgcta tcggctgggt gcggcaggcc     120
cctggacaag ggcttgagtg gatgggaagg atcatcccta cccttgattt agcaaactcc     180
gcacagaagt tccaggacag agtcacgatt accgcggaca aattcacgac cacagtctac     240
atggagctga ccaacctgag acctgaggac acggccatgt actactgtac gagagacccc     300
ctctataact ggagtgggtc ctactggggc cgagggacaa tggtcaccgt ctcgagt        357
```

<210> SEQ ID NO 20
<211> LENGTH: 345
<212> TYPE: DNA
<213> ORGANISM: Artificial sequence
<220> FEATURE:
<223> OTHER INFORMATION: Synthetic peptide

<400> SEQUENCE: 20

```
caggctgtgc tgactcagcc gtcttccctc tctgcatctc ctggagcatc agccagtctc      60
acctgcacct tacgcagtgg catcaatgtt ggtacctaca ggatatactg gtaccagcag     120
aagccaggga gtcctcccca gtatctcctg aggtacaaat cagactcaga taagcagcag     180
ggctctggag tccccagccg cttctctgga tccaaagatg cttcggccaa tgcagggatt     240
ttactcatct ctgggctcca gtctgaggat gaggctgact attactgtat gatttggcac     300
agcagcgctt gggtgttcgg cggagggacc aagctgaccg tccta                    345
```

<210> SEQ ID NO 21
<211> LENGTH: 357
<212> TYPE: DNA
<213> ORGANISM: Artificial sequence
<220> FEATURE:
<223> OTHER INFORMATION: Synthetic peptide

<400> SEQUENCE: 21

```
gaggtccagc tggtacagtc tggggctgag gtgaagaagc ctgggtcctc ggtgacggtc      60
tcctgcaagg cctctggagg tacgttcgac aagtatgcta tcggctgggt gcgacaggcc     120
cctggacaag ggcttgagtg gatgggaagg atcatccctt cccttgattt agacaactcc     180
gcacagaagt tccaggacag agtcacgatt accgcggaca aatttacgac cacagtctac     240
atgaagctga gcaacctgag acctgaggac acggccatat actactgtac gcgagacccc     300
ctctatcagt ggagtgggtc ctactggggc aaaggaaccc tggtcaccgt ctcgagt        357
```

<210> SEQ ID NO 22
<211> LENGTH: 345
<212> TYPE: DNA
<213> ORGANISM: Artificial sequence
<220> FEATURE:
<223> OTHER INFORMATION: Synthetic peptide

<400> SEQUENCE: 22

```
caggctgtgc tgactcagcc gtcttccctc tctgcatctc ctggagcatc agccagtctc      60
acctgcacct tgcgcagtga catcaatgtt ggtacctaca ggatatactg gtaccagcag     120
aagccaggga gtcctcccca gtatctcctg aggtacaaat cagactcaga taagcagcag     180
ggctctggag tccccagccg cttctctgga tccaaagatg cttcggccaa tgcagggatt     240
ttactcatct ctgggctcca gtctggggat ggggctgact actactgtat gatttggcac     300
agcagcgctt gggtgttcgg cggagggacc aagctgaccg tccta                    345
```

<210> SEQ ID NO 23
<211> LENGTH: 119
<212> TYPE: PRT
<213> ORGANISM: Artificial sequence
<220> FEATURE:
<223> OTHER INFORMATION: Synthetic peptide

<400> SEQUENCE: 23

```
Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Thr Ile Ile Pro Ser Leu Asp Arg Ala Ile Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
        115
```

<210> SEQ ID NO 24
<211> LENGTH: 119
<212> TYPE: PRT
<213> ORGANISM: Artificial sequence
<220> FEATURE:
<223> OTHER INFORMATION: Synthetic peptide

<400> SEQUENCE: 24

```
Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Thr Ile Ile Pro Ser Leu Asp Arg Ala Val Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
        115
```

<210> SEQ ID NO 25
<211> LENGTH: 119
<212> TYPE: PRT
<213> ORGANISM: Artificial sequence
<220> FEATURE:
<223> OTHER INFORMATION: Synthetic peptide

<400> SEQUENCE: 25

```
Glu Val Gln Leu Val Gln Ser Gly Ala Glu Val Lys Lys Pro Gly Ser
1               5                   10                  15
```

```
Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Thr Ile Ile Pro Asp Glu Asp Arg Ala Ile Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
            115

<210> SEQ ID NO 26
<211> LENGTH: 119
<212> TYPE: PRT
<213> ORGANISM: Artificial sequence
<220> FEATURE:
<223> OTHER INFORMATION: Synthetic peptide

<400> SEQUENCE: 26

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Ser Ile Asn Pro Ser Ala Asp Arg Ala Ile Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
            115

<210> SEQ ID NO 27
<211> LENGTH: 119
<212> TYPE: PRT
<213> ORGANISM: Artificial sequence
<220> FEATURE:
<223> OTHER INFORMATION: Synthetic peptide

<400> SEQUENCE: 27

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Thr Ile Ile Pro Glu Leu Asp Arg Ala Ile Ser Ala Gln Lys Phe
    50                  55                  60

Gln Asp Arg Val Thr Ile Thr Ala Asp Lys Phe Thr Thr Thr Val Tyr
65                  70                  75                  80
```

Met Glu Leu Thr Asn Leu Arg Pro Glu Asp Thr Ala Met Tyr Tyr Cys
              85                  90                  95

Thr Arg Asp Pro Leu Tyr Asn Trp Ser Gly Ser Tyr Trp Gly Arg Gly
            100                 105                 110

Thr Met Val Thr Val Ser Ser
            115

<210> SEQ ID NO 28
<211> LENGTH: 119
<212> TYPE: PRT
<213> ORGANISM: Artificial sequence
<220> FEATURE:
<223> OTHER INFORMATION: Synthetic peptide

<400> SEQUENCE: 28

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Ala Ile Asn Pro Ser Glu Asp Gln Ala Ile Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
            115

<210> SEQ ID NO 29
<211> LENGTH: 119
<212> TYPE: PRT
<213> ORGANISM: Artificial sequence
<220> FEATURE:
<223> OTHER INFORMATION: Synthetic peptide

<400> SEQUENCE: 29

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Thr Ile Met Pro Ser Leu Asp Arg Ala Ile Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
            115

<210> SEQ ID NO 30
<211> LENGTH: 119

<212> TYPE: PRT
<213> ORGANISM: Artificial sequence
<220> FEATURE:
<223> OTHER INFORMATION: Synthetic peptide

<400> SEQUENCE: 30

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Ala Ile Asn Pro Ala Val Asp Leu Ala Arg Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
        115

<210> SEQ ID NO 31
<211> LENGTH: 119
<212> TYPE: PRT
<213> ORGANISM: Artificial sequence
<220> FEATURE:
<223> OTHER INFORMATION: Synthetic peptide

<400> SEQUENCE: 31

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

Ala Ile Gly Trp Val Arg Gln Ala Pro Gly Gln Gly Leu Glu Trp Met
        35                  40                  45

Gly Met Ile Ile Pro Ser Leu Asp Arg Ala Lys Ser Ala Gln Lys Phe
    50                  55                  60

Gln Asp Arg Val Thr Ile Thr Ala Asp Lys Phe Thr Thr Thr Val Tyr
65                  70                  75                  80

Met Glu Leu Thr Asn Leu Arg Pro Glu Asp Thr Ala Met Tyr Tyr Cys
                85                  90                  95

Thr Arg Asp Pro Leu Tyr Asn Trp Ser Gly Ser Tyr Trp Gly Arg Gly
            100                 105                 110

Thr Met Val Thr Val Ser Ser
        115

<210> SEQ ID NO 32
<211> LENGTH: 119
<212> TYPE: PRT
<213> ORGANISM: Artificial sequence
<220> FEATURE:
<223> OTHER INFORMATION: Synthetic peptide

<400> SEQUENCE: 32

Glu Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Asp Lys Tyr
            20                  25                  30

```
Ala Ile Gly Trp Val Arg Gln Ala Pro Gly Gln Gly Leu Glu Trp Met
            35                  40                  45

Gly Arg Ile Ile Pro Thr Leu Asp Leu Ala Asn Ser Ala Gln Lys Phe
 50                  55                  60

Gln Asp Arg Val Thr Ile Thr Ala Asp Lys Phe Thr Thr Thr Val Tyr
 65                  70                  75                  80

Met Glu Leu Thr Asn Leu Arg Pro Glu Asp Thr Ala Met Tyr Tyr Cys
                 85                  90                  95

Thr Arg Asp Gly Pro Val Gly Met Ser Gly Ser Tyr Trp Gly Arg Gly
                100                 105                 110

Thr Met Val Thr Val Ser Ser
            115

<210> SEQ ID NO 33
<211> LENGTH: 119
<212> TYPE: PRT
<213> ORGANISM: Artificial sequence
<220> FEATURE:
<223> OTHER INFORMATION: Synthetic peptide

<400> SEQUENCE: 33

Glu Val Gln Leu Val Gln Ser Gly Ala Glu Val Lys Lys Pro Gly Ser
1               5                  10                  15

Ser Val Thr Val Ser Cys Lys Ala Ser Gly Gly Thr Phe Asp Lys Tyr
             20                  25                  30

Ala Ile Gly Trp Val Arg Gln Ala Pro Gly Gln Gly Leu Glu Trp Met
            35                  40                  45

Gly Arg Ile Ile Pro Thr Leu Asp Leu Ala Asn Ser Ala Gln Lys Phe
 50                  55                  60

Gln Asp Arg Val Thr Ile Thr Ala Asp Lys Phe Thr Thr Thr Val Tyr
 65                  70                  75                  80

Met Glu Leu Thr Asn Leu Arg Pro Glu Asp Thr Ala Met Tyr Tyr Cys
                 85                  90                  95

Thr Arg Asp Gly Pro Thr Ile Glu Ser Gly Ser Tyr Trp Gly Arg Gly
                100                 105                 110

Thr Met Val Thr Val Ser Ser
            115

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide

<400> SEQUENCE: 34

Cys Pro Ser Cys
1

<210> SEQ ID NO 35
<211> LENGTH: 4
<212> TYPE: PRT
<213> ORGANISM: Artificial Sequence
<220> FEATURE:
<223> OTHER INFORMATION: Synthetic peptide

<400> SEQUENCE: 35

Cys Pro Pro Cys
1
```

```
<210> SEQ ID NO 36
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 36

Xaa Ile Xaa Pro Xaa Xaa Asp Xaa Ala Xaa Ser Ala Gln Lys Phe Gln
1               5                   10                  15

Asp

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(6)
<223> OTHER INFORMATION: Xaa can be any naturally occurring amino acid

<400> SEQUENCE: 37

Asp Xaa Xaa Xaa Xaa Xaa Ser Gly Ser Tyr
1               5                   10
```

HUMAN ANTIBODIES SPECIFIC FOR GASTRIN MATERIALS AND METHODS

This application claims the priority benefit of U.S. Provisional Patent Application No. 60/784,501, filed Mar. 20, 2006, hereby incorporated by reference.

FIELD OF THE INVENTION

This invention relates to materials and methods for human antibodies specific for the peptide hormone gastrin and uses of these antibodies in the treatment of subjects having cancer and other conditions or disorders related to gastrin expression.

BACKGROUND OF THE INVENTION

Gastrin is a peptide hormone that signals through the G-protein coupled receptor (GPCR) CCK2R, and has a variety of effects including stimulation of gastric epithelial cell proliferation and acid secretion by parietal cells (Yassin R R, *Peptides* 20:885-98, 1999). It has also been characterized as a factor in the progression of gastric cancers and presents a potential target for therapies that neutralize its function (Smith et al. *Gut* 47:820-24, 2000).

Gastrin is a hormone produced in the digestive tract of many species, including humans. Normal adults produce gastrin in only one cell type—the G cells which line the gastric mucosa in the antral portion of the stomach (Ganong, Review of medical physiology. Norwalk, Conn., Appleton & Lange, 1995). Food intake stimulates the G cells to produce gastrin. Specifically, distension of the lumen of the stomach or the presence of peptides and amino acids in the stomach stimulate gastrin secretion. There is also a neural pathway for gastrin release as the sight or smell of food may stimulate (through the Vagus nerve) release of gastrin.

Once secreted, gastrin has a range of activities on the digestive tract. The primary roles of gastrin in a normal adult are to stimulate acid production by the parietal cells of the stomach and to act as a trophic factor for cells lining the gastrointestinal tract. Gastrin also serves other secondary roles in the digestive tract such as stimulating pepsin and pancreatic enzyme release, and gall bladder contraction and small intestine motility. Gastrin is produced in a precursor form of 101 amino acids called pre-pro-gastrin. This protein goes through a series of cleavage steps to generate several different proteins of varying length (Mulholland et al., *Surgery* 103:135-47, 1988). Additional post-translational steps include glycine addition and amidation. Gastrin may be expressed as pre-pro-gastrin, pregastrin, gastrin 34 (G34, having 34 amino acids), gastrin 17 (G17, having 18 amino acids) and gastrin 14 (G14, having 14 amino acids). Gastrin (G34) stimulates stomach acid secretion and has a trophic effect on gastrointestinal tract (G.I) mucosa. Glycine-Extended Gastrin (Gly-G17) and amidated Gastrin (G17-NH2) also stimulate stomach acid secretion and exhibit a trophic effect on G.I. mucosa.

Gastrin functions in healthy adults are limited to preparing the gastrointestinal tract for the process of digesting ingested food. However, much recent research has implicated gastrin as a growth factor for some types of cancer (Baldwin et al., *Gut* 42:581-4, 1998; Smith et al., *Aliment Pharmacol Ther* 14:1231-47, 2000) including pancreatic, gastric, and colorectal carcinoma. Expression of gastrin and gastrin receptors has been demonstrated in primary tumors taken from cancer patients. Since some tumor types appear to produce and secrete their own gastrin, gastrin can act to stimulate tumor growth via autocrine and paracrine pathways as well as via an endocrine pathway. Several studies published in the literature have demonstrated that tumors taken from cancer patients both produce gastrin and express high levels of gastrin receptors (Schmitz et al., *Eur J Clin Invest* 31:812-20. 2001; Finley et al., *Cancer Res* 53:2919-26. 1993; Weinberg et al., *J Clin Invest* 100:597-603, 1997; Caplin et al., *Br J Surg* 87:1035-40, 2000).

The therapeutic approach of disrupting the gastrin-mediated mitogenesis of cancer cells has been tried in the clinic using small molecule antagonists to the gastrin receptor. Several small molecule antagonists for gastrin receptors have been tested in clinical trials for oncology indications.

Antibodies represent a powerful approach to neutralize therapeutic targets due to their high degree of specificity and affinity. Monoclonal antibodies specific for murine gastrin peptides have been disclosed in U.S. Pat. Nos. 6,861,510 and 5,688,506. However, these antibodies do not possess the desired specificity for human gastrin as needed for clinical therapy.

Thus there remains a need in the art to develop specific antibodies against human gastrin to use in the treatment of cancers and other conditions or disorders associated with gastrin expression.

SUMMARY OF THE INVENTION

The materials and methods of the present invention fulfill the aforementioned and other related needs in the art.

In one embodiment the invention provides antigen-binding compounds, including functional fragments, having the amino acid sequences set forth in SEQ ID NOs: 1-12 and 23-33. In a related embodiment, an aforementioned antigen binding compound is selected from the group consisting of a fully assembled tetrameric antibody, a polyclonal antibody, a monoclonal antibody including a HUMAN ENGINEERED™ antibody; a humanized antibody; a human antibody; a chimeric antibody; a multispecific antibody, an antibody fragment, Fab, F(ab')$_2$; Fv; scFv or single-chain antibody fragment; a diabody; triabody, tetrabody, minibody, linear antibody; chelating recombinant antibody, a tribody or bibody, an intrabody, a nanobody, a small modular immunopharmaceutical (SMIP), a binding-domain immunoglobulin fusion protein, a camelized antibody, a $V_{HH}$ containing antibody, or a variant or derivative of any one of these antibodies, that comprise one or more CDR sequences of the invention and exhibit the desired biological activity. The antigen binding compounds of the invention preferably retain binding affinity of at least $10^{-7}$, $10^{-8}$, $10^{-9}$ M or higher as measured by surface plasmon resonance.

In one aspect, the antibodies of the invention comprise the antibodies. XPA061, XPA063, XPA065, XPA067 and XPA081 set out in amino acid sequences SEQ ID NO: 1-10. It is further contemplated that the antibodies may comprise all or part of the antibodies set out in the above amino acid sequences. In one embodiment, the antibodies comprise at least one of CDR1, CDR2, or CDR3 of the heavy chain of SEQ ID NOs: 1, 3, 5, 7, 9 and 11, or at least one of CDR1, CDR2 or CDR3 of the light chain of SEQ ID NOs: 2, 4, 6, 8, 10 and 12.

In another embodiment of the invention, variants of the aforementioned antibody are provided, comprising a variable heavy chain amino acid sequence which is at least 60, 65, 70, 75, 80, 85, 90, 91, 92, 93, 94, 95, 96, 97, 98, or 99% homologous to the amino acid sequence set forth in SEQ ID NOs: 1, 3, 5, 7, 9 and 11. In a related embodiment, the antibody comprises a variable light chain amino acid sequence which is at least 60, 65, 70, 75, 80, 85, 90, 91, 92, 93, 94, 95, 96, 97, 98, or 99% homologous to the amino acid sequence set forth in SEQ ID NO: 2, 4, 6, 8, 10 and 12.

One aspect of the invention provides an antibody that binds target antigen comprising a heavy chain that comprises any one, two, and/or three of the heavy chain CDR sequences of the invention described below.

Preferably the heavy chain comprises an amino acid sequence identified as a heavy chain CDR3 sequence. Such a "heavy chain CDR3 sequence" includes an amino acid sequence identified as a heavy chain CDR3 sequence set out in FIG. 1 or FIG. 3 and SEQ ID NOs: 1, 3, 5, 7, 9, 11 and 23-33. Alternatively, the heavy chain CDR3 sequence comprises an amino acid sequence that contains one or more amino acid changes compared to any heavy chain CDR3 amino acid sequence identified in FIG. 1 or FIG. 3, i.e. a substitution, insertion or deletion. Preferable substitutions include a substitution to an amino acid at the corresponding position within another heavy chain CDR3 of FIG. 1 or FIG. 3. Alternatively, the heavy chain CDR3 sequence may comprise a consensus amino acid sequence of heavy chain CDR3 shown in FIG. 1 or FIG. 3.

The heavy chain comprising a heavy chain CDR3 sequence of the invention described above may further comprise a "heavy chain CDR1 sequence" of the invention, which includes any of the amino acid sequences identified as a heavy chain CDR1 in FIG. 1 or FIG. 3, amino acid sequences that contain one or more amino acid changes compared to any heavy chain CDR1 identified in FIG. 1 or FIG. 3, preferably a substitution to an amino acid at the corresponding position within another heavy chain CDR1 of FIG. 1, or a consensus sequence of heavy chain CDR1 shown in FIG. 1 or FIG. 3.

Alternatively, the heavy chain comprising a heavy chain CDR3 sequence of the invention described above may further comprise a "heavy chain CDR2 sequence" of the invention, which includes any of the amino acid sequences identified as a heavy chain CDR2 in FIG. 1 or FIG. 3, amino acid sequences that contain one or more amino acid changes compared to any heavy chain CDR2 identified in FIG. 1 or FIG. 3, preferably a substitution to an amino acid at the corresponding position within another heavy chain CDR2 of FIG. 1 or FIG. 3, or a consensus sequence of heavy chain CDR2 shown in FIG. 1 or FIG. 3.

The heavy chain comprising a heavy chain CDR3 sequence of the invention described above may also comprise both (a) a heavy chain CDR1 sequence of the invention described above and (b) a heavy chain CDR2 sequence of the invention described above.

Any of the heavy chain CDR sequences described above may also include amino acids added to either end of the CDRs. Preparation of variants and derivatives of antibodies and antigen-binding compounds of the invention, including affinity maturation or preparation of variants or derivatives containing amino acid analogs, is described in further detail below. Exemplary variants include those containing a conservative or non-conservative substitution of a corresponding amino acid within the amino acid sequence, or a replacement of an amino acid with a corresponding amino acid of a human antibody sequence.

Antibodies comprising any one of the heavy chains described above may further comprise a light chain, preferably a light chain that binds to target antigen, and most preferably a light chain comprising light chain CDR sequences of the invention described below.

Another aspect of the invention provides an antibody that binds target antigen comprising a light chain that comprises any one, two, and/or three of the light chain CDR sequences of the invention described below.

Preferably the light chain comprises an amino acid sequence identified as a light chain CDR3 sequence. Such a "light chain CDR3 sequence" includes an amino acid sequence identified as a light chain CDR3 sequence in FIG. 2 and within SEQ ID NOs: 2, 4, 6, 8 10 and 12. Alternatively, the light chain CDR3 sequence comprises an amino acid sequence that contains one or more amino acid changes compared to any light chain CDR3 amino acid sequence identified in FIG. 2, i.e. a substitution, insertion or deletion. Preferable substitutions include a substitution to an amino acid at the corresponding position within another light chain CDR3 of FIG. 2. Alternatively, the light chain CDR3 sequence may comprise a consensus amino acid sequence of light chain CDR3 shown in FIG. 2.

The light chain comprising a light chain CDR3 sequence of the invention described above may further comprise a "light chain CDR1 sequence" of the invention, which includes any of the amino acid sequences identified as a light chain CDR1 in FIG. 2, amino acid sequences that contain one or more amino acid changes compared to any light chain CDR1 identified in FIG. 2, preferably a substitution to an amino acid at the corresponding position within another light chain CDR1 of FIG. 2, or a consensus sequence of light chain CDR1 shown in FIG. 2.

Alternatively, the light chain comprising a light chain CDR3 sequence of the invention described above may further comprise a "light chain CDR2 sequence" of the invention, which includes any of the amino acid sequences identified as a light chain CDR2 in FIG. 2, amino acid sequences that contain one or more amino acid changes compared to any light chain CDR2 identified in FIG. 2, preferably a substitution to an amino acid at the corresponding position within another light chain CDR2 of FIG. 2, or a consensus sequence of light chain CDR2 shown in FIG. 2.

The light chain comprising a light chain CDR3 sequence of the invention described above may also comprise both (a) a light chain CDR1 sequence of the invention described above and (b) a light chain CDR2 sequence of the invention described above.

Antibodies comprising any one of the light chains described above may further comprise a heavy chain, preferably a heavy chain that binds to target antigen, and most preferably a heavy chain comprising heavy chain CDR sequences of the invention described above.

In yet another embodiment, the antibody or antigen-binding compound comprises a constant region and one or more heavy and light chain variable framework regions of a human antibody sequence. In a related embodiment, the antibody comprises a modified or unmodified constant region of a human IgG1, IgG2, IgG3 or IgG4. In an exemplary embodiment, the constant region is optionally modified to enhance or decrease certain properties. For example, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

In exemplary embodiments, the antibody of the invention is derived from, based on, or contains part of the human antibody consensus sequence, human germline sequence, human consensus germline sequence, or any one of the human antibody sequences in Kabat, NCBI Ig Blast, which enables searching all Ig sequences in the database, including germline sequences (maintained by the National Center for Biotechnology Information); Kabat Database, Martin, A. C. R. "Accessing the Kabat Antibody Sequence Database by Computer" Proteins: Structure, Function and Genetics, 25 (1996), 130-133;

ImMunoGeneTics database (Montpellier France) Lefranc, M.-P. et al., Nucleic Acids Research, 27, 209-212, 1999;

V-Base, Tomlinson, I. M., Williams, S. C., Ignatovich, O., Corbett, S. J. & Winter, G. (1996) VBASE Sequence Directory (Medical Research Council Centre for Protein Engineering, Cambridge, UK);

Zurich, Burmester, et al., Selection, characterization and X-ray structure of anti-ampicillin single chain Fv fragments from phage-displayed murine antibody libraries. J. Mol. Biol., 309 (2001) 671-685;

The Therapeutic Antibody Human Homology Project (TAHHP), "Reshaping antibodies for therapy" Edward G. Routledge, Scott D. Gorman and Mike Clark, in Protein Engineering of Antibody Molecules for Prophylactic and Therapeutic Applications in Man pp. 13-44 (1993), Academic Titles, Nottingham, England;

Humanization by design, Bendig, M. M., Kettleborough, C. A., Jones, S. T., Maeda, H. and Saldanha, J. (1993), "The humanisation of mouse monoclonal antibodies by CDR-grafting: Examples with anti-viral and anti-tumour cell antibodies", in Monoclonal Antibodies 2: Applications in Clinical Oncology ed. A. A. Epenetos, pp 119-140, Chapman & Hall Medical Publishers; Leger, O. J. P. and Saldanha, J. W. (2000), "Preparation of recombinant antibodies from immune rodent spleens and the design of their humanization by CDR grafting", in Monoclonal Antibodies: A Practical Approach eds. P. Shepherd and C. Dean, pp 25-69, Oxford University Press;

Antibody Resources, Antibody Engineering (by T T Wu), Humana Press.

In yet another embodiment of the invention, the aforementioned antibody has an affinity Kd of at least $10^{-7}$ M. In a related embodiment, the antibody has an affinity Kd of at least $10^{-9}$ M.

In one aspect, the invention specifically contemplates sterile compositions of isolated monoclonal antibody that binds to gastrin with an affinity Kd ranging from about $10^{-8}$ M to $10^{-12}$ M, or about $10^{-9}$ M to $10^{-12}$ M, or $10^{-9}$ M to $10^{-11}$ M; in a related aspect, the invention contemplates the use of such compositions to treat disorders associated with gastrin expression.

Yet another aspect of the invention provides non-immunoglobulin-like recombinant polypeptides or other compounds that comprise any of the heavy chain or light chain CDR sequences of the invention described above, or any combinations of these CDR sequences. For example, such compounds may comprise a CDR sequence of the invention as a single copy or in multiple copies in, for example, a tandemly repeated or multivalent configuration. Such compounds may further comprise other CDR sequences in single or multiple copies. Such compounds may also include non-peptidyl linkages.

In still another embodiment of the invention, an isolated nucleic acid is provided comprising a nucleic acid sequence encoding the aforementioned antibody. In a related embodiment, the isolated nucleic acid comprises a heavy chain nucleic acid sequence which is at least 60, 65, 70, 75, 80, 85, 90, 91, 92, 93, 94, 95, 96, 97, 98, or 99% identical to the heavy chain nucleotide sequence set forth in SEQ ID NO: 13, 15, 17, 19 and 21. In yet another related embodiment, the isolated nucleic acid comprises a light chain nucleic acid sequence which is at least 60, 65, 70, 75, 80, 85, 90, 91, 92, 93, 94, 95, 96, 97, 98, or 99% identical to the light chain nucleotide sequence set forth in SEQ ID NOs: 14, 16, 18, 20 and 22.

In another embodiment, a vector comprising the aforementioned isolated nucleic acid is provided. In a related embodiment, the aforementioned vector is provided wherein the isolated nucleic acid is operably linked to a regulatory control sequence. In still another embodiment, a host cell is provided comprising the aforementioned vector.

Numerous methods are contemplated in the present invention. For example, a method of producing an aforementioned antibody is provided comprising culturing the aforementioned host cell such that the isolated nucleic acid is expressed to produce the antibody. In a related embodiment, the method further comprises the step of recovering the antibody from the host cell culture. In a related embodiment, an isolated antibody produced by the aforementioned method is provided.

A further aspect of the invention addresses the portions of the compounds of the invention that do not bind the target antigen but instead are responsible for other functions, such as circulating half-life, direct cytotoxic effect, detectable labeling, or activation of the recipient's endogenous complement cascade or endogenous cellular cytotoxicity. Antibodies of the invention may comprise all or a portion of the constant region and may be of any isotype, including IgA (e.g., IgA1 or IgA2), IgD, IgE, IgG (e.g. IgG1, IgG2, IgG3 or IgG4), or IgM. In addition to, or instead of, comprising a constant region, antigen-binding compounds of the invention may include an epitope tag, a salvage receptor epitope, a label moiety for diagnostic or purification purposes, or a cytotoxic moiety such as a radionuclide or toxin.

In another embodiment of the invention, a pharmaceutical composition is provided comprising any one of the aforementioned antibodies and a pharmaceutically suitable carrier, excipient or diluent. Preferably the antibodies and compounds of the invention are administered in a therapeutically effective amount, i.e., an amount sufficient to ameliorate a clinical sign or symptom of a condition or disorder associated with the target protein expression, to a subject in need of such treatment. In a related embodiment, the pharmaceutical composition further comprises a second therapeutic agent. In yet another related embodiment, the pharmaceutical composition is provided wherein the second therapeutic agent is a growth factor, a cytokine, a chemotherapeutic agent, or a radiotherapeutic agent. In another embodiment the second therapeutic agent is another antibody.

In another embodiment of the invention, the aforementioned methods are provided wherein the subject is a mammal. In a related embodiment, the mammal is human.

In another embodiment, the aforementioned methods are provided wherein the antibody inhibits the interaction between the target and a binding partner. In yet another embodiment, the aforementioned methods are provided wherein the antibody is administered at a dose between about 2 µg/kg to 50 mg/kg, 0.1 mg/kg to 30 mg/kg, or 0.1 mg/kg to 10 mg/kg.

In another embodiment of the invention, the use of an antibody of the invention is contemplated in the manufacture of a medicament for preventing or reducing a condition or disorder associated with target protein expression, as defined herein.

In any of the aforementioned uses, the medicament is coordinated with treatment using a second therapeutic agent.

In another embodiment of the invention, the use of a synergistic combination of an antibody of the invention for preparation of a medicament for treating a patient exhibiting symptoms of a condition or disorder disclosed herein wherein the medicament is coordinated with treatment using a second therapeutic agent is contemplated. In a related embodiment, the second therapeutic agent is a chemokine, a cytokine, a growth factor, a chemotherapeutic agent, a radiotherapeutic agent, or radiation therapy.

Embodiments of any of the aforementioned uses are contemplated wherein the amount of antibody in the medicament is at a dose effective to reduce the dosage of second therapeutic agent required to achieve a therapeutic effect.

The amount of antibody in any of the aforementioned medicaments may be at a dose between about 2 µg/kg to 50 mg/kg body weight. In a related embodiment, the amount of antibody in the medicament is at a dose between about 0.1 mg/kg to 30 mg/kg body weight. In still another embodiment, the amount of antibody in the medicament is at a dose between about 0.1 mg/kg to 10 mg/kg body weight.

Kits are also contemplated by the present invention. In one embodiment, a kit comprises a therapeutically effective amount of a composition of the invention, packaged in a container, such as a vial or bottle, and further comprising a label attached to or packaged with the container, the label describing the contents of the container and providing indications and/or instructions regarding use of the contents of the container to prevent or reduce a condition or disorder associated with target protein expression.

BRIEF DESCRIPTION OF THE DRAWINGS

FIG. 1 shows the heavy chain amino acid sequences of anti-gastrin antibodies XPA061, XPA063, XPA065, XPA067, XPA081 and a consensus sequence. CDRs are underlined and Chothia numbering for all sequences is included beneath the consensus sequence.

FIG. 2 shows the light chain amino acid sequences of anti-gastrin antibodies XPA061, XPA063, XPA065, XPA067, XPA081 and a consensus sequence. CDRs are underlined and Chothia numbering for all sequences is included beneath the consensus sequence.

FIG. 3 shows the heavy chain amino acid sequences of the XPA.067 affinity matured antibodies (SEQ ID NOs: 23-33). CDRs are underlined.

FIG. 4 is a comparison of the heavy chain CDR regions of the originating XPA067 antibody and the affinity matured antibodies (set out in SEQ ID NOs: 23-33).

DETAILED DESCRIPTION OF THE INVENTION

Figure 5:
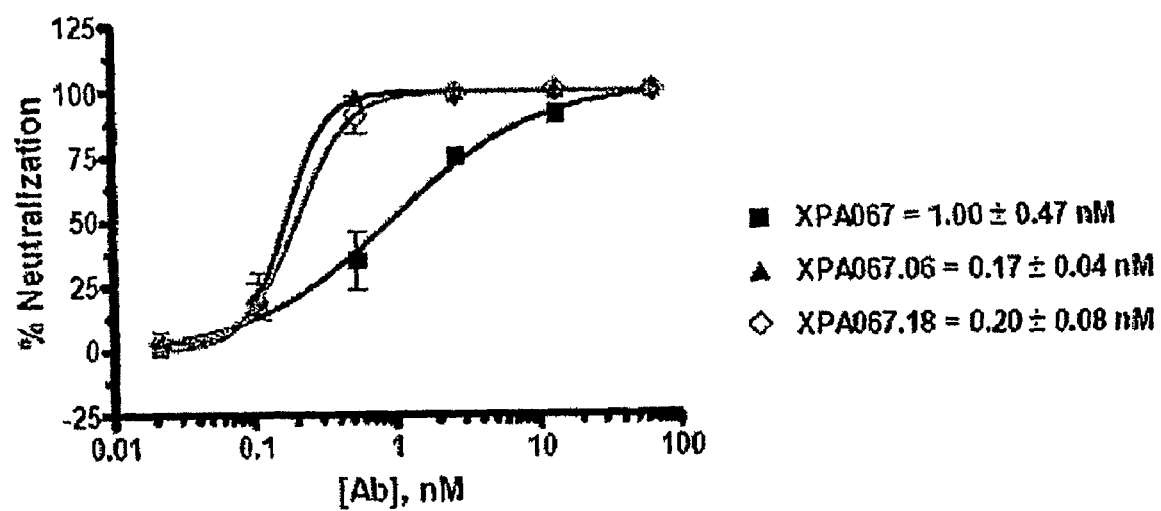
FIG. 5 illustrates the improved gastrin neutralization capacity of reformatted, affinity matured antibodies XPA067.06 and XPA067.18 compared to parent antibody XPA067.

The present invention addresses a need in the art to develop therapeutics to treat conditions or disorders associated with target antigen expression. The present invention provides molecules or agents that interact with the target to eliminate signaling through binding partners of the target.

In order that the invention may be more completely understood, several definitions are set forth.

As used herein, "target" or "target antigen" refers to the gastrin peptide hormone. Gastrin may be the 34 amino acid gastrin peptide or may be a shorter version of the peptide, such as the 17 amino acid or 14 amino acid variant of gastrin. In a preferred embodiment the gastrin is human gastrin.

As used herein, the "desired biological activity" of an anti-target antibody is the ability to bind to gastrin and inhibit its functional effects.

As used herein, a "condition" or "disorder associated with target expression" is a condition or disorder in which target activity is detrimental and includes diseases and other disorders in which high levels of target have been shown to be or are suspected of being either responsible for the pathophysiology of the disorder or a factor that contributes to a worsening of the disorder, as well as diseases and other disorders in which high levels of target expression are associated with undesirable clinical signs or symptoms. Such disorders may be evidenced, for example, by an increase in the levels of target secreted and/or on the cell surface or increased signalling in the affected cells or tissues of a subject suffering from the disorder. The increase in target levels may be detected, for example, using an target specific antibody as described above.

Exemplary conditions or disorders associated with target expression include cancers, such as pancreatic cancer, esophageal cancer, gastric cancer, colorectal cancer, and small lung cell carcinoma, as well as gastric ulcer, duodenal ulcer, other ulcers or conditions associated with H. Pylori, gastroesophageal reflux disease, autoimmune gastritis, atrophic body gastritis, Zollinger-Ellison syndrome associated with tumor of the pancreas (gastrinoma), and inflammatory bowel disease.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (µ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.* 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, (*J. Mol. Biol.* 196:901-917, 1987); Chothia et al., (*Nature* 342:878-883, 1989).

The hypervariable region of an antibody refers to the CDR amino acid residues of an antibody which are responsible for antigen-binding. The hypervariable region comprises amino acid residues from a CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, $5^{th}$ Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., *J. Mol. Biol.* 196: 901-917 (1987)].

Framework or FR residues are those variable domain residues other than the hypervariable region residues.

"Heavy chain variable region" as used herein refers to the region of the antibody molecule comprising at least one complementarity determining region (CDR) of said antibody heavy chain variable domain. The heavy chain variable region may contain one, two, or three CDRs of said antibody heavy chain.

"Light chain variable region" as used herein refers to the region of an antibody molecule, comprising at least one complementarity determining region (CDR) of said antibody light chain variable domain. The light chain variable region may contain one, two, or three CDRs of said antibody light chain, which may be either a kappa or lambda light chain depending on the antibody.

The term "antibody" is used in the broadest sense and includes fully assembled antibodies, monoclonal antibodies, polyclonal antibodies, multispecific antibodies (e.g., bispecific antibodies), antibody fragments that can bind antigen (e.g., Fab', F'(ab)$_2$, Fv, single chain antibodies, diabodies), and recombinant peptides comprising the forgoing as long as they exhibit the desired biological activity. Antigen-binding portions may be produced by recombinant DNA techniques or by enzymatic or chemical cleavage of intact antibodies. Antibody fragments or antigen-binding portions include, inter alia, Fab, Fab', F(ab')$_2$, Fv, domain antibody (dAb), complementarity determining region (CDR) fragments, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a $V_{HH}$ containing antibody, or a variant or a derivative thereof, and polypeptides that contain at least a portion of an immunoglobulin that is sufficient to confer specific antigen binding to the polypeptide, such as a CDR sequence, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the natural antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce an effector function of a target antigen to which it binds. Accordingly, a "neutralizing" anti-target antibody is capable of eliminating or significantly reducing an effector function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an antibody that "specifically binds" is "target specific", is "specific for" target or is "immunoreactive" with the target antigen refers to an antibody or antibody substance of the invention that binds the target antigen with greater affinity than with similar antigens. In one aspect, the target-binding polypeptides of the invention, or fragments, variants, or derivatives thereof, will bind with a greater affinity to human target as compared to its binding affinity to target of other, i.e., non-human, species, but binding polypeptides that recognize and bind orthologs of the target are within the scope of the invention.

For example, a polypeptide that is an antibody or fragment thereof "specific for" its cognate antigen indicates that the variable regions of the antibodies recognize and bind the polypeptide of interest with a detectable preference (i.e., able to distinguish the polypeptide of interest from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody for use in the methods of the invention are well known and routinely practiced in the art. For a comprehensive discussion of such assays, see Harlow et al. (Eds), *Antibodies A Laboratory Manual*; Cold Spring Harbor Laboratory, Cold Spring Harbor, N.Y. (1988), Chapter 6. Antibodies for use in the invention can be produced using any method known in the art.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous. Moreover, epitopes may be mimetic (mimotopes) in that they comprise a three dimensional structure that is identical to the epitope used to generate the peptibody, yet comprise none or only some of the amino acid residues found in the target that were used to stimulate the peptibody immune response. As used herein, a mimotope is not considered a different antigen from the epitope bound by the selective binding agent; the selective binding agent recognizes the same three-dimensional structure of the epitope and mimotope.

The term "derivative" when used in connection with antibody substances and polypeptides of the invention refers to polypeptides chemically modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the invention.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample.

The term "therapeutically effective amount" is used herein to indicate the amount of target-specific composition of the invention that is effective to ameliorate or lessen symptoms or signs of disease associated with target protein expression.

The present invention provides a target-specific antibody, which may comprise those exemplary sequences set out in FIGS. 1 and 2, fragments, variants and derivatives thereof, pharmaceutical formulations including a target-specific antibody recited above, methods of preparing the pharmaceutical formulations, and methods of treating patients with the pharmaceutical formulations and compounds.

Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody of the invention, if it comprises a constant domain, may be of any of these subclasses or isotypes.

The antibodies of the present invention may exhibit binding affinity to antigen of a $K_a$ of greater than or equal to about $10^5 M^{-1}$, greater than or equal to about $10^6 M^{-1}$, or greater than or equal to about $10^7 M^{-1}$, or greater than or equal to about $10^8 M^{-1}$, or greater than or equal to about $10^9 M^{-1}$, $10^{10} M^{-1}$, $10^{11} M^{-1}$ or $10^{12} M^{-1}$. Such affinities may be readily determined using conventional techniques, such as by equilibrium dialysis; by using the BIAcore 2000 instrument, using general procedures outlined by the manufacturer; by radioimmunoassay using $^{125}I$ labeled target antigen; or by another method known to the skilled artisan. The affinity data may be analyzed, for example, by the method of Scatchard et al., (Ann N.Y. Acad. Sci., 51:660, 1949).

Antibody Polypeptides of the Invention

The present invention encompasses amino acid molecules encoding target specific antibodies. In exemplary embodiments, a target specific antibody of the invention can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form. In some embodiments, a heavy chain and a light chain of a target specific immunoglobulin are different amino acid molecules. In other embodiments, the same amino acid molecule contains a heavy chain variable region and a light chain variable region of a target specific antibody.

In some embodiments, the amino acid sequence of the human anti-target antibody comprises one or more CDRs of the amino acid sequence of the light chain variable region ($V_L$) of antibodies XPA061, XPA063, XPA065, XPA067, and XPA081 set out in FIG. 2 or variants thereof. In some embodiments, the $V_L$ comprises the amino acid sequence from the beginning of the CDR1 to the end of the CDR3 of the light chain of any one of the foregoing antibodies.

In one embodiment, the target specific antibody comprises a light chain CDR1, CDR2 or CDR3, each of which are independently selected from the CDR1, CDR2 and CDR3 regions of an antibody having a light chain variable region comprising the amino acid sequence of the $V_L$ region set out in SEQ ID NOs: 2, 4, 6, 8, 10 and 12, or encoded by a nucleic acid molecule encoding the $V_L$ region set out in SEQ ID NOs: 14, 16, 18, 20 and 22. In one aspect the light chain CDR1 is from approximately residues 24-34, CDR2 is from approximately residues 50-56 and CDR3 extends from approximately residues 89-97, according to Chothia numbering. A polypeptide of the target specific antibody may comprise the CDR1, CDR2 and CDR3 regions of an antibody comprising the amino acid sequence of the $V_L$ region selected from the group consisting of XPA.061XPA063, XPA065, XPA067, and XPA081.

In some embodiments, the human target specific antibody comprises one or more CDRs of the amino acid sequence of the heavy chain variable region ($V_H$) of antibody XPA.061, XPA063, XPA065, XPA067, and XPA081 set out in FIG. 1 or FIG. 3 or variants thereof. In some embodiments, the $V_H$ comprises the amino acid sequence from the beginning of the CDR1 to the end of the CDR3 of any one of the heavy chain of the foregoing antibodies.

In one embodiment, the target specific antibody comprises a heavy chain CDR1, CDR2 or CDR3, each of which are independently selected from the CDR1, CDR2 and CDR3 regions of an antibody having a heavy chain variable region comprising the amino acid sequence of the $V_H$ region set out in SEQ ID NOs: 1, 3, 5, 7, 9 and 11, or encoded by a nucleic acid molecule encoding the $V_H$ region set out in SEQ ID NO: 13, 15, 17, 19 and 21. It is further contemplated that a target specific antibody comprises a heavy chain CDR1, CDR2 or CDR3, each of which are independently selected from the CDR1, CDR2 and CDR3 regions of an antibody having a heavy chain variable region comprising the amino acid sequence of the $V_H$ region set out in SEQ ID NOs: 23-33. In one aspect the heavy chain CDRs are located according to Chlothia numbering set out in FIG. 1: CDR1 is from approximately residues 31-35, CDR2 is from approximately residues 50-65 and CDR3 extends from approximately residues 95-102. A polypeptide of the target specific antibody may comprise the CDR1, CDR2 and CDR3 regions of an antibody comprising the amino acid sequence of the $V_H$ region selected from the group consisting of XPA061, XPA063, XPA065, XPA067, and XPA081.

In another embodiment, the antibody comprises a light chain as disclosed above and a heavy chain as disclosed above.

It is contemplated that a variant of the antibody sequence refers to amino acid sequences, comprising a variable heavy chain or a variable light chain amino acid sequence which is at least 60, 65, 70, 75, 80, 85, 90, 91, 92, 93, 94, 95, 96, 97, 98, or 99% homologous to any of the amino acid sequences set forth herein.

It is further contemplated that the CDR of the antibody heavy and light chains comprise variant amino acid sequences which may improve antibody binding affinity and are derived through, for example, affinity maturation. In one aspect it is contemplated that an antibody of the invention comprises a heavy chain CDR2 sequence having about 35% identity to a CDR2 of a parent antibody sequence set out in SEQ ID NOs: 1, 3, 5, 7, 9, 11 or 23-33. In a related aspect it is contemplated that an antibody of the invention comprises a heavy chain CDR3 sequence having about 50% identity to a CDR3 of a parent antibody sequence set out in SEQ ID NOs: 1, 3, 5, 7, 9, 11 or 23-33.

Antibody Nucleic Acids of the Invention

The present invention also encompasses nucleic acid molecules encoding target specific antibodies. In some embodiments, different nucleic acid molecules encode a heavy chain variable region and a light chain variable region of a target specific antibody. In other embodiments, the same nucleic acid molecule encodes a heavy chain and a light chain variable regions of a target specific antibody.

In one embodiment, the nucleic acid encodes a target specific antibody of the invention.

In one aspect, a nucleic acid molecule of the invention comprises a nucleotide sequence that encodes the $V_L$ amino acid sequence of antibodies XPA061, XPA063, XPA065, XPA067, and XPA081 set out in SEQ ID NOs: 2, 4, 6, 8 and 10 or a portion thereof. In a related aspect, the $V_L$ amino acid sequence is a consensus sequence set out in SEQ ID NO: 12. In some embodiments, the nucleic acid encodes the amino acid sequence of the light chain CDRs of said antibody. In some embodiments, said portion is a contiguous portion comprising CDR1-CDR3. In one embodiment, said portion comprises at least one, two or three of a light chain CDR1, CDR2, or CDR3 region.

In a related aspect, the nucleic acid molecule comprises a nucleotide sequence that encodes the light chain amino acid sequence of one of SEQ ID NOs: 2, 4, 6, 8, 10 and 12 or a portion thereof. In one embodiment, the nucleic acid molecule comprises the light chain nucleotide sequence of any one of SEQ ID NOs: 14, 16, 18, and 22 or a portion thereof.

In some embodiments, the nucleic acid molecule encodes a $V_L$ amino acid sequence that is at least 60, 65, 70, 75, 80, 85, 90, 91, 92, 93, 94, 95, 96 97, 98 or 99% identical to a $V_L$ amino acid sequence set out in SEQ ID NOs: 2, 4, 6, 8, 10 and 12. Nucleic acid molecules of the invention include nucleic acids that hybridize under highly stringent conditions, such as those described herein, to a nucleic acid sequence encoding the light chain variable region amino acid sequence of SEQ ID NOs: 2, 4, 6, 8, 10 and 12, or that has the light chain variable region nucleic acid sequence of SEQ ID NOs: 14, 16, 18, 20 and 22.

It is further contemplated that a nucleic acid molecule of the invention comprises a nucleotide sequence that encodes the $V_H$ amino acid sequence of any one of antibodies XPA061, XPA063, XPA065, XPA067, and XPA081, or a portion thereof. In some embodiments, the nucleic acid encodes the amino acid sequence of the heavy chain CDRs of said antibody. In some embodiments, said portion is a contiguous portion comprising heavy chain CDR1-CDR3. In one embodiment, said portion comprises at least one, two or three of a heavy chain CDR1, CDR2, or CDR3 region.

In a related aspect, the nucleic acid molecule comprises a nucleotide sequence that encodes the heavy chain amino acid sequence of one of heavy chain of SEQ ID NOs: 1, 3, 5, 7, 9 and 11 or a portion thereof. In one embodiment, the nucleic acid molecule comprises the heavy chain nucleotide sequence of SEQ ID NO: 13, 15, 17, 19 and 21 a portion thereof.

In some embodiments, the nucleic acid molecule encodes a $V_H$ amino acid sequence that is at least 70%, 75%, 80%, 85%, 90%, 95%, 96%, 97%, 98% or 99% identical to a $V_H$ amino acid sequence XPA061, XPA063, XPA065, XPA067, and XPA081 set out in SEQ ID NOs: 1, 3, 5, 7 and 9. In a related aspect, the $V_H$ amino acid sequence is a consensus sequence set out in SEQ ID NO: 11. Nucleic acid molecules of the invention include nucleic acids that hybridize under highly stringent conditions, such as those described above, to a nucleic acid sequence encoding the heavy chain variable region amino acid sequence of SEQ ID NOs: 1, 3, 5, 7, 9 and 11, or that has the heavy chain variable region nucleic acid sequence of any one of SEQ ID NO: 13, 15, 17, 19 and 21.

It is further contemplated that the nucleic acids of the invention encode a full-length light chain or heavy chain of an antibody selected from XPA061, XPA063, XPA065, XPA067, and XPA081 wherein a full-length light chain or full-length heavy chain comprises a light chain constant region or a heavy chain constant region, respectively.

In one aspect, the full length light chain antibody comprises the sequences set out in SEQ ID NOs: 2, 4, 6, 8, 10 and 12. It is further contemplated that the nucleotide encoding the full-length light chain encodes the sequences SEQ ID NOs: 2, 4, 6, 8, 10 and 12, and comprises the nucleotides sequence set forth in SEQ ID NOs: 14, 16, 18, 20 and 22.

In one aspect, the full length heavy chain antibody comprises the sequences in any one of SEQ ID NOs: 1, 3, 5, 7, 9 and 11. It is further contemplated that the nucleotide encoding the full-length heavy chain encodes the sequences heavy chain of SEQ ID NOs: 1, 3, 5, 7, 9 and 11 and comprises the nucleotides sequence set forth in any one of SEQ ID NO: 13, 15, 17, 19 and 21.

Polyclonal Antibodies

Polyclonal antibodies are preferably raised in animals by multiple subcutaneous (sc) or intraperitoneal (ip) injections of the relevant antigen and an adjuvant. An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg or 5 μg of the protein or conjugate (for rabbits or mice, respectively) with 3 volumes of Freund's: complete adjuvant and injecting the solution intradermally at multiple sites. One month later, the animals are boosted with ⅕ to {fraction (1/10)} the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibody refers to an antibody obtained from a population of substantially homogeneous antibodies. Monoclonal antibodies are generally highly specific, and may be directed against a single antigenic site, in contrast to conventional (polyclonal) antibody preparations that typically include different antibodies directed against different determinants (epitopes). In addition to their specificity, the monoclonal antibodies are advantageous in that they are synthesized by the homogeneous culture, uncontaminated by other immunoglobulins with different specificities and characteristics.

Monoclonal antibodies to be used in accordance with the present invention may be made by the hybridoma method first described by Kohler et al., (Nature, 256:495-7, 1975), or may be made by recombinant DNA methods (see, e.g., U.S. Pat. No. 4,816,567). The monoclonal antibodies may also be isolated from phage antibody libraries using the techniques described in, for example, Clackson et al., (Nature 352:624-628, 1991) and Marks et al., (J. Mol. Biol. 222:581-597, 1991).

In the hybridoma method, a mouse or other appropriate host animal, such as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromycloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, DMEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis; or affinity chromatography.

It is further contemplated that antibodies of the invention may be used as smaller antigen binding fragments of the antibody well-known in the art and described herein.

Antibody Fragments

Antibody fragments comprise a portion of an intact full length antibody, preferably an antigen binding or variable region of the intact antibody. Examples of antibody fragments include Fab, Fab', F(ab')$_2$, and Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; $V_{HH}$ containing antibodies; and other polypeptides formed from antibody fragments.

Papain digestion of antibodies produces two identical antigen-binding fragments, called "Fab" fragments, monovalent fragments consisting of the $V_L$, $V_H$, $C_L$ and $C_H$ domains each with a single antigen-binding site, and a residual "Fc" fragment, whose name reflects its ability to crystallize readily. Pepsin treatment yields a F(ab')$_2$ fragment, a bivalent fragment comprising two Fab fragments linked by a disulfide bridge at the hinge region, that has two "Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the Fv to form the desired structure for antigen binding, resulting in a single-chain antibody (scFv), in which a $V_L$ and $V_H$ region are paired to form a monovalent molecule via a synthetic linker that enables them to be made as a single protein chain (Bird et al., Science 242:423-426, 1988, and Huston et al., Proc. Natl. Acad. Sci. USA. 85:5879-5883, 1988). For a review of sFv see Pluckthun, in The Pharmacology of Monoclonal Antibodies, vol. 113, Rosenburg and Moore eds., Springer-Verlag, New York, pp. 269-315 (1994). An Fd fragment consists of the $V_H$ and $C_H1$ domains.

Additional antibody fragment include a domain antibody (dAb) fragment (Ward et al., Nature 341:544-546, 1989) which consists of a $V_H$ domain. Diabodies are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., *Proc. Natl. Acad. Sci. USA* 90:6444-6448, 1993, and Poljak et al., *Structure* 2:1121-1123, 1994). Diabodies can be bispecific or monospecific.

Functional heavy-chain antibodies devoid of light chains are naturally occurring in nurse sharks (Greenberg et al., *Nature* 374:168-73, 1995), wobbegong sharks Outtall et al., *Mol Immunol.* 38:313-26, 2001) and *Camelidae* (Hamers-Casterman et al., *Nature* 363: 446-8, 1993; Nguyen et al., *J. Mol. Biol.* 275: 413, 1998), such as camels, dromedaries, alpacas and llamas. The antigen-binding site is reduced to a single domain, the $V_{HH}$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains. Camelid $V_{HH}$ domains have been found to bind to antigen with high affinity (Desmyter et al., *J. Biol. Chem.* 276:26285-90, 2001) and possess high stability in solution (Ewert et al., *Biochemistry* 41:3628-36, 2002). Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Methods for generating antibodies having camelid heavy chains are described in, for example, in U.S. Patent Publication Nos. 20050136049 and 20050037421.

Because the variable domain of the heavy-chain-antibodies is the smallest fully functional antigen-binding fragment with a molecular mass of only 15 kDa, this entity is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods as described in Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

A "minibody" consisting of scFv fused to CH3 via a peptide linker (hingeless) or via an IgG hinge has been described in Olafsen, et al., Protein Eng Des Sel. 2004 April; 17(4):315-23.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med. Hypotheses.* 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

Thus, a variety of compositions comprising one, two, and/or three CDRs of a heavy chain variable region or a light chain variable region of an antibody may be generated by techniques known in the art.

Multispecific Antibodies

In some embodiments, it may be desirable to generate multispecific (e.g. bispecific) anti-target antibody of the invention having binding specificities for at least two different epitopes of the same or different molecules. Exemplary bispecific antibodies may bind to two different epitopes of the target molecule. Alternatively, a target-specific antibody arm may be combined with an arm which binds to a cell surface molecule, such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target. Bispecific antibodies may also be used to localize cytotoxic agents to cells which express or take up the target. These antibodies possess a target-binding arm and an arm which binds the cytotoxic agent (e.g., saporin, anti-interferon-60, vinca alkaloid, ricin A chain, methotrexate or radioactive isotope hapten). Bispecific antibodies can be prepared as full length antibodies or antibody fragments (e.g., F(ab')2 bispecific antibodies).

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., (*Science* 229:81-83, 1985)

describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from E. coli can be chemically coupled in vitro to form bispecific antibodies. (Shalaby et al., J. Exp. Med. 175:217-225 (1992))

Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispeefic antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. (Kostelny et al., J. Immunol. 148:1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. (Proc. Natl. Acad. Sci. USA 90:6444-48, 1993) has provided an alternative mechanism for making bispecific antibody fragments.

The fragments comprise a heavy chain variable region ($V_H$) connected to a light-chain variable region ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol. 152: 5368 (1994).

Alternatively, the bispecific antibody may be a "linear antibody" produced as described in Zapata et al. Protein Eng. 8:1057-62 (1995). Linear antibodies comprise a pair of tandem Fd segments ($V_H$-$C_H$1-$V_H$-$C_H$1) which form a pair of antigen binding regions. Linear antibodies can be bispecific or monospecific.

In a further embodiment, the bispecific antibody may be a chelating recombinant antibody (CRAb). A chelating recombinant antibody recognizes adjacent and non-overlapping epitopes of the target antigen, and is flexible enough to bind to both epitopes simultaneously (Neri et al., J Mol. Biol. 246: 367-73, 1995).

Antibodies with more than two valencies are also contemplated. For example, trispecific antibodies can be prepared. (Tutt et al., J. Immunol. 147:60, 1991).

Chimeric and Humanized Antibodies

Because chimeric or humanized antibodies are less immunogenic in humans than the parental mouse monoclonal antibodies, they can be used for the treatment of humans with far less risk of anaphylaxis. Thus, these antibodies may be preferred in therapeutic applications that involve in vivo administration to a human.

In particular, a rodent antibody on repeated in vivo administration in man, either alone or as a conjugate, will bring about an immune response in the recipient against the rodent antibody; the so-called HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like.

Chimeric monoclonal antibodies, in which the variable Ig domains of a mouse monoclonal antibody are fused to human constant Ig domains, can be generated using standard procedures known in the art (See Morrison et al., Proc. Natl. Acad. Sci. USA 81, 6841-6855 (1984); and, Boulianne et al, Nature 312, 643-646, (1984)). Although some chimeric monoclonal antibodies have proved less immunogenic in humans, the mouse variable Ig domains can still lead to a significant human anti-mouse response.

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., Nature 321:522 525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31:169-217 (1994); and Kettleborough et al., Protein Eng. 4:773-83 (1991) each of which is incorporated herein by reference.

CDR grafting involves introducing one or more of the six CDRs from the mouse heavy and light chain variable Ig domains into the appropriate four framework regions of human variable Ig domains. This technique (Riechmann, et al., Nature 332:323-27 (1988)), utilizes the conserved framework regions (FR1-FR4) as a scaffold to support the CDR loops which are the primary contacts with antigen. A disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co et al., J. Immunol. 152, 2968-2976 (1994)).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody.

HUMAN ENGINEERING™

HUMAN ENGINEERING™ of antibody variable domains has been described by Studnicka [See, e.g., Studnicka et al. U.S. Pat. No. 5,766,886; Studnicka et al., (*Protein Engineering* 7: 805-814, 1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position.

Variable regions of the light and heavy chains of a rodent antibody are HUMAN ENGINEERED™ as follows to substitute human amino acids at positions determined to be unlikely to adversely effect either antigen binding or protein folding, but likely to reduce immunogenicity in a human environment. Amino acid residues that are at "low risk" positions and that are candidates for modification according to the method are identified by aligning the amino acid sequences of the rodent variable regions with a human variable region sequence. Any human variable region can be used, including an individual $V_H$ or $V_L$ sequence or a human consensus $V_H$ or $V_L$ sequence or an individual or consensus human germline sequence. The amino acid residues at any number of the low risk positions, or at all of the low risk positions, can be changed. For example, at each low risk position where the aligned murine and human amino acid residues differ, an amino acid modification is introduced that replaces the rodent residue with the human residue. Alternatively, the amino acid residues at all of the low risk positions and at any number of the moderate risk positions can be changed. Ideally, to achieve the least immunogenicity all of the low and moderate risk positions are changed from rodent to human sequence.

Synthetic genes containing modified heavy and/or light chain variable regions are constructed and linked to human γ heavy chain and/or κ light chain constant regions. Any human heavy chain and light chain constant regions may be used in combination with the HUMAN ENGINEERED™ antibody variable regions, including IgA (of any subclass, such as IgA1 or IgA2), IgD, IgE, IgG (of any subclass, such as IgG1, IgG2, IgG3, or IgG4), or IgM. The human heavy and light chain genes are introduced into host cells, such as mammalian cells, and the resultant recombinant immunoglobulin products are obtained and characterized.

Human Antibodies from Transgenic Animals

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851 (1996)), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (*Cloning Stem Cells.* 4:91-102 (2002)) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TCMOUSE™ with various human antigens produces antibody responses comprising human antibodies.

See also Jakobovits et al., *Proc. Natl. Acad. Sci. USA,* 90:2551 (1993); Jakobovits et al., *Nature,* 362:255-258 (1993); Bruggemann et al., *Year in Immunol.,* 7:33 (1993); and U.S. Pat. No. 5,591,669, U.S. Pat. No. 5,589,369, U.S. Pat. No. 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

The invention contemplates a method for producing target-specific antibody or antigen-binding portion thereof comprising the steps of synthesizing a library of human antibodies on phage, screening the library with target protein or a portion thereof, isolating phage that bind target, and obtaining the antibody from the phage. By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the invention may be obtained in this way.

Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the invention can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum. Antibod. Hybridomas* 3:81-85; Huse et al. (1989) *Science* 246:1275-1281; McCafferty et al., *Nature* (1990) 348:552-554; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc Acid Res* 19:4133-4137; and Barbas et al. (1991) *Proc. Natl. Acad. Sci. USA* 89:7978-7982.

In one embodiment, to isolate human antibodies specific for the target antigen with the desired characteristics, a human $V_H$ and $V_L$ library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (*Nature* 348:552-554 (1990)); and Griffiths et al., (*EMBO J.* 12:725-734 (1993)). The scFv antibody libraries preferably are screened using target protein as the antigen.

Alternatively, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol*, 222:581-597 (1991); U.S. Pat. Nos. 5,565,332 and 5,573,905; Clackson, T., and Wells, J. A., *TIBTECH* 12, 173-184 (1994)). In particular, in vitro selection and evolution of antibodies derived from phage display libraries has become a powerful tool (See Burton, D. R., and Barbas III, C. F., *Adv. Immunol.* 57, 191-280 (1994); Winter, G., et al., *Annu. Rev. Immunol.* 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178:187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, Ike, ZJ/Z, Ff and one of the class II phages Xf, Pf1 and Pf3. The phage may be M13; or fd or a derivative thereof.

Once initial human $V_L$ and $V_H$ segments are selected, "mix and match" experiments, in which different pairs of the initially selected $V_L$ and $V_H$ segments are screened for target binding, are performed to select preferred $V_L/V_H$ pair combinations. Additionally, to further improve the quality of the antibody, the $V_L$ and $V_H$ segments of the preferred $V_L/V_H$ pair(s) can be randomly mutated, preferably within the any of the CDR1, CDR2 or CDR3 region of $V_H$ and/or $V_L$, in a process analogous to the in vivo somatic mutation process responsible for affinity maturation of antibodies during a natural immune response. This in vitro affinity maturation can be accomplished by amplifying $V_L$ and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to target antigen.

Following screening and isolation of an target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (Bio/Technology, 10:779-783 (1992)).

Methods for display of peptides on the surface of yeast and microbial cells have also been used to identify antigen specific antibodies. See, for example, U.S. Pat. No. 6,699,658. Antibody libraries may be attached to yeast proteins, such as agglutinin, effectively mimicking the cell surface display of antibodies by B cells in the immune system.

In addition to phage display methods, antibodies may be isolated using ribosome mRNA display methods and microbial cell display methods. Selection of polypeptide using ribosome display is described in Hanes et al., (Proc. Natl. Acad Sci USA, 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Amino Acid Sequence Variants

It is contemplated that modified polypeptide compositions comprising one, two, three, four, five, and/or six CDRs of an antibody are generated, wherein a CDR is altered to provide increased specificity or affinity to the target molecule. Sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see e.g. Sambrook et al., Molecular Cloning: A Laboratory Manual, 2nd Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

Antibody substances comprising the modified CDRs are screened for binding affinity for the original antigen. Additionally, the antibody or polypeptide is further tested for its ability to neutralize the activity of the target antigens. For example, antibodies of the invention may be analyzed as set out in the Examples to determine their ability to interfere with the biological activity of target antigen.

Modifications may be made by conservative or non-conservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the invention are described in greater detail below.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody (including antibody fragment) fused to an epitope tag or a salvage receptor epitope. Other insertional variants of the antibody molecule include the fusion to a polypeptide which increases the serum half-life of the antibody, e.g. at the N-terminus or C-terminus.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu hemagglutinin (HA) tag polypeptide and its antibody 12CA5 (Field et al., Mol. Cell. Biol. 8: 2159-2165 (1988));

the c-myc tag and the 8F9, 3C7, 6E10, G4, B7 and 9E10 antibodies thereto (Evan et al., *Mol. Cell. Biol.* 5:3610-16 (1985)); and the Herpes Simplex virus glycoprotein D (gD) tag and its antibody (Paborsky et al., *Protein Engineering* 3:547-53 (1990)). Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Non-conservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Affinity Maturation

Affinity maturation generally involves preparing and screening antibody variants that have substitutions within the CDRs of a parent antibody and selecting variants that have improved biological properties such as binding affinity relative to the parent antibody. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68 (1996)), and saturation mutagenesis (Nishimiya et al., *J. Biol. Chem.* 275:12813-20 (2000); Chowdhury, P. S. *Methods Mol. Biol.* 178, 269-85 (2002)) are typical examples of stochastic mutagenesis methods (Rajpal et al., *Proc Natl Acad Sci USA.* 102:8466-71 (2005)). Non-stochastic techniques often use alanine-scanning or site-directed mutagenesis to generate limited collections of specific variants. Some methods are described in further detail below.

Affinity Maturation Via Panning Methods

Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71 (2001)). Methods of affinity maturation using phage display technologies are described elsewhere herein and known in the art (see e.g., Daugherty et al., *Proc Natl Acad Sci USA.* 97:2029-34 (2000)).

Look-Through Mutagenesis

Look-through mutagenesis (LTM) (Rajpal et al., *Proc Natl Acad Sci USA.* 102:8466-71 (2005)) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all variants. After positive selection, clones with improved binding are sequenced, and beneficial mutations are mapped.

Error-Prone PCR

Error-prone PCR involves the randomization of nucleic acids between different selection rounds. The randomization occurs at a low rate by the intrinsic error rate of the polymerase used but can be enhanced by error-prone PCR (Zaccolo et al., *J. Mol. Biol.* 285:775-783 (1999)) using a polymerase having a high intrinsic error rate during transcription (Hawkins et al., *J Mol Biol.* 226:889-96 (1992)). After the mutation cycles, clones with improved affinity for the antigen are selected using routine methods in the art.

DNA Shuffling

Nucleic acid shuffling is a method for in vitro or in vivo homologous recombination of pools of shorter or smaller polynucleotides to produce variant polynucleotides. DNA shuffling has been described in U.S. Pat. No. 6,605,449, U.S. Pat. No. 6,489,145, WO 02/092780 and Stemmer, *Proc. Natl. Acad. Sci. USA,* 91:10747-51 (1994). Generally, DNA shuffling is comprised of 3 steps: fragmentation of the genes to be shuffled with DNase I, random hybridization of fragments and reassembly or filling in of the fragmented gene by PCR in the presence of DNA polymerase (sexual PCR), and amplification of reassembled product by conventional PCR.

DNA shuffling differs from error-prone PCR in that it is an inverse chain reaction. In error-prone PCR, the number of polymerase start sites and the number of molecules grows exponentially. In contrast, in nucleic acid reassembly or shuffling of random polynucleotides the number of start sites and the number (but not size) of the random polynucleotides decreases over time.

In the case of an antibody, DNA shuffling allows the free combinatorial association of all of the CDR1s with all of the CDR2s with all of the CDR3s, for example. It is contemplated that multiple families of sequences can be shuffled in the same reaction. Further, shuffling generally conserves the relative order, such that, for example, CDR1 will not be found in the position of CDR2. Rare shufflants will contain a large number of the best (e.g. highest affinity) CDRs and these rare shufflants may be selected based on their superior affinity.

The template polynucleotide which may be used in DNA shuffling may be DNA or RNA. It may be of various lengths depending on the size of the gene or shorter or smaller polynucleotide to be recombined or reassembled. Preferably, the template polynucleotide is from 50 bp to 50 kb. The template polynucleotide often should be double-stranded.

It is contemplated that single-stranded or double-stranded nucleic acid polynucleotides having regions of identity to the template polynucleotide and regions of heterology to the template polynucleotide may be added to the template polynucleotide, during the initial step of gene selection. It is also contemplated that two different but related polynucleotide templates can be mixed during the initial step.

Alanine Scanning

Alanine scanning mutagenesis can be performed to identify hypervariable region residues that contribute significantly to antigen binding. Cunningham and Wells, (*Science* 244:1081-1085 (1989)). A residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution.

Computer-Aided Design

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Altered Glycosylation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Also contemplated are antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., *Biotechnol Bioeng.* 87:614-22 (2004)). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., *Mol Immunol.* 26:1113-23 (1989)). Some host cell strains, e.g. Lec13 or rat hybridoma YB2/0 cell line naturally produce antibodies with lower fucosylation levels. (Shields et al., *J Biol. Chem.* 277:26733-40 (2002); Shinkawa et al., *J Biol Chem.* 278:3466-73 (2003)). An increase in the level of bisected carbohydrate, e.g. through recombinantly producing antibody in cells that overexpress GnTIII enzyme, has also been determined to increase ADCC activity (Umana et al., *Nat. Biotechnol.* 17:176-80 (1999)). It has been predicted that the absence of only one of the two fucose residues may be sufficient to increase ADCC activity (Ferrara et al., *Biotechnol Bioeng.* 93:851-61 (2006)).

Variants with Altered Effector Function

Other modifications of the antibody are contemplated. In one aspect, it may be desirable to modify the antibody of the invention with respect to effector function, for example, to enhance the effectiveness of the antibody in treating cancer. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., (*J. Exp Med.* 176: 1191-1195 (1992)) and Shopes, B. (*J. Immunol.* 148: 2918-2922 (1992)). Homodimeric antibodies with enhanced anti-tumor activity may also be prepared using heterobifunctional cross-linkers as described in Wolff et al., (*Cancer Research* 53: 2560-2565 (1993)). Alternatively, an antibody can be engineered which has dual Fc regions and may thereby have enhanced complement lysis and ADCC capabilities. See Stevenson et al., (*Anti-Cancer Drug Design* 3: 219-230 (1989)). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., (*Proc Natl Acad Sci USA.* 85:4852-56 (1998)), which described chimeric antibodies wherein a murine variable region was joined with human gamma 1, gamma 2, gamma 3, and gamma 4 constant regions.

In certain embodiments of the invention, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also International applications WO 97/34631 and WO 96/32478 which describe Fc variants and their interaction with the salvage receptor.

Thus, antibodies of the invention may comprise a human Fc portion, a human consensus Fc portion, or a variant thereof that retains the ability to interact with the Fc salvage receptor, including variants in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Sammay et al., *Molec. Immunol* 29:633-9 (1992)].

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g., Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor IIIA. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., (*J. Biol. Chem.*, 276:6591-604 (2001)), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine; a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA. See also Presta et al., (*Biochem. Soc. Trans.* 30:487-490, 2001), incorporated herein by reference in its entirety, which described several positions in the Fc region of IgG1 were found which improved binding only to specific Fc gamma receptors (R) or simultaneously improved binding to one type of Fc gamma R and reduced binding to another type. Selected IgG1 variants with improved binding to Fc gamma RIIIa were then tested in an in vitro antibody-dependent cellular cytotoxicity (ADCC) assay and showed an enhancement in ADCC when either peripheral blood mononuclear cells or natural killer cells were used.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes variants with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII.

U.S. Pat. No. 5,624,821, incorporated by reference herein in its entirety, reports that C1q binding activity of an murine antibody can be altered by mutating amino acid residue 318, 320 or 322 of the heavy chain and that replacing residue 297 (Asn) results in removal of lytic activity.

U.S. Patent Publication No. 20040132101, incorporated by reference herein in its entirety, describes variants with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Chappel et al. (*Proc Natl Acad Sci USA.* 88:9036-40 (1991)), incorporated herein by reference in its entirety, report that cytophilic activity of IgG1 is an intrinsic property of its heavy chain CH2 domain. Single point mutations at any of amino acid residues 234-237 of IgG1 significantly lowered or abolished its activity. Substitution of all of IgG1 residues 234-237 (LLGG) into IgG2 and IgG4 were required to restore full binding activity. An IgG2 antibody containing the entire ELLGGP sequence (residues 233-238) was observed to be more active than wild-type IgG1.

Isaacs et al. (*J Immunol.* 161:3862-9 (1998)), incorporated herein by reference in its entirety, report that mutations within a motif critical for Fc gammaR binding (glutamate 233 to proline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Armour et al. (*Mol Immunol.* 40:585-93 (2003)), incorporated by reference herein in its entirety, identified IgG1 variants which react with the activating receptor, FcgammaRIIa, at least 10-fold less efficiently than wildtype IgG1 but whose binding to the inhibitory receptor, FcgammaRIIb, is only four-fold reduced. Mutations were made in the region of amino acids 233-236 and/or at amino acid positions 327, 330 and 331. See also WO 99/58572, incorporated by reference herein in its entirety.

Xu et al. (*J Biol Chem.* 269:3469-74 (1994)), incorporated by reference herein in its entirety, report that mutating IgG1 Pro331 to Ser markedly decreased C1q binding and virtually eliminated lytic activity. In contrast, the substitution of Pro for Ser331 in IgG4 bestowed partial lytic activity (40%) to the IgG4 Pro331 variant.

Schuurman et al. (*Mol Immunol.* 38:1-8 (2001)), incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys (SEQ ID NO: 34) to the IgG1 hinge sequence Cys-Pro-Pro-Cys (SEQ ID NO: 35) also markedly stabilizes the covalent interaction between the heavy chains.

Angal et al. (*Mol Immunol.* 30:105-8 (1993)), incorporated by reference herein in its entirety, report that mutating the serine at amino acid position 241 in IgG4 to proline (found at that position in IgG1 and IgG2) led to the production of a homogeneous antibody, as well as extending serum half-life and improving tissue distribution compared to the original chimeric IgG4.

Covalent Modifications

Covalent modifications of the antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$, to prepare labeled proteins for use in radioimmunoassay.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 and in Aplin and Wriston, (*CRC Crit. Rev. Biochem., pp.* 259-306 (1981)).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact.

Chemical deglycosylation is described by Hakimuddin, et al., (*Arch. Biochem. Biophys.* 259: 52 (1987)) and by Edge et al., (*Anal. Biochem.* 118: 131 (1981)). Enzymatic cleavage of carbohydrate moieties on antibodies can be achieved by the use of a variety of endo- and exo-glycosidases as described by Thotakura et al., (*Meth. Enzymol.* 138: 350 (1987)).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Derivatives

As stated above, derivative refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine. Derivatives of the antibody substance of the invention, such as a bispecific antibody, are also useful as therapeutic agents and may be produced by the method of the invention The conjugated moiety can be incorporated in or attached to an antibody substance either covalently, or through ionic, van der Waals or hydrogen bonds, e.g., incorporation of radioactive nucleotides, or biotinylated nucleotides that are recognized by streptavadin.

Polyethylene glycol (PEG) may be attached to the antibody substances to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the antibody substances of the invention via acylation or reductive alkylation through a natural or engineered reactive group on the PEG moiety (e.g., an aldehyde, amino, thiol, or ester group) to a reactive group on the antibody substance (e.g., an aldehyde, amino, or ester group). Addition of PEG moieties to antibody substances can be carried out using techniques well-known in the art. See, e.g., International Publication No. WO 96/11953 and U.S. Pat. No. 4,179,337.

Ligation of the antibody substance with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

An antibody may be administered in its "naked" or unconjugated form, or may be conjugated directly to other therapeutic or diagnostic agents, or may be conjugated indirectly to carrier polymers comprising such other therapeutic or diagnostic agents.

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

Conjugation of antibody moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate.

Alternatively, conjugated antibodies can be prepared by directly conjugating an antibody component with a therapeutic agent. The general procedure is analogous to the indirect method of conjugation except that a therapeutic agent is directly attached to an oxidized antibody component. For example, a carbohydrate moiety of an antibody can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Antibody Fusion Proteins

Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., (*Hum. Antibodies Hybridomas* 6:129 (1995)), describe a fusion protein that includes an F(ab')$_2$ fragment and a tumor necrosis factor alpha moiety.

Methods of making antibody-toxin fusion proteins in which a recombinant molecule comprises one or more antibody components and a toxin or chemotherapeutic agent also are known to those of skill in the art. For example, antibody-Pseudomonas exotoxin A fusion proteins have been described by Chaudhary et al., Nature 339:394 (1989), Brirlkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., It. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOTOOS. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such conjugates are ricin, abrin, ribonuclease, DNase I, Stapbylococcal enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, Calif.—A Cancer Journal for Clinicians 44:43 (1994). Other suitable toxins are known to those of skill in the art.

Antibodies of the present invention may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs (See, e.g., Massey, Nature 328: 457-458 (1987). Antibody-abzyme conjugates can be prepared as described herein for delivery of the abzyme to a tumor cell population.

The enzymes above can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (See, e.g., Neuberger et al., *Nature* 312: 604-608 (1984))

Recombinant Production of Antibodies

DNA encoding a monoclonal antibody of the invention may be isolated and sequenced from the hybridoma cell secreting the antibody using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mNA, preferably membrane-associated mRNA, and the library screened using probes specific for human immunoglobulin polypeptide gene sequences. Nucleotide probe reactions and other nucleotide hybridization reactions are carried out at conditions enabling the identification of polynucleotides which hybridize to each other under specified conditions.

One exemplary set of conditions is as follows: stringent hybridization at 42° C. in 50% formamide, 5×SSC, 20 mM Na.PO$_4$, pH 6.8; and washing in 1×SSC at 55° C. for 30 minutes. Formula for calculating equivalent hybridization conditions and/or selecting other conditions to achieve a desired level of stringency are well known. It is understood in the art that conditions of equivalent stringency can be achieved through variation of temperature and buffer, or salt concentration as described Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51

In a preferred embodiment, however, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described further herein and is also well-known in the art. See e.g., Dower et al., WO 91/17271, McCafferty et al., WO 92/01047, and Caton and Koprowski, (*Proc. Natl. Acad. Sci. USA,* 87:6450-54 (1990)), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

In an alternative embodiment, the amino acid sequence of an immunoglobulin of interest may be determined by direct protein sequencing. Suitable encoding nucleotide sequences can be designed according to a universal codon table.

Amino acid sequence variants of the desired antibody may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the antibody, such as changing the number or position of glycosylation sites.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The invention also provides isolated nucleic acid encoding antibodies of the invention, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

(1) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The signal sequence selected preferably is one that is recognized and processed (i.e., cleaved by a signal peptidase) by the host cell. If prokaryotic host cells do not recognize and process the native antibody signal sequence, the signal sequence may be substituted by a signal sequence selected, for example, from the group of the pectate lyase (e.g., peIB) alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO90/13646. In mammalian cell expression, mammalian signal sequences as well as viral secretory leaders, for example, the herpes simplex gD signal, are available.

The DNA for such precursor region is ligated in reading frame to DNA encoding the antibody.

(2) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins are useful for cloning vectors in mammalian cells. Generally, the origin of replication component is not needed for mammalian expression vectors (the SV40 origin may typically be used only because it contains the early promoter).

(3) Selective Marker Component

Expression and cloning vectors may contain a selective gene, also termed a selectable marker. Typical selection genes encode proteins that (a) confer resistance to antibiotics or other toxins, e.g., ampicillin, neomycin, methotrexate, tetracycline, G418, geneticin, histidinol, or mycophenolic acid (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the antibody-encoding nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody of the invention, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282: 39 (1979)). The trp1 gene provides a selection marker for a mutant strain of yeast lacking the ability to grow in tryptophan, for example, ATCC No. 44076 or PEP4-1. Jones, (*Genetics* 85:12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene. Ura3-deficient yeast strains are complemented by plasmids bearing the ura3 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* Van den Berg, (*Bio/Technology*, 8:135 (1990)). Stable multi-copy expression vectors for secretion of mature recombinant human serum albumin by industrial strains of *Kluyveromyces* have also been disclosed (Fleer et al, *Bio/Technology*, 9:968-975 (1991)).

(4) Promoter Component

Expression and cloning vectors usually contain a promoter that is recognized by the host organism and is operably linked to the antibody-encoding nucleic acid. Promoters suitable for use with prokaryotic hosts include the arabinose (e.g., arab) promoter phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as Abelson leukemia virus, polyoma virus, fowlpox virus, adenovirus (such as Adenovirus 2), bovine papilloma virus, avian sarcoma virus, most preferably cytomegalovirus, a retrovirus, hepatitis-D virus, Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297: 598-601 (1982) on expression of human β-interferon cDNA in mouse cells under the control of a thymidine kinase promoter from herpes simplex virus. Alternatively, the rous sarcoma virus long terminal repeat can be used as the promoter.

(5) Enhancer Element Component

Transcription of a DNA encoding the antibody of this invention by higher eukaryotes is often increased by inserting an enhancer sequence into the vector. Many enhancer sequences are known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein. Another is the mouse immunoglobulin light chain transcription terminator.

(7) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, tobacco, lemna, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (*Biol. Reprod.* 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind target.

(8) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., (*Meth. Enz.* 58: 44, 1979), Barnes et al., *Anal. Biochem.* 102: 255 (1980), U.S. Pat. Nos. 4,767,704; 4,657,866; 4,927,762; 4,560,655; or 5,122,469; WO90/03430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of Antibody

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (*Science* 240:1041-43, 1988; ICSU Short Reports 10:105 (1990); and *Proc. Natl. Acad. Sci. USA* 90:457-461 (1993) describe a procedure for isolating antibodies which are secreted to the periplasmic space of *E. coli*. [See also, (Carter et al., *Bio/Technology* 10:163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., *J. Immunol. Meth.* 62: 1-13, 1983). Protein G is recommended for all mouse isotypes and for human $\gamma 3$ (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Screening Methods

Effective therapeutics depend on identifying efficacious agents devoid of significant toxicity. Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

In one embodiment of the invention, methods of screening for antibodies which modulate the activity of a target antigen comprise contacting test antibodies with a target polypeptide and assaying for the presence of a complex between the antibody and the target ligand. In such assays, the ligand is typically labeled. After suitable incubation, free ligand is separated from that present in bound form, and the amount of free or uncomplexed label is a measure of the ability of the particular antibody to bind to the target ligand.

In another embodiment of the invention, high throughput screening for antibody fragments or CDRs having suitable binding affinity to a target polypeptide is employed. Briefly, large numbers of different small peptide test compounds are synthesized on a solid substrate. The peptide test antibodies are contacted with a target polypeptide and washed. Bound polypeptides are then detected by methods well known in the art. Purified antibodies of the invention can also be coated directly onto plates for use in the aforementioned drug screening techniques. In addition, non-neutralizing antibodies can be used to capture the target and immobilize it on the solid support.

Combination Therapy

If more than one antibody effective at binding to target antigen is identified, it is contemplated that two or more antibodies to different epitopes of the target antigen may be mixed such that the combination of antibodies together to provide still improved efficacy against a condition or disorder to be treated associated with the target polypeptide. Compositions comprising one or more antibody of the invention may be administered to persons or mammals suffering from, or predisposed to suffer from, a condition or disorder to be treated associated with the target polypeptide.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

A second agent may be other therapeutic agents, such as cytokines, growth factors, other anti-inflammatory agents, anti-coagulant agents, agents that will lower or reduce blood pressure, agents that will reduce cholesterol, triglycerides, LDL, VLDL, or lipoprotein (a) or increase HDL, agents that will increase or decrease levels of cholesterol-regulating proteins, anti-neoplastic drugs or molecules. For patients with a hyperproliferative disorder, such as cancer or a tumor, combination with second therapeutic modalities such as radiotherapy, chemotherapy, photodynamic therapy, or surgery is also contemplated.

It is contemplated the antibody of the invention and the second agent may be given simultaneously, in the same formulation. It is further contemplated that the agents are administered in a separate formulation and administered concurrently, with concurrently referring to agents given within 30 minutes of each other.

In another aspect, the second agent is administered prior to administration of the antibody composition. Prior administration refers to administration of the second agent within the range of one week prior to treatment with the antibody, up to 30 minutes before administration of the antibody. It is further contemplated that the second agent is administered subsequent to administration of the antibody composition. Subsequent administration is meant to describe administration from 30 minutes after antibody treatment up to one week after antibody administration.

It is further contemplated that when the antibody is administered in combination with a second agent, wherein the second agent is a cytokine or growth factor, or a chemotherapeutic agent, the administration also includes use of a radiotherapeutic agent or radiation therapy. The radiation therapy administered in combination with an antibody composition is administered as determined by the treating physician, and at doses typically given to patients being treated for cancer.

A cytotoxic agent refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the invention.

Chemotherapeutic agents contemplated for use with the antibodies of the invention include, but are not limited to those listed in Table I:

TABLE I

Alkylating agents
Nitrogen mustards mechlorethamine
cyclophosphamide
ifosfamide
melphalan
chlorambucil TABLE I-continued Nitrosoureas carmustine (BCNU)
lomustine (CCNU)
semustine (methyl-CCNU)
Ethylenimine/Methyl-melamine thriethylenemelamine (TEM)
triethylene thiophosphoramide
(thiotepa)
hexamethylmelamine
(HMM, altretamine)
Alkyl sulfonates busulfan
Triazines dacarbazine (DTIC)
Antimetabolites
Folic Acid analogs methotrexate
Trimetrexate
Pemetrexed
(Multi-targeted antifolate)
Pyrimidine analogs 5-fluorouracil
fluorodeoxyuridine
gemcitabine
cytosine arabinoside
(AraC, cytarabine)
5-azacytidine
2,2'-difluorodeoxy-cytidine
Purine analogs 6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents TABLE I-continued Antiandrogens flutamide
gonadotropin-releasing
hormone analogs
leuprolide
Nonsteroidal antiandrogens flutamide
Natural products
Antimitotic drugs
Taxanes paclitaxel
Vinca alkaloids
vinblastine (VLB)
vincristine
vinorelbine
Taxotere ® (docetaxel)
estramustine
estramustine phosphate
Epipodophylotoxins etoposide
teniposide
Antibiotics actimomycin D
daunomycin (rubido-mycin)
doxorubicin (adria-mycin)
mitoxantroneidarubicin
bleomycin
splicamycin (mithramycin)
mitomycinC
dactinomycin
aphidicolin
Enzymes L-asparaginase
L-arginase
Radiosensitizers metronidazole
misonidazole
desmethylmisotridazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinium coordination complexes cisplatin
Carboplatin
oxaliplatin
Anthracenedione
mitoxantrone
Substituted urea hydroxyurea
Methylhydrazine derivatives N-methylhydrazine (MIH)
procarbazine
Adrenocortical suppressant mitotane (o, p'- DDD)
ainoglutethimide
Cytokines interferon ($\alpha$, $\beta$, $\gamma$)
interleukin-2

TABLE I-continued

Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines
Radiation X-ray
ultraviolet light
gamma radiation
visible light
infrared radiation
microwave radiation Treatment of Disorders Using the Methods and Compositions of the Invention In another embodiment, the invention provides a method for inhibiting target activity by administering a target-specific antibody to a patient in need thereof. Any of the types of antibodies described herein may be used therapeutically. In exemplary embodiments, the target specific antibody is a human, chimeric or humanized antibody. In another exemplary embodiment, the target is human and the patient is a human patient. Alternatively, the patient may be a mammal that expresses a target protein that the target specific antibody cross-reacts with. The antibody may be administered to a non-human mammal expressing a target protein with which the antibody cross-reacts (i.e. a primate) for veterinary purposes or as an animal model of human disease. Such animal models may be useful for evaluating the therapeutic efficacy of target specific antibodies of the invention.

Exemplary conditions or disorders associated with target expression that can be treated with an antibody substance according to the present invention include cancers, such as pancreatic cancer, esophageal cancer, gastric cancer, colorectal cancer, and small lung cell carcinoma. Other conditions or disorders that may be treated using antibodies of the invention include, gastric ulcer, duodenal ulcer, other ulcers or conditions associated with *H. Pylori*, gastroesophageal reflux disease, autoimmune gastritis, atrophic body gastritis, Zollinger-Ellison syndrome associated with tumor of the pancreas (gastrinoma), and inflammatory bowel disease.

Gastrin expression and cell activation has been found in several models of pancreatic cancer (Smith et al., *Am J Physiol* 268 (1 Pt 2):R135-41 (1995)), gastric cancer ((Watson et al., *Br J Surg* 75:342-5 (1988)) (Watson, et al., *Br J Cancer* 59:554-8 (1989)) (Piontek and Hengels, *Anticancer Res* 13:715-20 (1993)) (Szabo et al., *J Physiol Paris*. 94:71-4 (2000)), and colorectal cancer (Ahmed et al., *FEBS Lett* 556: 199-203 (2004)) (Stepan et al., *Mol Med* 5:147-59 (1999)) (Smith et al., *Am J Physiol* 271 (3 Pt 2):R797-805 (1996)).

Pancreatic Cancer

Pancreatic cancer is the fifth leading cause of cancer death in the United States. Surgical resection remains the primary treatment since, on occasion, resection can lead to long-term survival and provides effective palliation. For decades, 5-fluorouracil (5-FU) was the most widely used chemotherapeutic agent in metastatic pancreatic cancer. Today, gemcitabine is the current standard of care for patients with locally advanced and metastatic pancreatic cancer (Tempero et al., *J Clin Oncol.* 21:3402-8 (2003)) (Berlin et al., *Clin Oncol*

20:3270-5 (2002)). The unique mechanism of action and favorable toxicity profile of gemcitabine have allowed exploration of many novel gemcitabine-based combination regimens as treatment for pancreatic cancer (see e.g., Rocha Lima et al., *J Clin Oncol* 20:1182-91 (2002)).

Gastric Cancer

Stomach cancer is the second leading cancer. Cure for gastric cancer is available, only for those patients in whom a complete surgical resection can be performed; this is possible for only 30% to 35% of all patients, and even in these patients, relapse is common. The level of lymph-node dissection is an important prognostic factor: when the en bloc lymph node dissection is performed, 5-year survival is nearly 40%, which is much better than that without lymph node dissection. The estimated 5-year relative survival rates by Stage are as follows: 65% for Stage I, 20% for Stage II, 10% for Stage III and <1% for Stage IV. Advanced disease is incurable and patients are treated by chemotherapy. Current thereapies for gastric cancer include FAM, a combination of 5-FU, mitomycin C, and low doses of doxorubicin (see e.g., Rougier et al., 1994), FAMTX (FAM with mitomycin replaced by a high dose of methotrexate), etoposide plus LV and 5-PU (i.e., ELF), and ECF (epirubicin plus 5-FU as a protracted infusion and cisplatin).

Colorectal cancer (commonly referred to as "colon" cancer) develops in the lower part of the digestive system, also referred to as the gastrointestinal, or GI, system. This cancer usually develops from precancerous changes or growths in the lining of the colon and rectum. Colon cancer accounts for about 10 percent of cancer deaths this year in the United States. Surgery is the most common form of treatment for colon cancer. For cancers that have not spread, it frequently controls the disease.

Chemotherapy or chemotherapy with radiation treatment is given before or after surgery to most patients whose cancer has spread into the bowel wall or to the lymph nodes. Treatments include, but are not limited to the following agents, alone or in combination with each other: 5Fluorouracil, docetaxel, Camptosar/Irinotecan, capecitabine, oxaliplatin, and anti-Vascular Endothelial Growth Factor antibody (AVASTIN®).

Small Lung Cell Carcinoma

Small lung cell carcinoma (SLCC), an aggressive (fast-growing) cancer that usually forms in tissues of the lung and spreads to other parts of the body, accounts for approximately 20% of all lung cancers. It is characterized by its origin in large central airways and histological composition of sheets of small cells with scanty cytoplasm. Small cell carcinoma is a tumor of neuroendocrine origin which metastasizes often. The cancer cells look small and oval-shaped when looked at under a microscope. Common treatments include surgery to remove the affected tissue, as well as radiation therapy and chemotherapy. Chemotherapeutic agents used to treat SLCC include, but are not limited to, etoposide, cisplatin, and vincristine.

Gastroesophageal Reflux Disease

Acid reflux irritates the walls of the esophagus, inducing a secondary peristaltic contraction of the smooth muscle, and may produce the discomfort or pain known as heartburn. Most episodes of acid reflux are asymptomatic. Secondary peristalsis returns approximately 90% of the acid and food to the stomach. Digested food in the stomach chemically stimulates the release of gastrin from G cells located in the antrum of the stomach. Distention of the stomach causes release of acetylcholine from the vagus nerve, and this further stimulates the G cells to produce gastrin. Gastrin travels through the bloodstream and binds to the gastrin receptor on the parietal cells, located in the gastric body and fundus. When gastrin binds to its receptor, the parietal cell's permeability to calcium ions (Ca++) is altered so that the ions move into the cell. The intracellular increase in Ca++ activates the intracellular protein phosphokinases. The increase in protein phosphokinases results in the translocation of H+-K+-ATPase to the secretory canaliculus where the extracellular aspect of the pump is exposed to potassium ions (K+).

Some common treatments of GERD include antacids; foaming agents which coat the stomach; $H_2$ blockers, such as cimetidine, famotidine, nizatidine, and ranitidine, impede acid production; proton pump inhibitors such as omeprazole, lansoprazole, pantoprazole, rabeprazole, and esomeprazole; prokinetics, which help strengthen the esophageal sphincter and makes the stomach empty faster, such as bethanechol and metoclopramide;

Gastric and Duodenal Ulcer

A gastric ulcer is a break in the normal tissue lining the stomach. A duodenal ulcer is a break in the normal tissue lining the duodenum (the first part of the small bowel). Benign gastric ulcers are caused by an imbalance between the secretion of acid and an enzyme called pepsin and the defenses of the stomach's mucosal lining. For people with *Helicobacter pylori* infection, the main goal is eradication of the organism that causes the problem. Multiple regimens are effective and usually include either an H2 receptor antagonist such as famotidine or nizatidine, or a proton pump inhibitor such as omeprazole or esomeprazole to suppress acid, combined with antibiotics. For people without *H. pylori* infection, ulcer-healing medications such as antacids, H2 receptor antagonists, or proton pump inhibitors are usually effective. A vagotomy (cutting the vagus nerve, which controls the stomach's production of gastric acid) or a partial gastrectomy (removal of part of the stomach) may be necessary.

Autoimmune Gastritis

Autoimmune gastritis is associated with serum antiparietal and anti-intrinsic factor (IF) antibodies. The gastric corpus undergoes progressive atrophy, IF deficiency occurs, and patients may develop pernicious anemia. Two types of IF antibodies are detected, ie, types I and II. Type I IF antibodies block the IF-cobalamin binding site, thus preventing the uptake of vitamin B-12. Cell-mediated immunity also contributes to the disease. T-cell lymphocytes infiltrate the gastric mucosa and contribute to epithelial cell destruction and resulting gastric atrophy.

Atrophic Body Gastritis

Atrophic body gastritis (ABG) is characterized by atrophy of the gastric body mucosa, hypergastrinemia, and hypo/achlorhydria. Like autoimmune gastritis, it is association with pernicious anemia. Body gastritis is also associated with *H. pylori* infection and hypergastrinemia, or increased gastrin levels (Delle Fave et al., *Dig Liver Dis.* 34:270-8 (2002)).

Zollinger-Ellison syndrome (ZES) is a rare disorder that causes tumors in the pancreas and duodenum and ulcers in the stomach and duodenum. The tumors secrete gastrin which causes the stomach to produce too much acid causing stomach and duodenal ulcers (Gibril et al., *Curr Gastroenterol Rep.* 7:114-21 (2005)). The ulcers caused by ZES are less responsive to treatment than ordinary peptic ulcers. The primary treatment for ZES is medication to reduce the production of stomach acid, including proton pump inhibitors and H-2 blockers.

Inflammatory Bowel Disease

Inflammatory bowel disease includes two conditions known as ulcerative colitis (UC) and Crohn's disease (CD). Gastrin receptor expression is decreased in inflamed and non-inflamed colon of CD, but not in UC (ter Beek et al., *J Clin*

*Pathol.* 57:1047-51 (2004)). However, other studies have shown that the levels of serum gastrin are elevated in patients with Crohn's disease while patients with ulcerative colitis exhibited no significant differences compared to normal controls (Triantafillidis et al., *Hepatogastroenterology.* 50 Suppl 2:cccxv-cccxvii, (2003)).

In one embodiment, treatment of these disorders or conditions in an animal in need of said treatment, comprises administering to the animal an effective amount of a composition comprising an antibody substance of the invention.

The conditions treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Non-Therapeutic Uses

The antibodies of the invention may be used as affinity purification agents for target or in diagnostic assays for target protein, e.g., detecting its expression in specific cells, tissues, or serum. The antibodies may also be used for in vivo diagnostic assays. Generally, for these purposes the antibody is labeled with a radionuclide (such as $^{111}$In, $^{99}$Tc, $^{14}$C, $^{131}$I, $^{125}$I, $^{3}$H, $^{32}$P or $^{35}$S) so that the antibody can be localized using immunoscintiography.

The antibodies of the present invention may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label tissue or cell samples using methods known in the art.

The target specific antibodies can be used in a conventional immunoassay, including, without limitation, an ELISA, an RIA, FACS, tissue immunohistochemistry, Western blot or immunoprecipitation, which are all techniques well-known in the art. The antibodies of the invention can be used to detect target in humans and other mammals. The invention provides a method for detecting target in a biological sample comprising contacting a biological sample with a target specific antibody of the invention and detecting the bound antibody. In one embodiment, the target specific antibody is directly labeled with a detectable label. In another embodiment, the target specific antibody (the first antibody) is unlabeled and a second antibody or other molecule that can bind the target specific antibody is labeled. As is well known to one of skill in the art, a second antibody is chosen that is able to specifically bind the particular species and class of the first antibody. For example, if the target specific antibody is a human IgG, then the secondary antibody could be an anti-human-IgG. Other molecules that can bind to antibodies include, without limitation, Protein A and Protein G, both of which are available commercially, e.g., from Pierce Chemical Co.

It is contemplated that the immunoassays disclosed above are used for a number of purposes. For example, the target specific antibodies can be used to detect target in cells or on the surface of cells in cell culture, or secreted into the tissue culture medium. The target specific antibodies can be used to determine the amount of target on the surface of cells or secreted into the tissue culture medium that have been treated with various compounds. This method can be used to identify compounds that are useful to inhibit or activate target expression or secretion. According to this method, one sample of cells is treated with a test compound for a period of time while another sample is left untreated. If the total level of target is to be measured, the cells are lysed and the total target level is measured using one of the immunoassays described above. The total level of target in the treated versus the untreated cells is compared to determine the effect of the test compound.

Labels

In some embodiments, the antibody substance is labeled to facilitate its detection. A "label" or a "detectable moiety" is a composition detectable by spectroscopic, photochemical, biochemical, immunochemical, chemical, or other physical means. For example, labels suitable for use in the present invention include, radioactive labels (e.g., $^{32}$P), fluorophores (e.g., fluorescein), electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide.

Examples of labels suitable for use in the present invention include, but are not limited to, fluorescent dyes (e.g., fluorescein isothiocyanate, Texas red, rhodamine, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold, colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugation of an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The compounds of the invention can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means for detecting labels are well known to those of skill in the art. Thus, for example, where the label is radioactive, means for detection include a scintillation counter or photographic film, as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands can be used in the diagnosis of a disease or health condition.

Formulation of Pharmaceutical Compositions

To administer antibody substances of the invention to human or test animals, it is preferable to formulate the antibody substances in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds may form solvates with water or common organic solvents. Such solvates are contemplated as well.

The antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular intradermal or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Injection, especially intravenous, is preferred.

Pharmaceutical compositions of the present invention containing an antibody substance of the invention as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

Formulation of the pharmaceutical composition will vary according to the route of administration selected (e.g., solution, emulsion). An appropriate composition comprising the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

The antibodies of the invention can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of antibody is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known aft using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy-syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial an antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancer include for example, salicylate, glycocholate/linoleate, glycholate, aprotinin, bacitracin, SDS, caprate and the like. See, e.g., Fix (*J. Pharm. Sci.*, 85:1282-1285 (1996)) and Oliyai and Stella (*Ann. Rev. Pharmacol. Toxicol.*, 32:521-544 (1993)).

Antibody compositions contemplated for use to inhibit target activity, including binding of the target to its cognate receptor or ligand, target-mediated signaling, and the like. In particular, the compositions exhibit inhibitory properties at concentrations that are substantially free of side effects, and are therefore useful for extended treatment protocols. For example, co-administration of an antibody composition with another, more toxic, cytotoxic agent can achieve beneficial inhibition of a condition or disorder being treated, while effectively reducing the toxic side effects in the patient.

In addition, the properties of hydrophilicity and hydrophobicity of the compositions contemplated for use in the invention are well balanced, thereby enhancing their utility for both in vitro and especially in vivo uses, while other compositions lacking such balance are of substantially less utility. Specifically, compositions contemplated for use in the invention have an appropriate degree of solubility in aqueous media which permits absorption and bioavailability in the body, while also having a degree of solubility in lipids which permits the compounds to traverse the cell membrane to a putative site of action. Thus, antibody compositions contemplated are maximally effective when they can be delivered to the site of target antigen activity.

Administration and Dosing

In one aspect, methods of the invention include a step of administration of a pharmaceutical composition.

Methods of the invention are performed using any medically-accepted means for introducing a therapeutic directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the invention implanted near the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly or monthly.

Also contemplated in the present invention is the administration of multiple agents, such as an antibody composition in conjunction with a second agent as described herein.

The amounts of antibody composition in a given dosage will vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveal optimal dosages for particular disease states and patient populations.

It will also be apparent that dosing may be modified if traditional therapeutics are administered in combination with therapeutics of the invention.

Gene Therapy

The nucleic acid molecules of the present invention can be administered to a patient in need thereof via gene therapy. The therapy may be either in vivo or ex vivo. In one embodiment, nucleic acid molecules encoding both a heavy chain and a light chain are administered to a patient. In another embodiment, the nucleic acid molecules are administered such that they are stably integrated into chromosomes of B cells because these cells are specialized for producing antibodies. In a related embodiment, precursor B cells are transfected or infected ex vivo and re-transplanted into a patient in need thereof. In a further embodiment, precursor B cells or other cells are infected in vivo using a virus known to infect the cell type of interest.

Delivery of a functional gene encoding a polypeptide of the invention to appropriate cells is effected ex vivo, in situ, or in vivo by use of vectors, including viral vectors (e.g., adenovirus, adeno-associated virus, or a retrovirus), or ex vivo by use of physical DNA transfer methods (e.g., liposomes or chemical treatments). See, for example, Anderson, *Nature*, supplement to vol. 392, no. 6679, pp. 25-20 (1998). For additional reviews of gene therapy technology see Friedmann, (*Science*, 244: 1275-1281 (1989)); Verma, (*Scientifc American:* 263: 68-72, 81-84 (1990)); and Miller, (*Nature*, 357: 455-460 (1992)). Introduction of any one of the nucleotides of the present invention or a gene encoding a polypeptide of the invention can also be accomplished with extrachromosomal substrates (transient expression) or artificial chromosomes (stable expression). Cells may also be cultured ex vivo in the presence of proteins of the present invention in order to proliferate or to produce a desired effect on, or activity in, such cells. In another embodiment, cells comprising vectors expressing the polynucleotides or polypeptides of the invention may be cultured ex vivo and administered to an individual in need of treatment for overexpression of target protein.

In one aspect, the gene therapy method comprises the steps of administering an isolated nucleic acid molecule encoding the heavy chain or an antigen-binding portion thereof of a target specific antibody and expressing the nucleic acid molecule. In one embodiment, the gene therapy method comprises the steps of administering an isolated nucleic acid molecule encoding the light chain or an antigen-binding portion thereof of a target specific antibody and expressing the nucleic acid molecule. In another embodiment, the gene therapy method comprises the steps of administering an isolated nucleic acid molecule encoding the heavy chain or an antigen-binding portion thereof and an isolated nucleic acid molecule encoding the light chain or the antigen-binding portion thereof of a target specific antibody of the invention and expressing the nucleic acid molecules. The gene therapy method may also comprise the step of administering another second agent to the patient receiving gene therapy.

After infection either in vivo or ex vivo, levels of antibody expression can be monitored by taking a sample from the treated patient and using any immunoassay known in the art or discussed herein.

Kits

As an additional aspect, the invention includes kits which comprise one or more compounds or compositions packaged in a manner which facilitates their use to practice methods of the invention. In one embodiment, such a kit includes a compound or composition described herein (e.g., a composition comprising a target-specific antibody alone or in combination with a second agent), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the antibody composition.

Additional aspects and details of the invention will be apparent from the following examples, which are intended to be illustrative rather than limiting.

EXAMPLES

Example 1

Methods for Isolating Target-Specific Antibodies

To isolate a panel of antibodies able to neutralize the activity of the human growth factor gastrin, three human antibody phage display libraries, expressing either scFv or Fab fragments, were investigated in parallel. The target used for the library panning was a short 10 amino acid peptide from the N terminal portion of Gastrin 17. The peptide was biotinylated at its C-terminus and used in a soluble panning approach.

Selection of target specific antibody from phage display was carried out according to methods described by Marks et al. (*Methods Mol. Biol.* 248:161-76 (2004)). Briefly, the phage display library was incubated with 100 pmols of the biotinylated peptide at room temperature for 1 hr and the complex formed was then captured using 100 µl of Streptavidin beads suspension (DYNABEADS® M-280 Streptavidin, Invitrogen). Non specific phages were removed by washing the beads with wash buffer (PBS+5% Milk). Bound phages were eluted with 0.5 ml of 100 nM Triethyleamine (TEA) and immediately neutralized by addition of an equal volume of 1M TRIS-Cl pH 7.4. Eluted phage pool was used to infect TG1 *E coli* cells growing in logarithmic phase, and phagemid was rescued as described (Marks et al., *Methods Mol. Biol.* 248:161-76 (2004)). Selection was repeated for a total of three rounds. Single colonies obtained from TG1 cells infected with eluted phage from the third round of panning were screened for binding activity in an ELISA assay. Briefly, single colonies obtained from the TG1 cell infected with eluted phage were used to inoculate media in 96-well plates. Microcultures were grown to an $OD_{600}=0.6$ at which point expression of soluble antibody fragment was induced by addition of 1 mM IPTG following overnight culture in a shaker incubator at 30° C. Bacteria were spun down and periplasmic extract was prepared and used to detect antibody binding activity to biotinylated gastrin immobilized on Streptavidin microplates (REACT-BIND™ Streptavidin HBC, Pierce) following standard ELISA protocol provided by the microplate manufacturer.

Example 2

Methods for Off-Rate Ranking of Antibody Fragments

Thousands of binders were identified from the phage libraries, requiring an improved method of reducing the number of binders through a screening funnel. The screening funnel employed a high-throughput off-rate ranking method to allow rapid prioritization of peptide binders.

Clones were analyzed for their relative off-rate and relative mass bound to peptides using BIACORE®. Biotinylated peptides were captured on a Streptavidin sensor chip (BIA-CORE®). Peripreps containing the antibody fragments were injected over the chip, resulting in the binding of up to 1500 Response Units (RU). Raw data were transferred into Scrubber software, which was used to calculate dissociation rates of individual samples. The amount of sample bound to each test surface (specific, nonspecific, or no peptide) was calculated using BiaEval software. Samples which bound to control surfaces (streptavidin alone, or control peptide) at a ratio of approximately ⅓ that of specific peptides were eliminated from consideration, as were samples that resulted in <20 RU of binding to specific peptides. The remaining samples were ranked according to dissociation rates.

By focusing on clones with the slowest off-rates, the number of binders was narrowed to about 65 for purification and single-point cell-based functional assays. Cell based functional assays include measuring inhibition of gastrin-induced increases in intracellular calcium flux and detecting the levels of phosphorylation and activation of ERK1/2 (pERK1/2) in CCK2R expressing cells.

Example 3

Flow Cytometric Measurement of Intracellular Calcium Flux to Select for Neutralizing Antibodies to GPCRs Binding of gastrin to CCK2R results in phospholipase C (PLC)-mediated intracellular calcium flux. The primary functional assay for screening and characterization of target neutralizing antibodies employed flow cytometry and the fluorescent calcium indicator dyes Fluo-3 and Fura Red to measure target stimulated intracellular calcium flux in a CCK2R overexpressing cell line (AGS-TR). Because of their opposite responses to calcium binding, Fluo-3 increases in fluorescence while Fura Red decreases in fluorescence, and their different emission spectra, use of these dyes in combination results in generation of a pseudo-ratiometric signal that can reduce the influence of variables such as differences in cell size and intracellular dye concentration on the overall calcium flux response (Novak et al., Cytometry 17:135-141 (1994)). Real-time injection of stimulus during kinetic analysis was performed using the Cytek Time Zero Calcium Flux Measurement System.

Cell loading of AGS-TR cells with Fluo-3 AM and Fura Red AM was optimized for concentration, time, and temperature to ensure the highest possible signal in response to increases in intracellular calcium concentrations. Dye loaded cells were kept on ice until needed. Prior to analysis, cells were pre-incubated to 37° C. before addition of gastrin stimulant. Cells were acquired using the Cytek Time Zero calcium flux measurement system. Approximately 10 seconds of events were acquired prior to stimulus injection to establish a baseline. Upon stimulus injection, approximately 40 seconds of events were acquired to monitor the changes in intracellular calcium concentrations by detecting the changes in fluorescence of Fluo-3 and Fura Red.

Lead antibody selection to identify neutralizing antibodies follows the following screening cascade. Antibodies were initially screened for neutralization activity at a 100× molar excess over gastrin which is typically used at the EC50 concentration (1 nM) then further characterized at a lower concentration.

Mouse hybridoma-derived anti-gastrin antibodies (Aphton Corporation, Philadelphia, Pa.) and purified ELISA-positive phage display-derived anti-gastrin scFv and F(ab) fragments were screened for gastrin neutralizing activity at roughly 100 fold molar excess over gastrin (1 nM). Antibodies XPA061, XPA081, XPA065, XPA067 all demonstrated approximately 80% Ca flux neutralization in cells stimulated with gastrin. Antibodies XPA071, XPA063, XPA064, XPA088 and XPA0116 all showed greater than 70% neutralization. Antibodies XPA0122, XPA0121, XPA0120, XPA0119, XPA0118, XPA0123, PD-71, and XPA092 were identified as good neutralizers in a second screening round. Antibodies that showed over 70% neutralization of calcium flux were chosen for further study.

Candidates that neutralize at this threshold were further characterized at a lower concentration, e.g., 2× molar excess, to further differentiate the neutralization potencies of the antibodies. Antibody XPA061 exhibited approximately 70% neutralization when used at 2× molar excess, while antibody XPA0120 showed approximately 50% inhibition, XPA0121 and XPA088 both showed approximately 40% inhibition, XPA0118 and XPA064 showed slightly greater than 30% inhibition, and XPA0116, XPA0123 and XPA0119 demonstrated between 20 and 30% inhibition. The other antibodies gave under 20% neutralization.

These top candidates that showed a high degree of neutralization at lower concentrations were further analyzed in cell based functional assays and were selected for re-forming of antibody fragments to IgG as described below.

Example 4

ELISA Measurement of Neutralization of ERK1/2 Phosphorylation Using Antibodies to GPCRs Gastrin binding to CCK2R leads to activation of ERK1/2 (pERK1/2) in CCK2R expressing cells. In order to evaluate the effect of gastrin antibodies on downstream effects of gastrin-CCK2R binding, activation of ERK1/2 was measured in the presence of anti-gastrin antibodies.

Cells were seeded in microtiter plates in complete growth medium for 24 hours at 37° C. followed by 24 hour incubation in serum-free media to reduce basal levels of intracellular signaling. Cells were incubated with gastrin±potential neutralizing anti-gastrin antibodies for 5 minutes at 37° C. and immediately washed with ice cold PBS before addition of standard lysis buffer containing detergents, chelators, and various protease and phosphatase inhibitors to generate the cell lysates. The levels of phosphorylated ERK1/2 (pERK1/2) were measured using standard ELISA (i.e. DUOSET® IC Phospho-ERK1/ERK2, R&D Systems, Inc. or FACE™ ERK1/2, Active Motif). Results of pERK1/2 assay using select antibodies are shown in Table 2.

Example 5

Measurement of Anti-Proliferative/Apoptotic Activity of Neutralizing Antibodies to GPCRs To examine the effects of anti-gastrin antibodies on the growth and proliferation of CCK2R expressing cells, growth inhibition or cellular cytotoxicity as a consequence of antibody neutralization of gastrin is measured using well-known techniques in the art. Such techniques include staining with viability dyes to monitor metabolically active cells (i.e. MTT, XTT, and WST-1 assays), quantitating DNA synthesis monitoring incorporation of modified nucleotides (e.g., Brdu) or radiolabeled nucleotides (e.g., $^3$H-thymidine), or quantitating total cell numbers using DNA interacting dyes (e.g., CYQUANT™, Molecular Probes).

Induction of apoptosis as a consequence of antibody neutralization of gastrin is measured using well-known techniques in the art including monitoring increased extracellular exposure of phosphatidylserine (PS) as an early apoptotic marker using labeled Annexin V, activation of cellular caspase-3 using labeled substrates (e.g., DEVD-APC, R & D Systems, Inc.), or DNA fragmentation as measured by an increase in a sub-G0/G1 population in cell cycle analysis (e.g, BrdU Flow Kit, BD Biosciences).

Example 6

Converting Antibody Candidates Identified by Phage Display to Whole IgG

To convert the lead candidate binders from the initial screen to antibodies comprising antibody heavy and light chain constant regions, the variable regions of both heavy and light chains binders were cloned into a proprietary mammalian expression vector (WO 2004/033693) encoding for either the kappa (κ), lambda (λ) and gamma-2 (γ2) constant region genes.

Antibodies were transiently expressed in 293E cells as described in Handa et al (2004 American Society of Cancer Biology Poster #1937). Supernatant of transfected cells was harvested at day 6 of culture and IgG was quantified. IgG yield from the top five candidates in 4 mls of culture, ranged from 32-60 μg/ml (32, 53, 54, 58 and 60 μg/ml), with total IgG in the culture ranging from 128 to 240 μg.

These results show that high affinity scFv or Fab identified by phage display techniques may be recombinantly conjugated to immunoglobulin constant regions in order to generate high-affinity whole human antibodies.

Example 7

Analysis by Neutralization Assay of Re-Formatted IgG Antibodies

Whole human gastrin-specific IgG was isolated from cell supernatants and analyzed by calcium flux neutralization assay as described previously.

Re-formed whole IgG anti-gastrin antibodies were tested at $IC_{25}$ (0.3 nM) and $IC_{75}$ (1.7 nM) values as calculated from an earlier dose response experiment with murine monoclonal antibody Mu mAb2. Mu mAb2 and XPA067 were also tested at 67 nM as a control for maximum neutralization in this experiment.

Analysis of reformatted XPA067, XPA08, XPA0121, and XPA016 antibodies showed that XPA067 and Mu mAb2 at 67 nM exhibited approximately 85% and 95% neutralization, respectively. At 1.7 nM, Mu mAb2 and XPA067 each showed approximately 55% calcium flux neutralization, XPA088 and XPA011 each exhibited approximately 30% inhibiton, and XPA0121 exhibited approximately 10% neutralization. At 0.3 nM, all antibodies demonstrated 10% or less neutralization.

Lead antibody selection was then based on two criteria: (1) calcium flux IC50 value and (2) KD measurement. A more qualitative pERK1/2 dose response was also performed to confirm neutralization of gastrin-induced signaling in a different signaling pathway. Dose response studies indicate that at 0.01 nM neutralization is 100% for XPA067, XPA061 and murine antibodies Mu mAB2 and Mu mAb4. $IC_{50}$, $K_d$ and pERK $IC_{50}$ are shown in Table 2.

TABLE 2

| Antibody | Ca Flux IC50 (nM) | KD (nM) | pERK IC50 (nM) |
| --- | --- | --- | --- |
| XPA067 | 0.76 ± 0.38 | 3.9 | 0.56 ± 0.13 |
| Mu mAb2 | 0.53 ± 0.29 | 6.2 | 0.28 ± 0.03 |
| XPA061 | 1.34 ± 0.21 | 9.9 | 0.42 ± 0.11 |
| Mu mAb4 | 2.63 | 14.2 | 0.49 ± 0.35 |

Results from the calcium flux dose response experiments and affinity measurements indicate that antibodies derived from human phage display libraries and off-rate criteria to select high affinity binding antibodies leads to generation of human antibodies equivalent to murine hybridoma derived antibodies in potency and ability to neutralize calcium flux.

Example 8

Affinity Maturation of Anti-Gastrin IgG Antibodies

Affinity maturation was carried out for XPA067 as follows to optimize affinity. Libraries of antibodies were produced where random mutagenesis of the following regions was carried out; $V_H$ and $V_L$ CDR3, $V_H$ CDR1, $V_H$ CDR2 and $V_L$ CDR1. The libraries were constructed using standard molecular biology techniques as described in Clackson and Lowman, Phage Display—A Practical Approach (Oxford University Press 2004).

Each CDR3 was randomized in two blocks of 6 amino acids in order to cover the entire CDR, producing libraries H3B1 (N terminal block of 6 aa VH CDR3), H3B2 (C terminal block of 6 aa in VH CDR3), L3B1 (N terminal block of 6 aa in VL CDR3) and L3B2 (C terminal block of 6 aa in VL CDR3). $V_H$ CDR1 was randomized including the vernier residue at position 30 (Kabat, E. A. et al, Sequences of Proteins of Immunological Interest. 4$^{th}$ Edition, US Department of Health and Human Services. 1987, and Kabat, E. A. et al. (1991) Sequences of Proteins of Immunological Interest, 5th Edition. US Department of Health and Human Services, Public Service, NIH, Washington) to produce library H1. $V_H$ CDR2 was randomized at residues 50, 52, 53, 54, 56 and 58, to produce library H2. $V_L$ CDR1 was randomized at residues 27A, 27B, 27C, 29, 31 and 32 to produce library L1. Affinity-based selections were then performed on five (H3B1, H3B2, L3B1, L3B2, H2) of the seven libraries, whereby the concentration of target antigen was reduced over successive rounds of selection (Clackson and Lowman, Phage Display—A Practical Approach, Oxford University Press, 2004). At each stage of the optimization process, scFv that were able to inhibit the binding of clone XPA067 IgG1 to the target antigen were identified and assessed as described.

Example 9

Screening of Affinity Matured Ab Using the DELFIA® Competition Assay

Individual scFv obtained from the affinity-based selection of libraries of antibodies from CDR randomization of Ab clone XPA067, were tested for the ability to inhibit the binding of gastrin to the parent XPA067 IgG antibody. The microplate based competitive screening DELFIA® assay (Perkin Elmer) was performed according to protocols provided by manufacturer. ScFv contained in periplasmic extracts of individual clones were assayed at different dilutions to reflect 20%, 10% and 5% periplasmic extract content in the sample assay. ScFv that at the highest dilution inhibited more than 80% the binding of gastrin to XPA067 IgG were further characterized to isolate the lead affinity matured antibody.

The top 11 scFv were converted to scFv-Fc as described in Example 5 and used for analytical and functional ranking of Ab as described in Examples 2, 6, and 9. The amino acid sequences of the 11 affinity matured antibodies is set out in FIG. 3 and SEQ ID NOs: 23-33. FIG. 4 is a comparison of the CDR regions of the originating XPA067 antibody and the affinity matured antibodies.

Example 10

Determination of Binding Affinity of Matured Abs

Affinities of the parental (XPA067) and matured antibody fragments were determined by surface plasmon resonance using a BIACORE® 2000. Affinity constants were calculated from the kinetic rate constants for antibody binding to biotinylated peptide immobilized on a Streptavidin sensor chip.

A very low density of peptide was immobilized in order to avoid bivalent binding by the antibodies to the sensor chip. Antibodies were tested in triplicate at six concentrations of three-fold serial dilutions. Data were analyzed using BiaEval Software.

The gastrin-binding affinities of four matured antibody fragments are shown in Table 3.

TABLE 3

| Affinity Matured Ab | Approximate Affinity |
|---|---|
| XPA067.18 | 40-80 pM |
| XPA067.06 | 20 pM |
| XPA067.09 | 180 pM |
| XPA067.11 | <500 pM |
| XPA067 | 5 nM |

These results indicate that the affinity maturation process successfully generates antibodies with greater antigen affinity that the starting parent antibody.

Example 11

Experimental Models Useful in Measuring Antibody Efficacy

To evaluate the efficacy of anti-gastrin antibodies as a therapeutic in conditions or diseases in which gastrin activity is detrimental, experimental animal models that are accepted models for human disease are used as a readout. Useful experimental models include, but are not limited to, those described below.

Pancreatic Cancer

In one embodiment, an orthotopic model is used in which PAN1 cells (human pancreatic cancer) are injected into the tail of the pancreas of 5-7 nude mice ($10^4$ cells in 0.1 mL). Rabbit anti-gastrin G17 (antiserum is administered daily, iv (or ip) at 150 mg protein/mouse. Rabbits vaccinated with G17 will raise antibodies capable of binding human gastrin forms. Thus, rabbit G17 antisera contains gastrin-neutralizing antibodies. In this model both monotherapy with the composition of the invention and combination therapy antibody substance plus the a second therapeutic such as gemcitibine (GEMZAR®) are evaluated. In combination therapy experiments gemcitibine is given on day 1, 3, and 6 at 4 mg/kg. Studies are terminated when the tumor burden affected clinical condition of mice (weight loss, ascites and cachexia).

Gastric Cancer

In one embodiment, an intraperitoneal tumor model using cell lines: MGLVA1 and ST16 isolated from human gastric tumors is used (Watson et al., *Gut* 45:812-7 (1999)). Cells are injected into the peritoneal cavity of SCID mice (n=10) and gastrin-specific antibody of the invention is administered daily, iv (serum ABC of 7.5×10-9M). The study is terminated when tumor burden affected clinical condition of mice (weight loss, ascites and cachexia).

Colorectal Cancer

In one embodiment, AP5LV cells ($5 \times 10^6$) are injected into abdominal wall muscle layer of SCID mice (Watson et al., *Int J Cancer* 61:233-40 (1995)). Antibody of the invention is administered daily, iv (serum ABC of 3.75×10-9M). Mice are terminated on day 28 and lung metastasis is measured.

Evidence that certain G.I. tumors produce gastrin and are mitogenic to gastrin can be found in several areas: in vitro cell line studies, studies performed with human tumor tissue, and in vivo animal models. It is expected that treatment of certain G.I. tumors with gastrin-neutralizing Abs of the invention will have clinical benefit if the G.I. tumors proliferate in response to gastrin exposure and/or produce gastrin which stimulates them to through autocrine and paracrine pathways to proliferate.

Experimental Autoimmune Gastritis

Experimental models of gastritis can be induced in BALB/c mice by immunization with the gastric H/K-ATPase (Alderuccio et al., *Autoimmunity* 25:167-175 (1997)); Scarff et al., *Immunology* 92:91-98 (1997)) or by a variety of manipulations that result in transient lymphopenia (Gleeson et al., *Immunol Rev* 149:97-125 (1996)), or by thymectomizing mice (Barrett et al., *Eur J Immunol* 25:238-244 (1995)). Further, a spontaneous mutation in mice that induces autoimmune gastritis characterized by autoantibodies to the gastric H/K-ATPase (Alderuccio et al., *Am J of Pathol.* 153:1311-1318 (1998)).

Duodenal Ulcers/*H Pylori* Infection

Experimental models of duodenal ulcers induced by ethanol gavage in Sprague-Dawley rats are described in Krantis et al., (*Dig Dis Sci.* 38:722-9 (1993)). Infection of *H Pylori* and induction of ulcers is described in Ross et al., (*Am J Pathol.* 141:721-7 (1992)), which describes induction and monitoring of *H. pylori* induced ulcers in Sprague Dawley rats, and in Mahler et al., (*Helicobacter.* 10:332-44 (2005)), which describes *H. pylori* induced ulcers in the hispid cotton rat. Other animals models useful to evaluate *H. pylori* infection are available and known in the art. See e.g., a mouse model is described in Day et al., (*Dig Dis Sci.* 46:1943-51 (2001)), and a Mongolian gerbil model is described in Sawada et al., (*J. Gastroenterol.* 34 Suppl 11:55-60 (1999)).

Example 12

Affinity and Efficacy of Reformatted Antibody In Vitro

Affinity matured antibodies were reformatted to comprise an IgG tail as described in Example 6 and the affinity of these reformatted antibodies to bind gastrin and to neutralize the effects of gastrin in vitro were measured.

Antibody affinity was measured as described previously. The reformatted, affinity matured antibodies showed improved affinities compared to the parent antibody. See Table 4.

TABLE 4

| Sample Id | Approximate Affinity |
|---|---|
| XPA067.18 | 17 pM |
| XPA067.06 | 31 pM |
| XPA067 | 5 nM |

To determine the efficacy of gastrin neutralization by these antibodies in vitro, an in vitro calcium flux assay was performed as described in Example 3. Briefly, flow cytometric measurement of intracellular calcium flux was carried out in a CCK2R overexpressing cell line (AGS-TR).

Reformatted antibodies XPA067, XPA067.06 and XPA067.18 were assayed for their ability to neutralize gastrin activation of calcium flux in these cells. FIG. 5 shows the results of the calcium flux assay. Parent antibody XPA067 demonstrated approximately 50% gastrin neutralization at a concentration of approximately 1 nM. Affinity matured antibody XPA067.06 reached 50% neutralization at about 0.17 nM and affinity matured antibody XPA067.18 showed 50% neutralization at about 0.2 nM.

These results demonstrate that the affinity matured antibodies exhibit greater affinity for gastrin and therefore show increased neutralization at a lower concentration of antibody compared to the parent antibody. This suggests that a lower dosage of a higher affinity antibody would be required to effectuate neutralization of gastrin in vivo. However, the parent antibody was able to achieve 90% neutralization at about 10 nM and, therefore, may be suitable for some therapeutic applications.

Example 13

Efficacy of Reformatted Antibody In Vivo

Monitoring pH changes can serve as a pharmacological end point to measure the in vivo efficacy of the therapeutic anti-gastrin antibody. Previous studies have demonstrated that agents such as famotidine, an $H_2$-receptor antagonist that inhibits stomach acid production, and telenzepine, a muscarinic M1-receptor antagonist that inhibits gastric acid secretion, can increase the gastric pH in CD-1 mice. A biologically active anti-gastrin antibody should also neutralize the function of endogenous gastrin and increase the gastric pH level.

Human gastrin interacts with mouse receptors and has effect on gastric acid secretion in vivo. Therefore, a gastric pH model was modified to assess in vivo gastrin neutralization activity of anti-gastrin antibodies by introducing human gastrin (h-G17) into CD-1 mice and administering anti-human gastrin antibodies. Thus, the neutralization of the exogenous human gastrin by the anti-gastrin antibody could be detected by measuring gastric pH.

To evaluate the in vivo efficacy of the anti-gastrin mAbs, the effect of target neutralization was measured using gastric pH as the readout. On study day −2 (48 hours before gastric fluid collection), CD-1 mice (12-14 weeks old) were treated with anti-gastrin mAbs (20 mg/kg body wt) or anti-KLH IgG1 antibody control (20 mg/kg body wt) by intraperitoneal injection. Mice were given NAPA-NECTAR™ water gel instead of solid Rodent Chow. On study day −1 (24 hours before gastric fluid collection), mice were fasted overnight with free access to water. On study day 0 (the day of gastric fluid collection), human gastrin h-G17 (1 mg/kg body wt; Sigma) or PBS (pH 7.4) was injected subcutaneously. Twenty minutes after h-G17 or PBS injection, a H2R antagonist (famotidine; 30 mg/kg body wt; Sigma), a muscarinic M1 receptor antagonist (telenzepine; 30 mg/kg body wt; Sigma) or PBS was administered intravenously into each mouse. The stomach was removed one hour later. Approximately 50 µL of gastric fluid was collected, and the pH was directly measured by using a pH meter (model D-51; Horiba Ltd., Kyoto, Japan) with micro electrode (model 9669-10D; Horiba Ltd.).

Figure 6:
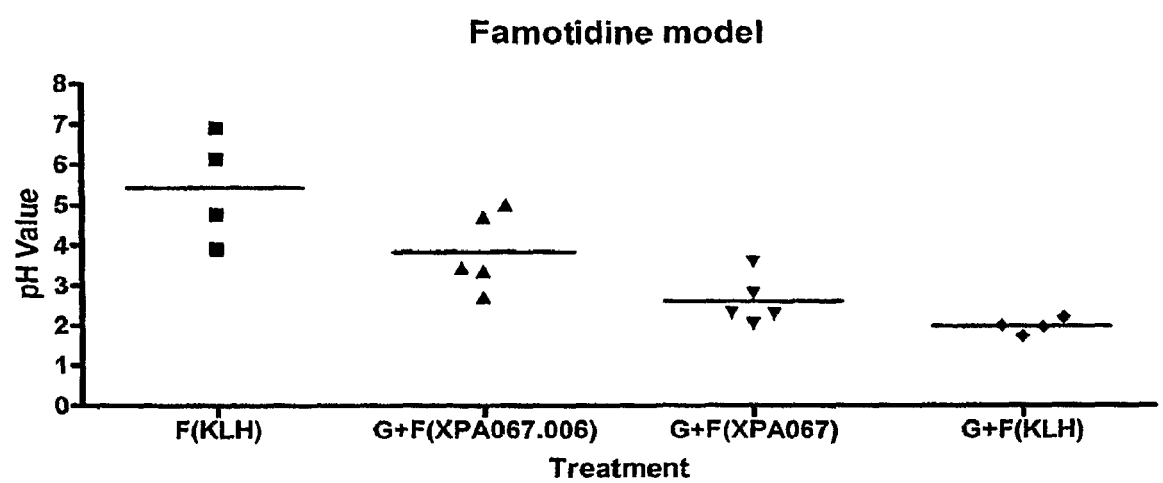
FIG. 6 shows the neutralization of anti-gastrin antibodies in a gastric pH famotidine mouse model. F: Fainotidine, G: h-G17 (human gastrin), XPA067: parental α-gastrin mAb, XPA067.06: affinity mature α-gastrin mAb.

FIG. 6 shows that administration of famotidine alone neutralizes endogenous mouse gastric acid and raises the pH levels in the stomach to approximately pH 5.5, while administration of exogenous human gastrin and famotidine reduced the stomach pH levels to approximately pH 2. Thus, at the doses given famotidine cannot neutralize the effect of exogenous gastrin. Administration of anti-gastrin antibody XPA067, human gastrin and famatodine demonstrated a slight increase in stomach pH, to pH 2.5. However, administering the affinity matured anti-gastrin antibody XPA067.06 instead of XPA067 can further increase the pH in the stomach to approximately pH 4.

Figure 7:
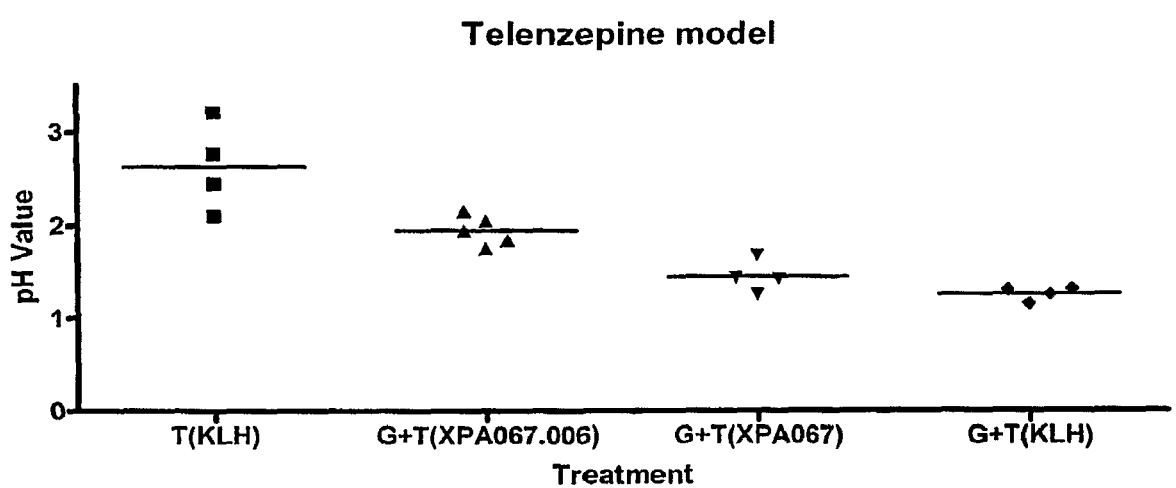
FIG. 7 shows the neutralization of anti-gastrin antibodies in a gastric pH telenzepine mouse model. T: Telenzepine, G: h-G17 (human gastrin), XPA067: parental α-gastrin mAb, XPA067.06: affinity mature α-gastrin mAb.

FIG. 7 demonstrates that administration of telenzepine alone neutralizes endogenous mouse gastric acid and raises the pH levels in the stomach to approximately pH 3, while administration of exogenous human gastrin and telenzepine reduced the stomach pH levels to approximately pH 1.3. Administration of anti-gastrin antibody XPA067, human gastrin and telenzepine demonstrated a slight increase in stomach pH, to pH 1.5. However, administering the affinity matured anti-gastrin antibody XPA067.06 instead of XPA067 can further increase the pH in the stomach to approximately pH 2.

These results demonstrate that normal levels of gastric acid secretion are decreased by administration of the selective H2R antagonist, famotidine, or the muscarinic M1 receptor antagonist, telenzepine. In addition, these effects can be abolished by pre-introducing exogenous human gastrin to CD-1 mice. The anti-gastrin mAbs neutralizes exogenous human gastrin in vivo. Elevation of gastric pH was observed after administration of the neutralizing anti-gastrin antibodies. The in vivo data also indicates the affinity-matured antibody, XPA067.06, is a more potent gastrin-neutralizing agent than the parental antibody, XPA067.

The data herein show that a monoclonal antibody with affinity of about $10^{-9}$ M was able to achieve 90% neutralization of gastrin-induced calcium flux activity in vitro at a concentration of about 10 nM, and has minimal influence on the acid-stimulating effects of gastrin in vivo in two animal models. Monoclonal antibodies with affinity of about $10^{-12}$ M achieved 90% neutralization of gastrin in vitro at a concentration of 0.17 or 0.2 nM, and produced marked neutralization of gastrin's acid-stimulating effects in vivo in the same animal models. The relatively modest 5-fold improvement in neutralization upon a 3 log increase in affinity indicates that antibodies of much higher affinity (i.e. with an affinity value of less than $10^{-10}$ or $10^{-11}$ M) may not provide significantly better neutralization.

The relatively modest 5-fold improvement in neutralization upon a 3 log increase in affinity indicates that antibodies of much higher affinity (i.e. with an affinity value of less than $10^{-10}$ or $10^{-11}$ M) provide better neutralization and enhance pharmacological efficacy.

Numerous modifications and variations in the invention as set forth in the above illustrative examples are expected to occur to those skilled in the art. Consequently only such limitations as appear in the appended claims should be placed on the invention.

We claim:

1. An isolated antibody that binds gastrin (gastrin 17) with an affinity kd of $10^{-7}$ M or less that comprises:
  (a) a heavy chain CDR1 amino acid sequence set forth in SEQ ID NOs: 1, 3, 5, 7, 9, 11 or 23-33, a variant thereof in which one or two amino acids have been changed by conservative amino acid substitution, or a consensus sequence thereof;
  (b) a heavy chain CDR2 amino acid sequence set forth in SEQ ID NOs: 1, 3, 5, 7, 9, 11 or 23-33, or a variant thereof in which one or two amino acids have been changed by conservative amino acid substitution or a consensus sequence thereof;
  (c) a heavy chain CDR3 amino acid sequence set forth in SEQ ID NOs: 1, 3, 5, 7, 9, 11 or 23-33 or a variant thereof in which one or two amino acids have been changed by conservative amino acid substitution, or a consensus sequence thereof;
  (d) a light chain CDR1 amino acid sequence set forth in SEQ ID NOs: 2, 4, 6, 8, 10 or 12, or a variant thereof in which one or two amino acids have been changed by conservative amino acid substitution;
  (e) a light chain CDR2 amino acid sequence set forth in SEQ ID NOs: 2, 4, 6, 8, 10 or 12, or a variant thereof in which one or two amino acids have been changed by conservative amino acid substitution; and
  (f) a light chain CDR3 amino acid sequence set forth in SEQ ID NOs: 2, 4, 6, 8, 10 or 12, or a variant thereof in which one or two amino acids have been changed by conservative amino acid substitution.

2. The antibody of claim 1 wherein one or more of said heavy chain CDR1, CDR2 or CDR3 amino acid sequences is a consensus sequence set forth in SEQ ID NO: 11.

3. The antibody of claim 1 wherein
  (a) an amino acid in a heavy chain CDR1 amino acid sequence is replaced with an amino acid from a corresponding position within a different heavy chain CDR1 amino acid sequence set forth in SEQ ID NOs: 1, 3, 5, 7, 9, 11 or 23-33; or
  (b) an amino acid in a heavy chain CDR2 amino acid sequence is replaced with an amino acid from a corresponding position within a different heavy chain CDR2 amino acid sequence set forth in SEQ ID NOs: 1, 3, 5, 7, 9, 11 or 23-33; or (c) an amino acid in a heavy chain CDR3 amino acid sequence is replaced with an amino acid from a corresponding position within a different heavy chain CDR3 amino acid sequence set forth in SEQ ID NOs: 1, 3, 5, 7, 9, 11 or 23-33.

4. The antibody of claim 1 that comprises a heavy chain variable region amino acid sequence set forth in SEQ ID NOs: 1, 3, 5, 7, 9, 11 or 23-33.

5. The antibody of claim 1 in which one or more heavy chain framework amino acids have been replaced with corresponding amino acid(s) from another human antibody amino acid sequence.

6. The antibody of claim 1 further comprising a human heavy chain constant region attached to said heavy chain variable region.

7. The antibody of claim 1 wherein one or more of said light chain CDR1, CDR2 or CDR3 amino acid sequences is a consensus sequence set forth in SEQ ID NO: 12.

8. The antibody of claim 1 wherein
(a) an amino acid in a light chain CDR1 amino acid sequence is replaced with an amino acid from a corresponding position within a different light chain CDR1 amino acid sequence set forth in SEQ ID NOs: 2, 4, 6, 8, 10 or 12; or
(b) an amino acid in a light chain CDR2 amino acid sequence is replaced with an amino acid from a corresponding position within a different light chain CDR2 amino acid sequence set forth in SEQ ID NOs: 2, 4, 6, 8, 10 or 12; or
(c) an amino acid in a light chain CDR3 amino acid sequence is replaced with an amino acid from a corresponding position within a different light chain CDR3 amino acid sequence set forth in SEQ ID NOs: 2, 4, 6, 8, 10 or 12.

9. The antibody of claim 1 that comprises a light chain variable region amino acid sequence set forth in SEQ ID NOs: 2, 4, 6, 8, 10 or 12.

10. The antibody of claim 1 in which one or more light chain framework amino acids have been replaced with corresponding amino acid(s) from another human antibody amino acid sequence.

11. The antibody of claim 1 further comprising a human light chain constant region attached to said light chain variable region.

12. An antibody of claim 1 that exhibits at least 70% neutralization of calcium flux in an assay using AGS-TR cells, wherein the tested antibody is at a concentration in 100 molar excess over gastrin, and wherein gastrin is at the EC50 concentration (1 nM).

13. The antibody of claim 1 that comprises 6 CDRs of any of XPA061 (SEQ ID NO: 1 and 2), XPA063 (SEQ ID NO: 3 and 4), XPA065 (SEQ ID NO: 5 and 6), XPA067 (SEQ ID NO: 7 and 8), and XPA081 (SEQ ID NO: 9 and 10).

14. The antibody of claim 1 which is a single chain antibody.

15. The antibody of claim 1 that is conjugated to another diagnostic or therapeutic agent.

16. A pharmaceutical composition comprising an antibody of claim 1 and a pharmaceutically acceptable carrier.

17. A kit comprising an antibody of claim 4 and instructions for use.

18. An isolated monoclonal antibody that binds gastrin (gastrin 17) with an affinity kd of $10^{-8}$ M or less that comprises:
(a) a heavy chain CDR1 amino acid sequence set forth in SEQ ID NOs: 1, 3, 5, 7, 9, 11 or 23-33, a variant thereof in which one or two amino acids have been changed by conservative amino acid substitution, or a consensus sequence thereof;
(b) a heavy chain CDR2 amino acid sequence set forth in SEQ ID NOs: 1, 3, 5, 7, 9, 11 or 23-33, or a variant thereof in which one or two amino acids have been changed by conservative amino acid substitution or a consensus sequence thereof;
(c) a heavy chain CDR3 amino acid sequence set forth in SEQ ID NOs: 1, 3, 5, 7, 9, 11 or 23-33, or a variant thereof in which one or two amino acids have been changed by conservative amino acid substitution, or a consensus sequence thereof;
(d) a light chain CDR1 amino acid sequence set forth in SEQ ID NOs: 2, 4, 6, 8, 10 or 12, or a variant thereof in which one or two amino acids have been changed by conservative amino acid substitution;
(e) a light chain CDR2 amino acid sequence set forth in SEQ ID NOs: 2, 4, 6, 8, 10 or 12, or a variant thereof in which one or two amino acids have been changed by conservative amino acid substitution; and
(f) a light chain CDR3 amino acid sequence set forth in SEQ ID NOs: 2, 4, 6, 8, 10 or 12, or a variant thereof in which one or two amino acids have been changed by conservative amino acid substitution.

19. The antibody of claim 1 wherein the heavy chain CDR2 and CDR3 amino acid sequences are from the same heavy chain variable region as the CDR1 amino acid sequence.

20. The antibody of claim 1 wherein the light chain CDR2 and CDR3 amino acid sequences are from the same light chain variable region as the CDR1 amino acid sequence.

21. The antibody of claim 1 that comprises heavy chain CDR1, CDR2 and CDR3 of any of XPA067.06 (SEQ ID NO: 23) and XPA067.18 (SEQ ID NO: 29).

22. A method for treating a condition or disorder selected from the group consisting of pancreatic cancer, esophageal cancer, gastric cancer, colorectal cancer, small lung cell carcinoma, gastric ulcer, duodenal ulcer, other ulcers or conditions associated with *H. Pylori*, gastroesophageal reflux disease, autoimmune gastritis, atrophic body gastritis, Zollinger-Ellison syndrome associated with tumor of the pancreas (gastrinoma), or inflammatory bowel disease comprising the step of administering to a subject in need a therapeutically effective amount of the pharmaceutical composition of claim 16.

23. The method of claim 22 wherein the antibody is administered in conjunction with a second therapeutic agent.

* * * * *

UNITED STATES PATENT AND TRADEMARK OFFICE
CERTIFICATE OF CORRECTION

| | | |
|---|---|---|
| PATENT NO. | : 8,278,421 B2 | Page 1 of 1 |
| APPLICATION NO. | : 12/293890 | |
| DATED | : October 2, 2012 | |
| INVENTOR(S) | : Linda Masat et al. | |

It is certified that error appears in the above-identified patent and that said Letters Patent is hereby corrected as shown below:

On the Cover Page Item (73)

Assignee should be changed to:

Xoma Technology Ltd.

Signed and Sealed this
Twentieth Day of November, 2012

David J. Kappos
*Director of the United States Patent and Trademark Office*